United States Patent
Fukazawa et al.

(10) Patent No.: US 9,328,062 B2
(45) Date of Patent: May 3, 2016

(54) IMIDE COMPOUND, METHOD FOR MANUFACTURING SAME, AND USE AS INSECTICIDE

(71) Applicant: Mitsui Chemicals Agro, Inc., Tokyo (JP)

(72) Inventors: Yasuaki Fukazawa, Kawasaki (JP); Hironari Okura, Mobara (JP); Toshiyuki Kohno, Chiba (JP); Teruko Kawaguchi, Tokyo (JP); Takeo Wakita, Mobara (JP)

(73) Assignee: MITSUI CHEMICALS AGRO, INC., Tokyo (JP)

( * ) Notice: Subject to any disclaimer, the term of this patent is extended or adjusted under 35 U.S.C. 154(b) by 0 days.

(21) Appl. No.: 14/433,787

(22) PCT Filed: Oct. 4, 2012

(86) PCT No.: PCT/JP2012/075844
§ 371 (c)(1),
(2) Date: Apr. 6, 2015

(87) PCT Pub. No.: WO2014/054158
PCT Pub. Date: Apr. 10, 2014

(65) Prior Publication Data
US 2015/0246872 A1    Sep. 3, 2015

(51) Int. Cl.
| | | |
|---|---|---|
| *C07C 237/52* | (2006.01) | |
| *C07C 231/12* | (2006.01) | |
| *A01N 37/26* | (2006.01) | |
| *A01N 37/48* | (2006.01) | |
| *C07C 237/42* | (2006.01) | |
| *A01N 37/46* | (2006.01) | |

(52) U.S. Cl.
CPC .............. *C07C 237/52* (2013.01); *A01N 37/26* (2013.01); *A01N 37/46* (2013.01); *A01N 37/48* (2013.01); *C07C 231/12* (2013.01); *C07C 237/42* (2013.01)

(58) Field of Classification Search
None
See application file for complete search history.

(56) References Cited

FOREIGN PATENT DOCUMENTS

| WO | 2005/021488 | 3/2005 |
|----|-------------|--------|
| WO | 2005/073165 | 8/2005 |

*Primary Examiner* — Timothy R Rozof
(74) *Attorney, Agent, or Firm* — Rankin, Hill & Clark LLP

(57) ABSTRACT

The invention provides an imide compound represented by the following Formula (1) and an insecticide including the imide compound:

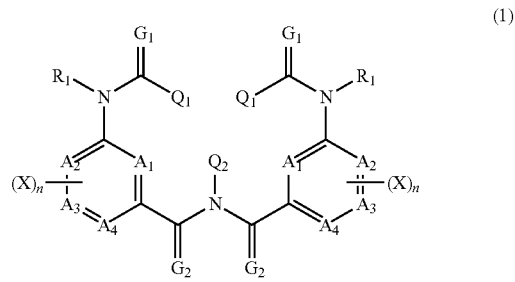

wherein, each of $A_1$, $A_2$, $A_3$, and $A_4$ represents a carbon atom, a nitrogen atom, or an oxidized nitrogen atom; $R_1$ represents a hydrogen atom, an alkyl group which may be substituted, or a C2-C4 alkylcarbonyl group which may be substituted; each of $G_1$ and $G_2$ independently represents an oxygen atom or a sulfur atom; each X may be the same as or different from one another and represents a hydrogen atom, a halogen atom, a C1-C3 alkyl group, or a trifluoromethyl group; n represents an integer from 0 to 4; and each of $Q_1$ and $Q_2$ represents a phenyl group, naphthyl group, or a heterocyclic group, each of which may be substituted.

10 Claims, No Drawings

IMIDE COMPOUND, METHOD FOR MANUFACTURING SAME, AND USE AS INSECTICIDE

TECHNICAL FIELD

The invention relates to an imide compound, a method for manufacturing the imide compound, and an insecticide.

BACKGROUND ART

A compound as an insecticide similar to the compound according to the invention is described in the pamphlet of International Publication WO 2005/21488. Another compound as an insecticide similar to the compound according to the invention is described in the pamphlet of International Publication WO 2005/73165.

SUMMARY OF INVENTION

Technical Problem

It is apparent that the compound described in the pamphlet of international Publication WO 2005/21488 and the compound described in the pamphlet of International Publication WO 2005/73165 are out of the scope of the claims according to the present invention.

An object of the invention is to provide an imide compound with a high insecticidal effect. Another object of the invention is to provide a method for manufacturing the imide compound, an insecticide including the imide compound as an active ingredient, and a mixed preparation obtained by combining the imide compound with other insecticide and/or fungicide.

Solution to Problem

As a result of intensive studies by the present inventors to solve the problem, it was found that the imide compound according to the invention is a novel compound unknown in the literature and has a particularly high insecticidal effect, whereby novel use of the imide compound is provided. The inventors also found a novel compound unknown in the literature that is useful as an intermediate for manufacturing the compound according to the invention. As a result, the invention has been completed. That is, the present invention is as follows.

[1] An imide compound represented by the following Formula (1).

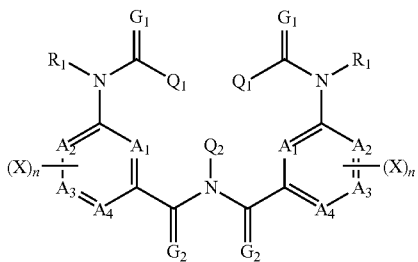

In Formula (1), each of $A_1$, $A_2$, $A_3$, and $A_4$ independently represents a carbon atom, a nitrogen atom, or an oxidized nitrogen atom; each $R_1$ independently represents a hydrogen atom, a C1-C4 alkyl group which may be substituted, or a C2-C4 alkylcarbonyl group which may be substituted; each of $G_1$ and $G_2$ independently represents an oxygen atom or a sulfur atom; each X independently represents a hydrogen atom, a halogen atom, a C1-C3 alkyl group, or a trifluoromethyl group; when there are two or more X's, each X may be the same as or different from one another; and n represents an integer from 0 to 4; and wherein each $Q_1$ independently represents a phenyl group which may be substituted, a naphthyl group which may be substituted, or a heterocyclic group which may be substituted; and $Q_2$ represents a phenyl group or a heterocyclic group, each of which has one or more substituents, wherein at least one of the one or more substituents represents a C1-C4 haloalkoxy group, a C2-C6 perfluoroalkyl group, a C1-C6 perfluoroalkylthio group, a C1-C6 perfluoroalkylsulfinyl group, or a C1-C6 perfluoroalkylsulfonyl group.

[2] The imide compound according to [1], in which, in Formula (1), each $R_1$ independently represents a hydrogen atom or a C1-C4 alkyl group;

each X independently represents a hydrogen atom, a halogen atom, or a trifluoromethyl group;

each $Q_1$ independently represents:

a phenyl group that may have one or more substituents, which may be the same as or different from one another, selected from the substituent group consisting of a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a mono-(C1-C4) alkylamino group, a di-(C1-C4) alkylamino group, a cyano group, a nitro group, a hydroxy group, a formyl group, a C2-C4 alkylcarbonyl group, a C2-C4 alkylcarbonyloxy group, a C2-C4 alkoxycarbonyl group, an acetylamino group and a phenyl group; or a heterocyclic group selected from the group consisting of a pyridyl group, a pyridine-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrole group, a pyrazolyl group and a tetrazolyl group, wherein the heterocyclic group may have one or more substituents, which may be the same as or different from one another, selected from the substituent group consisting of a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfinyl group, a mono-(C1-C4) alkylamino group, a di-(C1-C4)alkylamino group, a cyano group, a nitro group, a hydroxy group, a formyl group, a C2-C4 alkylcarbonyl group, a C2-C4 alkylcarbonyloxy group, a C2-C4 alkoxycarbonyl group, an acetylamino group and a phenyl group; and $Q_2$ represents:

a phenyl group having a substituent represented by the following Formula (2):

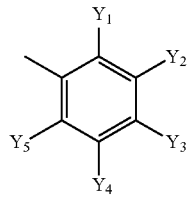

(2)

wherein, in Formula (2), each of $Y_1$ and $Y_5$ independently represents a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, or a cyano group; $Y_3$ represents a C2-C6 perfluoroalkyl group, a C1-C6 perfluoroalkylthio group, a C1-C6 perfluoroalkylsulfinyl group, or a C1-C6 perfluoroalkylsulfonyl group; and each of $Y_2$ and $Y_4$ independently represents a hydrogen atom, a halogen atom, or a C1-C4 alkyl group; or a pyridyl group having a substituent represented by the following Formula (3):

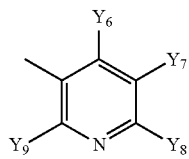

(3)

in Formula (3), each of $Y_6$ and $Y_9$ independently represents a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, or a cyano group; $Y_8$ represents a C1-C4 haloalkoxy group, a C2-C6 perfluoroalkyl group, a C1-C6 perfluoroalkylthio group, a C1-C6 perfluoroalkylsulfinyl group, or a C1-C6 perfluoroalkylsulfonyl group; and $Y_7$ represents a hydrogen atom, a halogen atom, or a C1-C4 alkyl group.

[3] The imide compound according to [2], which is represented by the following Formula (1a):

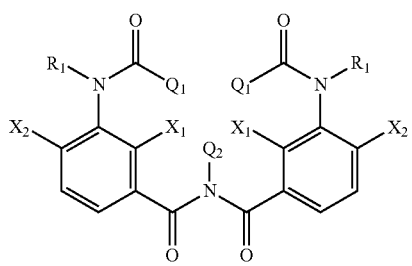

(1a)

in Formula (1a), $Q_2$ represents a phenyl group having a substituent represented by the following Formula (2):

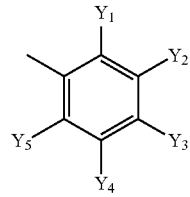

(2)

in Formula (2), each of $Y_1$ and $Y_5$ independently represents a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, or a cyano group; $Y_3$ represents a C2-C6 perfluoroalkyl group; and each of $Y_2$ and $Y_4$ independently represents a hydrogen atom or a C1-C4 alkyl group, each of $X_1$ and $X_2$ independently represents a hydrogen atom or a fluorine atom; $R_1$ represents a hydrogen atom or a C1-C4 alkyl group; and $Q_1$ represents:
a phenyl group that may have one or more substituents, which may be the same as or different from one another, selected from the substituent group consisting of a halogen atom, a C1-C4 alkyl group, a C1-C4 haloalkyl group, a cyano group and a nitro group,
a pyridyl group that may have one or more substituents, which may be the same as or different from one another, selected from the substituent group consisting of a halogen atom, a C1-C4 alkyl group, a C1-C4 haloalkyl group, a cyano group and a nitro group.

[4] A method of manufacturing the imide compound represented by Formula (1) according to [1], the method including:

reacting a compound represented by the following Formula (4) with a compound represented by the following Formula (5):

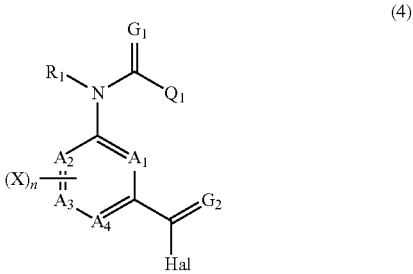

(4)

in Formula (4), each of $A_1$, $A_2$, $A_3$, and $A_4$ independently represents a carbon atom, a nitrogen atom, or an oxidized nitrogen atom; $R_1$ represents a hydrogen atom, a C1-C4 alkyl group, or a C1-C4 alkylcarbonyl group; each of $G_1$ and $G_2$ independently represents an oxygen atom or a sulfur atom; each X independently represents a hydrogen atom, a halogen atom, a C1-C3 alkyl group, or a trifluoromethyl group; when there are two or more X's, each X may be the same as or different from one another; and n represents an integer from 0 to 4;

$Q_1$ represents a phenyl group which may be substituted, a naphthyl group which may be substituted, or a heterocyclic group which may be substituted; and Hal represents a chlorine atom or a bromine atom,

(5)

in Formula (5), $Q_2$ represents a phenyl group or a heterocyclic group, each of which has one or more substituents, in which at least one of the one or more substituents represents a C1-C4 haloalkoxy group, a C2-C6 perfluoroalkyl group, a C1-C6 perfluoroalkylthio group, a C1-C6 perfluoroalkylsulfinyl group, or a C1-C6 perfluoroalkylsulfonyl group.

[5] The method of manufacturing the imide compound according to [4], in which $Q_1$ in Formula (4) represents:

a phenyl group that may have one or more substituents, which may be the same as or different from one another, selected from the substituent group consisting of a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a mono-(C1-C4) alkylamino group, a di-(C1-C4) alkylamino group, a cyano group, a nitro group, a hydroxy group, a formyl group, a C2-C4 alkylcarbonyl group, a C2-C4 alkylcarbonyloxy group, a C2-C4 alkoxycarbonyl group, an acetylamino group and a phenyl group; or a heterocyclic group selected from the group consisting of a pyridyl group, a pyridine-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrole group, a pyrazolyl group and a tetrazolyl group, wherein the heterocyclic group may have one or more substituents, which may be the same as or different from one another, selected from the substituent group consisting of a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a mono-(C1-C4) alkylamino group, a di-(C1-C4) alkylamino group, a cyano group, a nitro group, a hydroxy group, a formyl group, a C2-C4 alkylcarbonyl group, a C2-C4 alkylcarbonyloxy group, a C2-C4 alkoxycarbonyl group, an acetylamino group and a phenyl group.

[6] An insecticide comprising, as an active ingredient, the imide compound according to any one of [1] to [3].

[7] An agricultural/horticultural insecticide comprising, as an active ingredient, the imide compound according to any one of [1] to [3].

[8] method of using of an imide compound for protecting useful crops from pests, including treating a target useful crop or soil with an effective amount of the imide compound according to any one of [1] to [3].

[9] A composition including the imide compound according to any one of [1] to [3] and at least one of an inert carrier or an adjuvant.

[10] A mixed preparation including the imide compound according to any one of [1] to [3] and at least one selected from a pesticide or a fungicide, other than the imide compound.

Advantageous Effects of Invention

According to the invention, there can be provided an imide compound with a high insecticidal effect. In addition, according to the invention, there can be provided a method for manufacturing the imide compound, an insecticide including the imide compound as an active ingredient, and a mixed preparation obtained by combining the imide compound with other insecticide and/or fungicide.

DESCRIPTION OF EMBODIMENTS

The imide compound according to the invention is characterized in that it is represented by the following Formula (1).

The imide compound according to the invention exhibits a significant control effect as an insecticide at a low dose, and also exhibits a significant control effect when used in combination with other insecticides, miticides, nematocides, fungicides, herbicides, plant growth regulators, biological agricultural chemicals, or the like.

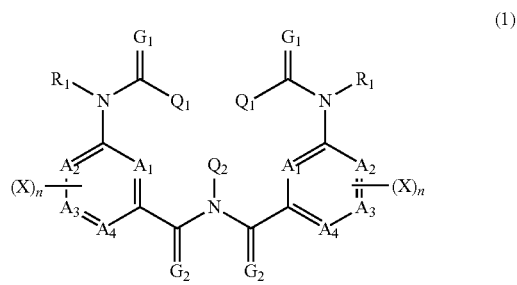
(1)

In Formula (1), each of $A_1$, $A_2$, $A_3$, and $A_4$ independently represents a carbon atom, a nitrogen atom, or an oxidized nitrogen atom. Each $R_1$ represents a hydrogen atom, a C1-C4 alkyl group which may be substituted, or a C1-C4 alkylcarbonyl group which may be substituted. Each of $G_1$ and $G_2$ independently represents an oxygen atom or a sulfur atom. Each X represents a hydrogen atom, a halogen atom, a C1-C3 alkyl group, or a trifluoromethyl group; and when there are two or more X's, each X may be the same as or different from one another; and n represents an integer from 0 to 4.

Each $Q_1$ represents a phenyl group which may be substituted, a naphthyl group which may be substituted, or a heterocyclic group which may be substituted. $Q_2$ represents a phenyl group or a heterocyclic group, each of which has one or more substituents, in which at least one of the one or more substituents represents a C1-C4 haloalkoxy group, a C2-C6 perfluoroalkyl group, a C1-C6 perfluoroalkylthio group, a C1-C6 perfluoroalkylsulfinyl group, or a C1-C6 perfluoroalkylsulfonyl group.

The terms used in the formulae including Formula (I) and the like according to the invention, have the meanings as described below in the definitions.

The "halogen atom" represents a fluorine atom, a chlorine atom, a bromine atom, or an iodine atom.

With regard to the expression "Ca-Cb (wherein a and b represent an integer of 1 or more)", for example, "C1-C3" means the number of carbon atoms of from 1 to 3, "C2-C6" means the number of carbon atoms of from 2 to 6, and "C1-C4" means the number of carbon atoms of from 1 to 4.

"n-" means normal and "t-" means tertiary (tert-).

The "C1-C4 alkyl group which may be substituted" represents a linear, branched, or cyclic alkyl group having from 1 to 4 carbon atoms that may have one or more substituents, which may be the same as or different from one another, selected from the substituent group consisting of a halogen atom, a hydroxy group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfinyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a mono-(C1-C6) alkylamino group, a di-(C1-C6) alkylamino group, a phenyl group which may be substituted, a phenylcarbonyl group which may be substituted, a phenylamino group which may be substituted, and a heterocyclic group which may be substituted.

The "C2-C4 alkylcarbonyl group which may be substituted" represents a linear, branched, or cyclic alkylcarbonyl group having from 2 to 4 carbon atoms that may have one or more substituents, which may be the same as or different from one another, selected from the substituent group consisting of a halogen atom, a hydroxy group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a mono-(C1-C6) alkylamino group, a di-(C1-C6) alkylamino group, a phenyl group which may be substituted, a phenylcarbonyl group which may be substituted, a phenylamino group which may be substituted, and a heterocyclic group which may be substituted.

The "phenyl group which may be substituted" represents a phenyl group that may have one or more substituents, which may be the same as or different from one another, selected from the substituent group consisting of a halogen atom, a hydroxy group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a mono-(C1-C6) alkylamino group, a di-(C1-C6) alkylamino group, an acetylamino group, a phenyl group which may be substituted, a phenylcarbonyl group which may be substituted, a phenylamino group which may be substituted, and a heterocyclic group which may be substituted.

The "naphthyl group which may be substituted" represents a naphthyl group that may have one or more substituents, which may be the same as or different from one another, selected from the substituent group consisting of a halogen atom, a hydroxy group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a mono-(C1-C6) alkylamino group, a di-(C1-C6) alkylamino group, an acetylamino group, a phenyl group which may be substituted, a phenylcarbonyl group which may be substituted, a phenylamino group which may be substituted, and a heterocyclic group which may be substituted.

The "heterocyclic group which may be substituted" represents a heterocyclic group that may have one or more substituents, which may be the same as or different from one another, selected from the substituent group consisting of a halogen atom, a hydroxy group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a formyl group, a C2-C6 alkylcarbonyl group, a C2-C6 haloalkylcarbonyl group, a C2-C6 alkoxycarbonyl group, a C2-C6 haloalkoxycarbonyl group, a C2-C6 alkylcarbonyloxy group, a C2-C6 haloalkylcarbonyloxy group, an amino group, a mono-(C1-C6) alkylamino group, a di-(C1-C6) alkylamino group, an acetylamino group, a phenyl group which may be substituted, a phenylcarbonyl group which may be substituted, a phenylamino group which may be substituted, and a heterocyclic group which may be substituted.

Here, examples of the heterocyclic group include a pyridyl group, a pyridine-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrole group, a pyrazolyl group, and a tetrazolyl group.

The "C1-C3 alkyl group" represents a linear or branched alkyl group having from 1 to 3 carbon atoms such as a methyl group, an ethyl group, a n-propyl group, an isopropyl group, or a cyclopropyl group. The "C1-C4 alkyl group" represents, in addition to the "C1-C3 alkyl group", a linear or branched alkyl group having from 1 to 4 carbon atoms such as a n-butyl group, a 2-butyl group, an isobutyl group, or a t-butyl group. The "C1-C6 alkyl group" represents, in addition to the "C1-C4 alkyl group", a linear or branched alkyl group having from 1 to 6 carbon atoms such as a n-pentyl group, a 2-pentyl group, a 3-pentyl group, a neopentyl group, a n-hexyl group, a 2-hexyl group, a 4-methyl-2-pentyl group, or a 3-methyl-n-pentyl group.

The "C1-C3 haloalkyl group" represents a linear or branched alkyl group having from 1 to 3 carbon atoms that is substituted with one or more halogen atoms, which may be the same as or different from each other, such as a monofluoromethyl group, a difluoromethyl group, a trifluoromethyl group, a monochloromethyl group, a dichloromethyl group, a trichloromethyl group, a monobromomethyl group, a dibromomethyl group, a tribromomethyl group, a 1-fluoroethyl group, a 2-fluoroethyl group, a 2,2-difluoroethyl group, a 2,2,2-trifluoroethyl group, a 1-chloroethyl group, a 2-chloroethyl group, a 2,2-dichloroethyl group, a 2,2,2-trichloroethyl group, 1-bromoethyl group, 2-bromoethyl group, 2,2-dibromoethyl group, 2,2,2-tribromoethyl group, a 2-iodoethyl group, a pentafluoroethyl group, a 3-fluoro-n-propyl group, a 3-chloro-n-propyl group, a 3-bromo-n-propyl group, a 1,3-difluoro-2-propyl group, a 1,3-dichloro-2-propyl group, a 1,1,1-trifluoro-2-propyl group, a 1-chloro-3-fluoro-2-propyl group, a 1,1,1,3,3,3-hexafluoro-2-propyl group, a 1,1,1,3,3,3-hexafluoro-2-chloro-2-propyl group, a 2,2,3,3,3-pentafluoro-n-propyl group, a heptafluoroisopropyl group, or a heptafluoro-n-propyl group. The "C1-C4 haloalkyl group" represents, in addition to the "C1-C3 haloalkyl group", a linear or branched alkyl group having from 1 to 4 carbon atoms that is substituted with one or more halogen atoms, which may be the same as or different from each other, such as a 4-fluoro-n-butyl group, a nonafluoro-n-butyl group, or a nonafluoro-2-butyl group.

The "C2-C4 alkenyl group" represents an alkenyl group having from 2 to 4 carbon atoms that has a double bond in the carbon chain, such as a vinyl group, an allyl group, a 2-butenyl group, or a 3-butenyl group. The "C2-C4 haloalkenyl group" represents a linear or branched alkenyl group having from 2 to 4 carbon atoms that is substituted with one or more halogen atoms, which may be the same as or different from each other, and that has a double bond in the carbon chain, such as a 3,3-difluoro-2-propenyl group, a 3,3-dichloro-2-propenyl group, a 3,3-dibromo-2-propenyl group, a 2,3-dibromo-2-propenyl group, a 4,4-difluoro-3-butenyl group, or a 3,4,4-tribromo-3-butenyl group.

The "C2-C4 alkynyl group" represents a linear or branched alkynyl group having from 2 to 4 carbon atoms that has a triple bond in the carbon chain, such as a propargyl group, a 1-butyn-3-yl group, or a 1-butyn-3-methyl-3-yl group. The "C2-C4 haloalkynyl group" represents a linear or branched alkynyl group having from 2 to 4 carbon atoms that is substituted with one or more halogen atoms, which may be the same as or different from each other, and that has a triple bond in the carbon chain.

The "C3-C6 cycloalkyl group" represents, for example, a cycloalkyl group having from 3 to 6 carbon atoms that has a cyclic structure, such as a cyclopropyl group, a cyclobutyl group, a cyclopentyl group, a 2-methylcyclopentyl group, a 3-methylcyclopentyl group, or a cyclohexyl group. The "C3-C6 halocycloalkyl group" represents a cycloalkyl group having 3 to 6 carbon atoms that is substituted with one or more halogen atoms, which may be the same as or different from each other, and that has a cyclic structure, such as a 2,2,3,3-tetrafluorocyclobutyl group, a 2-chlorocyclohexyl group, a 4-chlorocyclohexyl group.

The "C1-C3 alkoxy group" represent a linear or branched alkoxy group having from 1 to 3 carbon atoms, such as a methoxy group, an ethoxy group, a n-propyloxy group, or an isopropyloxy group. The "C1-C6 alkoxy group" represents, in addition to the "C1-C3 alkoxy group", a linear or branched alkoxy group having from 1 to 6 carbon atoms, such as a n-butyloxy group, an isobutyloxy group, a 2-butyloxy group, a t-butyloxy group, a n-pentyloxy group, a neopentyloxy group, a n-hexyloxy group, an isohexyloxy group, a 3-methylpentyloxy group, a 2-methylpentyloxy group, a 2,3-dimethylbutyloxy group, or a 2,2-dimethylbutyloxy group.

The "C1-C3 haloalkoxy group" represents a linear or branched haloalkoxy group having from 1 to 3 carbon atoms that is substituted with one or more halogen atoms, which may be the same as or different from each other, such as a trifluoromethoxy group, a 2,2,2-trifluoroethoxy group, a 2-chloroethoxy group, a 1,1,1,3,3,3-hexafluoro-2-propyloxy group, or a 3-fluoro-n-propyloxy group. The "C1-C4 haloalkoxy group" represents, in addition to the "C1-C3 haloalkoxy group", a linear or branched haloalkoxy group having from 1 to 4 carbon atoms that is substituted with one or more halogen atoms, which may be the same as or different from each other, such as a 1,1,1,3,3,4,4,4-octafluoro-2-butyloxy group. The "C1-C6 haloalkoxy group" represents, in addition to the "C1-C4 haloalkoxy group", a linear or branched haloalkoxy group having from 1 to 6 carbon atoms that is substituted with one or more halogen atoms, which may be the same as or different from each other, such as a 1,1,1,2,2,4,4,5,5,5-decafluoro-3-pentyloxy group.

The "C1-C3 alkylthio group" represents a linear, branched, or cyclic alkylthio group having from 1 to 3 carbon atoms, such as a methylthio group, an ethylthio group, a n-propylthio group, an isopropylthio group, or a cyclopropylthio group.

The "C1-C4 alkylthio group" represents, in addition to the "C1-C3 alkylthio group", a linear, branched, or cyclic alkylthio group having from 1 to 4 carbon atoms, such as a n-butylthio group, an isobutylthio group, a 2-butylthio group, a t-butylthio group, or a cyclopropylmethylthio group. The "C1-C6 alkylthio group" represents, in addition to the "C1-C4 alkylthio group", a linear, branched, or cyclic alkylthio group having from 1 to 6 carbon atoms, such as a n-pentylthio group, an isopentylthio group, a neopentylthio group, a n-hexylthio group, an isohexylthio group, a 3-methylpentylthio group, a 2-methylpentylthio group, a 2,3-dimethylbutylthio group, or a 2,2-dimethylbutylthio group.

The "C1-C3 haloalkylthio group" represents a linear or branched alkylthio group having from 1 to 3 carbon atoms that is substituted with one or more halogen atoms, which may be the same as or different from each other, such as a trifluoromethylthio group, a pentafluoroethylthio group, a 2,2,2-trifluoroethylthio group, a heptafluoro-n-propylthio group, or a heptafluoro-isopropylthio group. The "C1-C4 haloalkylthio group" represents, in addition to the "C1-C3 haloalkylthio group", a linear or branched alkylthio group having from 1 to 4 carbon atoms that is substituted with one or more halogen atoms, which may be the same as or different from each other, such as a nonafluoro-n-butylthio group, a nonafluoro-2-butylthio group, or a 4,4,4-trifluoro-n-butylthio group. The "C1-C6 haloalkylthio group" represents, in addition to the "C1-C4 haloalkylthio group", a linear or branched alkylthio group having from 1 to 6 carbon atoms that is substituted with one or more halogen atoms, which may be the same as or different from each other, such as a undecafluoro-n-pentylthio group or a tridecafluoro-n-hexylthio group.

The "C1-C3 alkylsulfinyl group" represents a linear, branched, or cyclic alkylsulfinyl group having from 1 to 3 carbon atoms, such as a methylsulfinyl group, an ethylsulfinyl group, a n-propylsulfinyl group, an isopropylsulfinyl group, or a cyclopropylsulfinyl group. The "C1-C6 alkylsulfinyl group" represents, in addition to the"C1-C3 alkylsulfinyl group", a linear, branched, or cyclic alkylsulfinyl group having from 1 to 6 carbon atoms, such as a n-butylsulfinyl group, an isobutylsulfinyl group, a 2-butylsulfinyl group, a t-butylsulfinyl group, a cyclopropylmethylsulfinyl group, a n-pentylsulfinyl group, an isopentylsulfinyl group, a neopenylsulfinyl group, a n-hexylsulfinyl group, an isohexylsulfinyl group, a 3-methylpentylsulfinyl group, a 2-methylpentylsulfinyl group, a 2,3-dimethylbutylsulfinyl group, or a 2,2-dimethylbutylsulfinyl group.

The "C1-C3 haloalkylsulfinyl group" represents a linear or branched alkylsulfinyl group having from 1 to 3 carbon atoms that is substituted with one or more halogen atoms, which may be the same as or different from each other, such as a trifluoromethylsulfinyl group, a pentafluoroethylsulfinyl group, a 2,2,2-trifluoroethylsulfinyl group, a heptafluoro-n-propylsulfinyl group, a heptafluoro-isopropylsulfinyl group. The "C1-C6 haloalkylsulfinyl group" represents, in addition to the "C1-C3 haloalkylsulfinyl group", a linear or branched alkylsulfinyl group having from 1 to 6 carbon atoms that is substituted with one or more halogen atoms, which may be the same as or different from each other, such as a nonafluoro-n-butylsulfinyl group, a undecafluoro-n-pentylsulfinyl group, or a tridecafluoro-n-hexylsulfinyl group.

The "C1-C3 alkylsulfonyl group" represents a linear or branched alkylsulfonyl group having from 1 to 3 carbon atoms, such as a methylsulfonyl group, an ethylsulfonyl group, a n-propylsulfonyl group, an isopropylsulfonyl group, or a cyclopropylsulfonyl group. The "C1-C6 alkylsulfonyl group" represents, in addition to the "C1-C3 alkylsulfonyl group", a linear, branched, or cyclic alkylsulfonyl group having from 1 to 6 carbon atoms, such as a n-butylsulfonyl group, an isobutylsulfonyl group, a 2-butylsulfonyl group, a t-butylsulfonyl group, a cyclopropylmethylsulfonyl group, a n-pentylsulfonyl group, an isopentylsulfonyl group, a neopentylsulfonyl group, a n-hexylsulfonyl group, an isohexylsulfonyl group, a 3-methylpentylsulfonyl group, a 2-methylpentyisulfonyl group, a 2,3-dimethylbutylsulfonyl group, or a 2,2-dimethylbutylsulfonyl group.

The "C1-C3 haloalkylsulfonyl group" represents a linear or branched alkylsulfonyl group having from 1 to 3 carbon atoms that is substituted with one or more halogen atoms, which may be the same as or different from each other, such as a trifluoromethylsulfonyl group, pentafluoroethylsulfonyl group, a 2,2,2-trifluoroethylsulfonyl group, a heptafluoro-n-propylsulfonyl group, or a heptafluoro-isopropylsulfonyl group.

The "C1-C6 haloalkylsulfonyl group" represents, in addition to the "C1-C3 haloalkylsulfonyl group", a linear or branched alkylsulfonyl group having from 1 to 6 carbon atoms that is substituted with one or more halogen atoms, which may be the same as or different from each other, such as a nonafluoro-n-butylsulfonyl group, a undecafluoro-n-pentylsulfonyl group, or a tridecafluoro-n-hexylsulfonyl group.

The "mono-(C1-C4) alkylamino group" represents a linear, branched, or cyclic monoalkylamino group having from 1 to 4 carbon atoms, such as a methylamino group, an ethylamino group, a n-propylamino group, an isopropylamino group, a n-butylamino group, or a cyclopropylamino group. The "mono-(C1-C6) alkylamino group" represents, in addition to the "mono-(C1-C4) alkylamino group", a linear, branched, or cyclic monoalkylamino group having from 1 to 6 carbon atoms, such as a n-pentylamino group, a n-hexylamino group, an isohexylamino group, a cyclopentylamino group, or a cyclohexylamino group.

The "di-(C1-C4) alkylamino group" represents a dialkylamino group that has two linear or branched alkyl groups each having from 1 to 4 carbon atoms, which may be the same as or different from each other, such as a dimethylamino group, a diethylamine group, or an N-ethyl-N-methylamino group. The "di-(C1-C6) alkylamino group" represents, in addition to the "di-(C1-C4) alkylamino group", a dialkylamino group that has two linear or branched alkyl groups each having from 1 to 6 carbon atoms, which may be the same as or different from each other, such as an N-n-butyl-N-methylamino group, an N-n-butyl-N-ethylamino group, or an N-n-hexyl-N-n-pentylamino group.

The "C2-C4 alkylcarbonyl group" represents a linear, branched, or cyclic alkylcarbonyl group having from 2 to 4 carbon atoms, such as an acetyl group, a propionyl group, an isopropylcarbonyl group, or a cyclopropylcarbonyl group. The "C2-C6 alkylcarbonyl group" represents, in addition to the "C2-C4 alkylcarbonyl group", a linear, branched, or cyclic alkylcarbonyl group having from 2 to 6 carbon atoms, such as a n-butylcarbonyl group, a 2-butylcarbonyl group, a t-butylcarbonyl group, a n-pentylcarbonyl group, an isopentylcarbonyl group, a neopentylcarbonyl group, or a cyclopentylcarbonyl group.

The "C2-C6 haloalkylcarbonyl group" represents a linear or branched alkylcarbonyl group having from 2 to 6 carbon atoms that is substituted with one or more halogen atoms, which may be the same as or different from each other, such as a fluoroacetyl group, a difluoroacetyl group, a trifluoroacetyl group, a chloroacetyl group, a dichloroacetyl group, a trichloroacetyl group, a bromoacetyl group, a tribromoacetyl group, an iodoacetyl group, a triiodoacetyl group, a 3,3,3-trifluoropropionyl group, a 2,2,3,3,3-pentafluoropropionyl group, or a 2,2,3,3,4,4,4-heptafluorobutionyl group.

The "C2-C4 alkylcarbonyloxy group" represents a linear or branched alkylcarbonyloxy group having from 1 to 4 carbon atoms, such as an acetoxy group or a propionyloxy group. The "C2-C6 alkylcarbonyloxy group" represents, in addition to the "C2-C4 alkylcarbonyloxy group", a linear, branched, or cyclic alkylcarbonyloxy group having from 2 to 6 carbon atoms, such as a n-butylcarbonyloxy group, a 2-butylcarbonyloxy group, a t-butylcarbonyloxy group, a n-pentylcarbonyloxy group, a neopentylcarbonyloxy group, or a cyclopentylcarbonyloxy group.

The "C2-C6 haloalkylcarbonyloxy group" represent a linear or branched alkylcarbonyloxy group having from 2 to 6 carbon atoms that is substituted with one or more halogen atoms, which may be the same as or different from each other, such as a fluoroacetoxy group, a difluoroacetoxy group, a trifluoroacetoxy group, a chloroacetoxy group, a dichloroacetoxy group, a trichloroacetoxy group, a bromoacetoxy group, an iodoacetoxy group, a 3,3,3-trifluoropropionyloxy group, a 2,2,3,3,3-pentafluoropropionyloxy group, or a 2,2,3,3,4,4,4-heptafluorobutynyloxy group, The "C2-C4 alkoxycarbonyl group" represents a linear or branched alkoxycarbonyl group having from 1 to 4 carbon atoms, such as a methoxycarbonyl group, an ethoxycarbonyl group, or an isopropyloxycarbonyl group. The "C2-C6 alkoxycarbonyl group" represents, in addition to the "C2-C4 alkoxycarbonyl group", a linear, branched, or cyclic alkoxycarbonyl group having from 2 to 6 carbon atoms, such as n-butoxycarbonyl group, a 2-butoxycarbonyl group, a t-butoxycarbonyl group, a n-pentyloxycarbonyl group, a neopentyloxycarbonyl group, or a cyclopentylcarbonyl group.

The "C2-C6 haloalkoxycarbonyl group" represents a linear or branched alkoxycarbonyl group having from 2 to 6 carbon atoms that is substituted with one or more halogen atoms, which may be the same as or different from each other, such as a fluoromethoxycarbonyl group, a difluoromethoxycarbonyl group, a trifluoromethoxycarbonyl group, a chloromethoxycarbonyl group, a dichloromethoxycarbonyl group, a trichloromethoxycarbonyl group, a bromomethoxycarbonyl group, an iodomethoxycarbonyl group, a 3,3,3-trifluoropropyloxycarbonyl group, a 2,2,3,3,3-pentafluoropyloxycarbonyl group, a 2,2,3,3,4,4,4-heptafluorobutyloxycarbonyl group, or a 2,2,3,3,4,4,5,5,5-nonafluoropentyloxycarbonyl group.

The "C1-C4 perfluoroalkyl group" represents a linear or branched alkyl group having from 1 to 4 carbon atoms in which all hydrogen atoms are substituted with fluorine atoms, such as a trifluoromethyl group, a pentafluoroethyl group, a heptafluoro-n-propyl group, a heptafluoro-isopropyl group, a nonafluoro-n-butyl group, a nonafluoro-2-butyl group, or a nonafluoro-isobutyl group. The "C2-C6 perfluoroalkyl group" represents a linear or branched alkyl group having from 2 to 6 carbon atoms in which all hydrogen atoms are substituted with fluorine atoms, such as a pentafluoroethyl group, a heptafluoro-n-propyl group, a heptafluoro-isopropyl group, a nonafluoro-n-butyl group, a nonafluoro-2-butyl group, a nonafluoro-isobutyl group, a perfluoro-n-pentyl group, or a perfluoro-n-hexyl group.

The "C1-C6 perfluoroalkylthio group" represents a linear or branched alkylthio group having from 1 to 6 carbon atoms in which all hydrogen atoms are substituted with fluorine atoms, such as a trifluoromethylthio group, a pentafluoroethylthio group, a heptafluoro-n-propylthio group, a heptafluoro-isopropylthio group, a nonafluoro-n-butylthio group, a nonafluoro-2-butylthio group, a nonafluoro-isobutylthio group, a perfluoro-n-pentylthio group, or a perfluoro-n-hexylthio group.

The "C1-C6 perfluoroalkylsulfinyl group" represents a linear or branched alkylsulfinyl group having from 1 to 6 carbon atoms in which all hydrogen atoms are substituted with fluorine atoms, such as a trifluoromethylsulfinyl group, a pentafluoroethylsulfinyl group, a heptafluoro-n-propylsulfinyl group, a heptafluoro-isopropylsulfinyl group, a nonafluoro-n-butylsulfinyl group, a nonafluoro-2-butylsulfinyl group, a nonafluoro-isobutylsulfinyl group, a perfluoro-n-pentylsulfinyl group, or a perfluoro-n-hexylsulfinyl group.

The "C1-C6 perfluoroalkylsulfonyl group" represents a linear or branched alkylsulfonyl group having from 1 to 6 carbon atoms in which all hydrogen atoms are substituted with fluorine atoms, such as a trifluoromethylsulfonyl group, a pentafluoroethylsulfonyl group, a heptafluoro-n-propylsulfinyl group, a heptafluoro-isopropylsulfonyl group, a nonafluoro-n-butylsulfonyl group, a nonafluoro-2-butylsulfonyl group, a nonafluoro-isobutylsulfonyl group, a perfluoro-n-pentylsulfonyl group, or a perfluoro-n-hexylsulfonyl group.

The imide compound represented by Formula (1) according to the invention may include one or plural chiral carbon atoms or chiral centers in the structural formula, and thus two or more optical isomers may exist. The invention encompasses each of the optical isomers and a mixture thereof at any proportions. Further, the imide compound represented by Formula (1) according to the invention may include two or more kinds of geometrical isomers due to a carbon-carbon double bond in the structural formula. The invention encompasses each of the geometrical isomers and a mixture thereof at any proportions.

The preferable substituent or atom as the substituent or the like for the compound represented by Formula (1) or the like according to the invention are as follows.

With regard to $A_1$, $A_2$, $A_3$, and $A_4$, it is preferable that $A_1$ is a carbon atom, a nitrogen atom, or an oxidized nitrogen atom and all of $A_2$, $A_3$, and $A_4$ are carbon atoms, and it is more preferable that all of $A_1$, $A_2$, $A_3$, and $A_4$ are carbon atoms.

$R_1$ is preferably a hydrogen atom or a C1-C4 alkyl group, and more preferably a hydrogen atom, a methyl group, or an ethyl group.

With regard to $G_1$ and $G_2$, it is preferable that each of $G_1$ and $G_2$ is an oxygen atom or a sulfur atom, and it is more preferable that both $G_1$ and $G_2$ are oxygen atoms.

X is preferably a hydrogen atom or a halogen atom, and more preferably a hydrogen atom or a fluorine atom.

n is preferably 0, 1, or 2 when X is other than a hydrogen atom, and more preferably 0 or 1.

$X_1$ is preferably a hydrogen atom or a halogen atom, and more preferably a hydrogen atom or a fluorine atom.

$X_2$ is preferably a hydrogen atom or a fluorine atom, and more preferably a hydrogen atom.

$X_3$ and $X_4$ are preferably hydrogen atoms.

$Q_1$ is preferably a phenyl group that may have one or more substituents, which may be the same as or different from one another, selected from the substituent group consisting of a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a mono-(C1-C4) alkylamino group, a di-(C1-C4) alkylamino group, a cyano group, a nitro group, a hydroxy group, a C1-C4 alkylcarbonyl group, a C1-C4 alkylcarbonyloxy group, a C1-C4 alkoxycarbonyl group, an acetylamino group, and a phenyl group; or a pyridyl group that may have one or more substituents, which may be the same as or different from one another, selected from the substituent group consisting of a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a mono-(C1-C4) alkylamino group, a di-(C1-C4) alkylamino group, a cyano group, a nitro group, a hydroxy group, a C1-C4 alkylcarbonyl group, a C1-C4 alkylcarbonyloxy group, a C1-C4 alkoxycarbonyl group, an acetylamino group, and a phenyl group.

$Q_1$ is more preferably an unsubstituted phenyl group;

a substituted phenyl group that may have from 1 to 3 substituent(s), which may be the same as or different from one another, selected from the substituent group consisting of a fluorine atom, a chlorine atom, a bromine atom, an iodine atom, a methyl group, a trifluoromethyl group, a methoxy group, a trifluoromethoxy group, a methylthio group, a methylsulfinyl group, a methylsulfonyl group, a trifluoromethylthio group, a trifluoromethylsulfinyl group, a trifluoromethylsulfonyl group, a methylamino group, a dimethylamino group, a cyano group, and a nitro group;

an unsubstituted pyridyl group; or a substituted pyridyl group that may have 1 or 2 substituent(s), which may be the same as or different from each other, selected from the substituent group consisting of a fluorine atom, a chlorine atom, a bromine atom, an iodine atom, a methyl group, a trifluoromethyl group, a methoxy group, a trifluoromethoxy group, a methylthio group, a methylsulfinyl group, a methylsulfonyl group, a trifluoromethylthio group, a trifluoromethylsulfinyl group, a trifluoromethylsulfonyl group, a methylamino group, a dimethylamino group, a cyano group, and a nitro group.

$Q_2$ is preferably an substituted phenyl group represented by Formula (2) or an substituted pyridyl group represented by Formula (3).

Among these, it is preferable that each of $Y_1$ and $Y_5$ in Formula (2) independently represents a chlorine atom, a bromine atom, an iodine atom, a methyl group, an ethyl group, a n-propyl group, an isopropyl group, a n-butyl group, a 2-butyl group, a trifluoromethyl group, a methylthio group, a methylsulfinyl group, a methylsulfonyl group, a trifluoromethylthio group, a trifluoromethylsulfinyl group, a trifluoromethylsulfonyl group, or a cyano group.

In Formula (3), it is preferable that each of $Y_6$ and $Y_9$ independently represents chlorine atom, a bromine atom, an iodine atom, a methyl group, an ethyl group, a n-propyl group, an isopropyl group, a n-butyl group, a 2-butyl group, a trifluoromethyl group, a methylthio group, a methylsulfinyl group, a methylsulfonyl group, a trifluoromethylthio group, a trifluoromethylsulfinyl group, a trifluoromethylsulfonyl group, or a cyano group.

Each of $Y_2$, $Y_4$, and $Y_7$ is preferably a hydrogen atom, a halogen atom, or a methyl group, and more preferably a hydrogen atom.

$Y_3$ is preferably a pentafluoroethyl group, a heptafluoro-n-propyl group, a heptafluoro-isopropyl group, a nonafluoro-n-butyl group, a nonafluoro-2-butyl group, a nonafluoro-isobutyl group, a trifluoromethylthio group, a pentafluoroethylthio group, a heptafluoro-n-propylthio group, a heptafluoro-isopropylthio group, a nonafluoro-n-butylthio group, a nonafluoro-2-butylthio group, a trifluoromethylsulfinyl group, a pentafluoroethylsulfinyl group, a heptafluoro-n-propylsulfinyl group, a heptafluoro-isopropylsulfinyl group, a nonafluoro-n-butylsulfinyl group, a nonafluoro-2-butylsulfinyl group, a trifluoromethylsulfonyl group, pentafluoroethylsulfonyl group, a heptafluoro-n-propylsulfonyl group, a heptafluoro-isopropylsulfonyl group, a nonafluoro-n-butylsulfonyl group, or a nonafluoro-2-butylsulfonyl group.

$Y_8$ is preferably a pentafluoroethyl group, a heptafluoro-n-propyl group, a heptafluoro-isopropyl group, a nonafluoro-n-butyl group, a nonafluoro-2-butyl group, a nonafluoro-isobutyl group, a trifluoromethylthio group, a pentafluoroethylthio group, a heptafluoro-n-propylthio group, a heptafluoro-isopropylthio group, a nonafluoro-n-butylthio group, a nonafluoro-2-butylthio group, a trifluoromethylsulfinyl group, a pentafluoroethylsulfinyl group, a heptafluoro-n-propylsulfinyl group, a heptafluoro-isopropylsulfinyl group, a nonafluoro-n-butylsulfinyl group, a nonafluoro-2-butylsulfinyl group, a trifluoromethylsulfinyl group, pentafluoroethylsulfonyl group, a heptafluoro-n-propylsulfonyl group, a heptafluoro-isopropylsulfonyl group, a nonafluoro-n-butylsulfonyl group, a nonafluoro-2-butylsulfonyl group, a pentafluoroethoxy group, or a 1,1,1,3,3,3-hexafluoro-isopropyloxy group.

The representative method for manufacturing the compound according to the invention are shown below. The compound according to the invention can be manufactured in accordance with the method, but the manufacturing method and the pathway are not limited to the manufacturing method described below.

In the following reaction formula, each $A_1$, $A_2$, $A_3$, and $A_4$ represents a carbon atom, a nitrogen atom, or an oxidized nitrogen atom; $R_1$ represents a hydrogen atom, a C1-C4 alkyl group which may be substituted, or a C2-C4 alkylcarbonyl group which may be substituted. Each of $G_1$ and $G_2$ independently represents an oxygen atom or a sulfur atom; X represents a hydrogen atom, a halogen atom, C1-C3 alkyl group, or a trifluoromethyl group, and when there are two or more X's, each X may be the same as or different from one another. n represents an integer of from 0 to 4. $Q_1$ represents a phenyl group which may be substituted, a naphthyl group which may be substituted, or a heterocyclic group which may be substituted. $Q_2$ represents a phenyl group or a heterocyclic group, each of which has one or more substituents, in which at least one of the one or more substituents represents a C1-C4 haloalkoxy group, a C2-C6 perfluoroalkyl group, a C1-C6 perfluoroalkylthio group, a C1-C6 perfluoroalkylsulfinyl group, or a C1-C6 perfluoroalkylsulfonyl group. Hal represents a chlorine atom or a bromine atom.

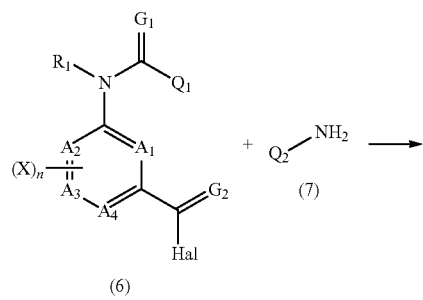

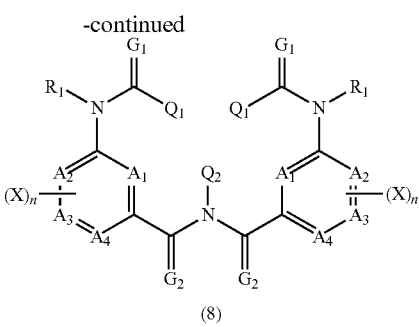

Formula (6)+Formula (7)→Formula (8)

The aromatic imide derivative represented by Formula (8) can be manufactured by reacting the aromatic carboxylic halide derivative represented by Formula (6) with the aromatic amine derivative represented by Formula (7) in an appropriate solvent or in the absence of a solvent.

The solvent may be any of those which does not interfere with the progress of the reaction, and examples thereof include water; aromatic hydrocarbons such as benzene, toluene, or xylene; halogenated hydrocarbons such as dichloromethane, chloroform, or carbon tetrachloride; chained or cyclic ethers such as diethyl ether, dioxane, tetrahydrofuran, or 1,2-dimethoxy ethane; esters such as ethyl acetate or butyl acetate; alcohols such as methanol or ethanol; ketones such as acetone, methyl isobutyl ketone, or cyclohexanone; amides such as dimethylformamide or dimethylacetamide; nitriles such as acetonitrile; and inert solvents such as 1,3-dimethyl-2-imidazolidinone. These solvents may be used singly, or in combination of two or more kinds thereof.

In this process, a suitable base may be used. Examples of the base include organic bases such as triethylamine, tri-n-butyl amine, pyridine, or 4-dimethylamino pyridine; alkali metal hydroxides such as sodium hydroxide or potassium hydroxide; carbonates such as sodium hydrogen carbonate or potassium carbonate; phosphates such as dipotassium monohydrogen phosphate or tri sodium phosphate; alkali metal hydride salts such as sodium hydride; and alkali metal alcoholates such as sodium methoxide or sodium ethoxide. These bases may be appropriately used in an amount in the range from 0.01-fold molar equivalent to 5-fold molar equivalents with respect to the compound represented by Formula (6).

The reaction temperature may be appropriately selected from −20° C. to the reflux temperature of the solvent used. The reaction time may be appropriately selected within the range from several minutes to 96 hours.

The aromatic carboxylic halide derivative represented by Formula (6) can be manufactured easily by a conventional method using a halogenating agent from an aromatic carboxylic acid. Examples of the halogenating agent include thionyl chloride, thionyl bromide, phosphorus oxychloride, oxalyl chloride, and phosphorus trichloride.

Meanwhile, it is possible to manufacture the compound represented by Formula (8) from the aromatic carboxylic acid derivative and the compound represented by Formula (7) without using a halogenating agent. Examples of the method include a method using a condensing agent, in which N,N'-dicyclohexylcarbodiimide is appropriately used with an additive such as 1-hydroxybenzotriazole, in accordance with a method described, for example, in Chem. Ber. p. 788 (1970). Other condensing agents that can be used in this method may be 1-ethyl-3-(3-dimethylaminopropyl)carbodiimide, 1,1'-carbonylbis-1H-imidazole, or the like.

Examples of the method of manufacturing the compound represented by Formula (8) further include a mixed anhydride method using a chloroformic acid ester. For example, it is possible to manufacture the compound represented by Formula (8) from the aromatic carboxylic acid derivative and the compound represented by Formula (7) in accordance with a method described in J. Am. Chem, Soc., p. 5012 (1967). Examples of the chloroformic acid ester used in this method include isobutyl chloroformate, isopropyl chloroformate and the like. Other than the chloroformic acid ester, diethylacetyl chloride, trimethylacetyl chloride, or the like may also be used, With regard to both the method using a condensing agent and the mixed anhydride method, the solvent, the reaction temperature, and the reaction time are not limited to those described in the literature above. An inert solvent that does not significantly inhibit the progress of the reaction may be appropriately used, and the reaction temperature and the reaction time may also be selected appropriately according to the progress of the reaction.

In the manufacture methods described above, a product of interest may be isolated from the reaction system after the reaction is completed according to a conventional method, and purification may be carried out by a operation such as recrystallization, column chromatography, or distillation, if necessary.

Hereinbelow, examples of the representative compounds of the imide compound represented by Formula (1) as an active ingredient for the insecticide according to the invention are shown in Tables 1 to 6, but the invention is not limited thereto.

In the tables, "n-" represents normal, "Me" represents a methyl group, "Et" represents an ethyl group, "H" represents a hydrogen atom, "O" represents an oxygen atom, "S" represents a sulfur atom, "C" represents a carbon atom, "N" represents a nitrogen atom, "F" represents a fluorine atom, "Cl" represents a chlorine atom, "Br" represents a bromine atom, "I" represents an iodine atom, and "CF3" represents a trifluoromethyl group.

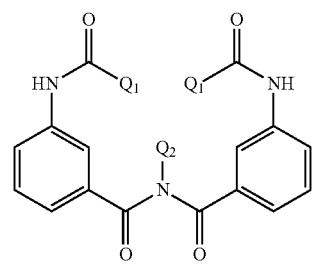

TABLE 1

| Compound No. | $Q_1$ | $Q_2$ |
|---|---|---|
| 1 | phenyl | 2,6-dimethyl-4-(pentafluoroethyl)phenyl |
| 2 | phenyl | 2,6-dichloro-4-(pentafluoroethyl)phenyl |
| 3 | 2-fluorophenyl | 2,6-dichloro-4-(pentafluoroethyl)phenyl |
| 4 | phenyl | 2,6-dibromo-4-(pentafluoroethyl)phenyl |
| 5 | 2-fluorophenyl | 2,6-dibromo-4-(pentafluoroethyl)phenyl |
| 6 | phenyl | 2,6-dichloro-4-(heptafluoroisopropyl)phenyl |
| 7 | phenyl | 2,6-dibromo-4-(heptafluoroisopropyl)phenyl |
| 8 | 2-fluorophenyl | 2,6-dibromo-4-(heptafluoroisopropyl)phenyl |
| 9 | phenyl | 2,6-dimethyl-4-(heptafluoro-n-propyl)phenyl |
| 10 | phenyl | 2,6-dimethyl-4-(heptafluoroisopropyl)phenyl |
| 11 | 2-methylphenyl | 2,6-dimethyl-4-(heptafluoroisopropyl)phenyl |
| 12 | 3-methylphenyl | 2,6-dimethyl-4-(heptafluoroisopropyl)phenyl |
| 13 | 4-methylphenyl | 2,6-dimethyl-4-(heptafluoroisopropyl)phenyl |
| 14 | 2-ethylphenyl | 2,6-dimethyl-4-(heptafluoroisopropyl)phenyl |
| 15 | 3-ethylphenyl | 2,6-dimethyl-4-(heptafluoroisopropyl)phenyl |
| 16 | 4-ethylphenyl | 2,6-dimethyl-4-(heptafluoroisopropyl)phenyl |
| 17 | 2-fluorophenyl | 2,6-dimethyl-4-(heptafluoroisopropyl)phenyl |
| 18 | 3-fluorophenyl | 2,6-dimethyl-4-(heptafluoroisopropyl)phenyl |
| 19 | 4-fluorophenyl | 2,6-dimethyl-4-(heptafluoroisopropyl)phenyl |
| 20 | 2-chlorophenyl | 2,6-dimethyl-4-(heptafluoroisopropyl)phenyl |
| 21 | 3-chlorophenyl | 2,6-dimethyl-4-(heptafluoroisopropyl)phenyl |
| 22 | 4-chlorophenyl | 2,6-dimethyl-4-(heptafluoroisopropyl)phenyl |
| 23 | 2-bromophenyl | 2,6-dimethyl-4-(heptafluoroisopropyl)phenyl |
| 24 | 3-bromophenyl | 2,6-dimethyl-4-(heptafluoroisopropyl)phenyl |
| 25 | 4-bromophenyl | 2,6-dimethyl-4-(heptafluoroisopropyl)phenyl |
| 26 | 2-iodophenyl | 2,6-dimethyl-4-(heptafluoroisopropyl)phenyl |
| 27 | 3-iodophenyl | 2,6-dimethyl-4-(heptafluoroisopropyl)phenyl |
| 28 | 4-iodophenyl | 2,6-dimethyl-4-(heptafluoroisopropyl)phenyl |
| 29 | 3-cyanophenyl | 2,6-dimethyl-4-(heptatluoroisopropyl)phenyl |
| 30 | 4-cyanophenyl | 2,6-dimethyl-4-(heptafluoroisopropyl)phenyl |
| 31 | 2-nitrophenyl | 2,6-dimethyl-4-(heptafluoroisopropyl)phenyl |
| 32 | 3-nitrophenyl | 2,6-dimethyl-4-(heptafluoroisopropyl)phenyl |
| 33 | 4-nitrophenyl | 2,6-dimethyl-4-(heptafluoroisopropyl)phenyl |
| 34 | 2-aminophenyl | 2,6-dimethyl-4-(heptafluoroisopropyl)phenyl |
| 35 | 3-aminophenyl | 2,6-dimethyl-4-(heptafluoroisopropyl)phenyl |
| 36 | 4-aminophenyl | 2,6-dimethyl-4-(heptafluoroisopropyl)phenyl |
| 37 | 2-trifluoromethylphenyl | 2,6-dimethyl-4-(heptafluoroisopropyl)phenyl |
| 38 | 3-trifluoromethylphenyl | 2,6-dimethyl-4-(heptafluoroisopropyl)phenyl |
| 39 | 4-trifluoromethylphenyl | 2,6-dimethyl-4-(heptafluoroisopropyl)phenyl |
| 40 | 2-hydroxyphenyl | 2,6-dimethyl-4-(heptafluoroisopropyl)phenyl |
| 41 | 2-methoxyphenyl | 2,6-dimethyl-4-(heptafluoroisopropyl)phenyl |
| 42 | 3-methoxyphenyl | 2,6-dimethyl-4-(heptafluoroisopropyl)phenyl |
| 43 | 4-methoxyphenyl | 2,6-dimethyl-4-(heptafluoroisopropyl)phenyl |

TABLE 1-continued

| Compound No. | Q₁ | Q₂ |
|---|---|---|
| 44 | 2-phenoxyphenyl | 2,6-dimethyl-4-(heptafluoroisopropyl)phenyl |
| 45 | 4-(1,1-dimethylethyl)phenyl | 2,6-dimethyl-4-(heptafluoroisopropyl)phenyl |
| 46 | 3-(dimethylamino)phenyl | 2,6-dimethyl-4-(heptafluoroisopropyl)phenyl |
| 47 | 4-(dimethylamino)phenyl | 2,6-dimethyl-4-(heptafluoroisopropyl)phenyl |
| 48 | 4-trifluoromethoxyphenyl | 2,6-dimethyl-4-(heptafluoroisopropyl)phenyl |
| 49 | 2-(acetylamino)phenyl | 2,6-dimethyl-4-(heptafluoroisopropyl)phenyl |
| 50 | 3-(acetylamino)phenyl | 2,6-dimethyl-4-(heptafluoroisopropyl)phenyl |
| 51 | 4-(acetylamino)phenyl | 2,6-dimethyl-4-(heptafluoroisopropyl)phenyl |
| 52 | 2-acetoxyphenyl | 2,6-dimethyl-4-(heptafluoroisopropyl)phenyl |
| 53 | 2-(methoxycarbonyl)phenyl | 2,6-dimethyl-4-(heptafluoroisopropyl)phenyl |
| 54 | 4-(methoxycarbonyl)phenyl | 2,6-dimethyl-4-(heptafluoroisopropyl)phenyl |
| 55 | 2-(4-triflioromethylphenyl)phenyl | 2,6-dimethyl-4-(heptafluoroisopropyl)phenyl |
| 56 | 2,3-dimethylphenyl | 2,6-dimethyl-4-(heptafluoroisopropyl)phenyl |
| 57 | 2,4-dimethylphenyl | 2,6-dimethyl-4-(heptafluoroisopropyl)phenyl |
| 58 | 2,6-dimethylphenyl | 2,6-dimethyl-4-(heptafluoroisopropyl)phenyl |
| 59 | 2,3-difluorophenyl | 2,6-dimethyl-4-(heptafluoroisopropyl)phenyl |
| 60 | 2,4-difluorophenyl | 2,6-dimethyl-4-(heptafluoroisopropyl)phenyl |
| 61 | 2,5-difluorophenyl | 2,6-dimethyl-4-(heptafluoroisopropyl)phenyl |
| 62 | 2,6-difluorophenyl | 2,6-dimethyl-4-(heptafluoroisopropyl)phenyl |
| 63 | 3,4-difluorophenyl | 2,6-dimethyl-4-(heptafluoroisopropyl)phenyl |
| 64 | 3,5-difluorophenyl | 2,6-dimethyl-4-(heptafluoroisopropyl)phenyl |
| 65 | 2,3-dichlorophenyl | 2,6-dimethyl-4-(heptafluoroisopropyl)phenyl |
| 66 | 2,4-dichlorophenyl | 2,6-dimethyl-4-(heptafluoroisopropyl)phenyl |
| 67 | 2,5-dichlorophenyl | 2,6-dimethyl-4-(heptafluoroisopropyl)phenyl |
| 68 | 2,6-dichlorophenyl | 2,6-dimethyl-4-(heptafluoroisopropyl)phenyl |
| 69 | 3,4-dichlorophenyl | 2,6-dimethyl-4-(heptafluoroisopropyl)phenyl |
| 70 | 2,4-dinitrophenyl | 2,6-dimethyl-4-(heptafluoroisopropyl)phenyl |
| 71 | 3,4-dinitrophenyl | 2,6-dimethyl-4-(heptafluoroisopropyl)phenyl |
| 72 | 2,6-dimethoxyphenyl | 2,6-dimethyl-4-(heptafluoroisopropyl)phenyl |
| 73 | 3,5-dimethoxyphenyl | 2,6-dimethyl-4-(heptafluoroisopropyl)phenyl |
| 74 | 3-methyl-4-nitrophenyl | 2,6-dimethyl-4-(heptafluoroisopropyl)phenyl |
| 75 | 5-amino-2-fluorophenyl | 2,6-dimethyl-4-(heptafluoroisopropyl)phenyl |
| 76 | 3-fluoro-2-methylphenyl | 2,6-dimethyl-4-(heptafluoroisopropyl)phenyl |
| 77 | 2-fluoro-5-nitrophenyl | 2,6-dimethyl-4-(heptafluoroisopropyl)phenyl |
| 78 | 4-fluoro-3-nitrophenyl | 2,6-dimethyl-4-(heptafluoroisopropyl)phenyl |
| 79 | 5-fluoro-2-nitrophenyl | 2,6-dimethyl-4-(heptafluoroisopropyl)phenyl |
| 80 | 2-fluoro-6-iodophenyl | 2,6-dimethyl-4-(heptafluoroisopropyl)phenyl |
| 81 | 2-fluoro-5-trifluoromethylphenyl | 2,6-dimethyl-4-(heptafluoroisopropyl)phenyl |
| 82 | 2-chloro-4-nitrophenyl | 2,6-dimethyl-4-(heptafluoroisopropyl)phenyl |
| 83 | 2-chloro-4-fluorophenyl | 2,6-dimethyl-4-(heptafluoroisopropyl)phenyl |
| 84 | 2-chloro-6-fluorophenyl | 2,6-dimethyl-4-(heptafluoroisopropyl)phenyl |
| 85 | 3-chloro-4-fluorophenyl | 2,6-dimethyl-4-(heptafluoroisopropyl)phenyl |
| 86 | 4-chloro-2-fluorophenyl | 2,6-dimethyl-4-(heptafluoroisopropyl)phenyl |
| 87 | 4-chloro-2-nitrophenyl | 2,6-dimethyl-4-(heptafluoroisopropyl)phenyl |
| 88 | 3-methoxy-4-nitrophenyl | 2,6-dimethyl-4-(heptafluoroisopropyl)phenyl |
| 89 | 2-methoxy-4-nitrophenyl | 2,6-dimethyl-4-(heptafluoroisopropyl)phenyl |
| 90 | 2,3,4-trifluorophenyl | 2,6-dimethyl-4-(heptafluoroisopropyl)phenyl |
| 91 | 2,4,6-trimethylphenyl | 2,6-dimethyl-4-(heptafluoroisopropyl)phenyl |
| 92 | 2,3,6-trifluorophenyl | 2,6-dimethyl-4-(heptafluoroisopropyl)phenyl |
| 93 | 2,4,5-trimethoxylphenyl | 2,6-dimethyl-4-(heptafluoroisopropyl)phenyl |
| 94 | 3,4,5-trimethoxylphenyl | 2,6-dimethyl-4-(heptafluoroisopropyl)phenyl |
| 95 | 2,3,4,5,6-pentafluorophenyl | 2,6-dimethyl-4-(heptafluoroisopropyl)phenyl |
| 96 | 2-biphenyl | 2,6-dimethyl-4-(heptafluoroisopropyl)phenyl |
| 97 | 3-biphenyl | 2,6-dimethyl-4-(heptafluoroisopropyl)phenyl |
| 98 | 1-naphthyl | 2,6-dimethyl-4-(heptafluoroisopropyl)phenyl |
| 99 | 2-naphthyl | 2,6-dimethyl-4-(heptafluoroisopropyl)phenyl |
| 100 | pyridin-2-yl | 2,6-dimethyl-4-(heptafluoroisopropyl)phenyl |
| 101 | pyridin-3-yl | 2,6-dimethyl-4-(heptafluoroisopropyl)phenyl |
| 102 | pyridin-4-yl | 2,6-dimethyl-4-(heptafluoroisopropyl)phenyl |
| 103 | 2-methylpyridin-5-yl | 2,6-dimethyl-4-(heptafluoroisopropyl)phenyl |
| 104 | 3-methylpyridin-2-yl | 2,6-dimethyl-4-(heptafluoroisopropyl)phenyl |
| 105 | 2-fluoropyridin-3-yl | 2,6-dimethyl-4-(heptafluoroisopropyl)phenyl |
| 106 | 2-chloropyridin-3-yl | 2,6-dimethyl-4-(heptafluoroisopropyl)phenyl |
| 107 | 2-chloropyridin-4-yl | 2,6-dimethyl-4-(heptafluoroisopropyl)phenyl |
| 108 | 2-chloropyridin-6-yl | 2,6-dimethyl-4-(heptafluoroisopropyl)phenyl |
| 109 | 2-chloropyridin-5-yl | 2,6-dimethyl-4-(heptafluoroisopropyl)phenyl |
| 110 | 5-chloropyridin-2-yl | 2,6-dimethyl-4-(heptafluoroisopropyl)phenyl |
| 111 | 4-trifluoromethylpyridin-3-yl | 2,6-dimethyl-4-(heptafluoroisopropyl)phenyl |
| 112 | 3-hydroxypyridin-2-yl | 2,6-dimethyl-4-(heptafluoroisopropyl)phenyl |
| 113 | 2-phenoxypyridin-3-yl | 2,6-dimethyl-4-(heptafluoroisopropyl)phenyl |
| 114 | 2-methylthiopyridin-3-yl | 2,6-dimethyl-4-(heptafluoroisopropyl)phenyl |
| 115 | 2,6-dimethoxypyridin-3-yl | 2,6-dimethyl-4-(heptafluoroisopropyl)phenyl |
| 116 | 2,3-dichloropyridin-5-yl | 2,6-dimethyl-4-(heptafluoroisopropyl)phenyl |
| 117 | 2,5-dichloropyridin-3-yl | 2,6-dimethyl-4-(heptafluoroisopropyl)phenyl |
| 118 | 2,6-dichloropyridin-3-yl | 2,6-dimethyl-4-(heptafluoroisopropyl)phenyl |
| 119 | 3,5-dichloropyridin-4-yl | 2,6-dimethyl-4-(heptafluoroisopropyl)phenyl |

TABLE 1-continued

| Compound No. | $Q_1$ | $Q_2$ |
|---|---|---|
| 120 | (pyridine-N-oxide)-2-yl | 2,6-dimethyl-4-(heptafluoroisopropyl)phenyl |
| 121 | N-methylpyrrol-2-yl | 2,6-dimethyl-4-(heptafluoroisopropyl)phenyl |
| 122 | pyrazin-2-yl | 2,6-dimethyl-4-(heptafluoroisopropyl)phenyl |
| 123 | 2-methylpyrazin-5-yl | 2,6-dimethyl-4-(heptafluoroisopropyl)phenyl |
| 124 | 4-trifluoromethylpyrimidin-5-yl | 2,6-dimethyl-4-(heptafluoroisopropyl)phenyl |
| 125 | furan-2-yl | 2,6-dimethyl-4-(heptafluoroisopropyl)phenyl |
| 126 | furan-3-yl | 2,6-dimethyl-4-(heptafluoroisopropyl)phenyl |
| 127 | 2-tetrahydrofuranyl | 2,6-dimethyl-4-(heptafluoroisopropyl)phenyl |
| 128 | 3-tetrahydrofuranyl | 2,6-dimethyl-4-(heptafluoroisopropyl)phenyl |
| 129 | benzofuran-2-yl | 2,6-dimethyl-4-(heptafluoroisopropyl)phenyl |
| 130 | tetrahydropyran-2-yl | 2,6-dimethyl-4-(heptafluoroisopropyl)phenyl |
| 131 | 2-methyl-5,6-dihydro-4H-pyran-3-yl | 2,6-dimethyl-4-(heptafluoroisopropyl)phenyl |
| 132 | thiophen-2-yl | 2,6-dimethyl-4-(heptafluoroisopropyl)phenyl |
| 133 | thiophen-3-yl | 2,6-dimethyl-4-(heptafluoroisopropyl)phenyl |
| 134 | 3-methylthiophen-2-yl | 2,6-dimethyl-4-(heptafluoroisopropyl)phenyl |
| 135 | 2-nitrothiophen-4-yl | 2,6-dimethyl-4-(heptafluoroisopropyl)phenyl |
| 136 | 2-methylthiophen-5-yl | 2,6-dimethyl-4-(heptafluoroisopropyl)phenyl |
| 137 | 3-chlorothiophen-2-yl | 2,6-dimethyl-4-(heptafluoroisopropyl)phenyl |
| 138 | 2-chlorothiophen-5-yl | 2,6-dimethyl-4-(heptafluoroisopropyl)phenyl |
| 139 | 3-bromothiophen-2-yl | 2,6-dimethyl-4-(heptafluoroisopropyl)phenyl |
| 140 | 2-bromothiophen-5-yl | 2,6-dimethyl-4-(heptafluoroisopropyl)phenyl |
| 141 | 3-iodothiophen-2-yl | 2,6-dimethyl-4-(heptafluoroisopropyl)phenyl |
| 142 | 3-phenylthiophen-2-yl | 2,6-dimethyl-4-(heptafluoroisopropyl)phenyl |
| 143 | 2,4-dimethylthiophen-5-yl | 2,6-dimethyl-4-(heptafluoroisopropyl)phenyl |
| 144 | benzothiophen-2-yl | 2,6-dimethyl-4-(heptafluoroisopropyl)phenyl |
| 145 | 4-nitro-1H-pyrrol-2-yl | 2,6-dimethyl-4-(heptafluoroisopropyl)phenyl |
| 146 | 3-ethyl-3H-pyrazol-4-yl | 2,6-dimethyl-4-(heptafluoroisopropyl)phenyl |
| 147 | 1-methyl-3-nitro-1H-pyrazol-4-yl | 2,6-dimethyl-4-(heptafluoroisopropyl)phenyl |
| 148 | 3-chloro-1-methyl-1H-pyrazol-4-yl | 2,6-dimethyl-4-(heptafluoroisopropyl)phenyl |
| 149 | 3-bromo-1-methyl-1H-pyrazol-4-yl | 2,6-dimethyl-4-(heptafluoroisopropyl)phenyl |
| 150 | 1-methyl-3-trifluoromethyl-1H-pyrazol-4-yl | 2,6-dimethyl-4-(heptafluoroisopropyl)phenyl |
| 151 | 1-methyl-5-trifluoromethyl-1H-pyrazol-4-yl | 2,6-dimethyl-4-(heptafluoroisopropyl)phenyl |
| 152 | isooxazol-5-yl | 2,6-dimethyl-4-(heptafluoroisopropyl)phenyl |
| 153 | 4-trifluoromethylthiazol-5-yl | 2,6-dimethyl-4-(heptafluoroisopropyl)phenyl |
| 154 | 2,4-dimethylthiazol-5-yl | 2,6-dimethyl-4-(heptafluoroisopropyl)phenyl |
| 155 | 2-ethyl-4-methyl-thiazol-5-yl | 2,6-dimethyl-4-(heptafluoroisopropyl)phenyl |
| 156 | 2-chloro-4-methyl-thiazol-5-yl | 2,6-dimethyl-4-(heptafluoroisopropyl)phenyl |
| 157 | 3-methyl-isothiazol-5-yl | 2,6-dimethyl-4-(heptafluoroisopropyl)phenyl |
| 158 | 3,4-dichloro-isothiazol-5-yl | 2,6-dimethyl-4-(heptafluoroisopropyl)phenyl |
| 159 | 3-chlorobenzothiazol-2-yl | 2,6-dimethyl-4-(heptafluoroisopropyl)phenyl |
| 160 | 2,2-difluorobenz[1.3]dioxol-5-yl | 2,6-dimethyl-4-(heptafluoroisopropyl)phenyl |
| 161 | 2,2-difluorobenz[1.3]dioxol-4-yl | 2,6-dimethyl-4-(heptafluoroisopropyl)phenyl |
| 162 | 2-phenylquinolin-4-yl | 2,6-dimethyl-4-(heptafluoroisopropyl)phenyl |
| 163 | phenyl | 2-bromo-4-(heptafluoroisopropyl)-6-methylphenyl |
| 164 | phenyl | 2-ethyl-4-(heptafluoroisopropyl)-6-methylphenyl |
| 165 | 2-fluorophenyl | 2-ethyl-4-(heptafluoroisopropyl)-6-methylphenyl |
| 166 | phenyl | 4-(heptafluoroisopropyl)-2-iodo-6-methylphenyl |
| 167 | phenyl | 4-(heptafluoroisopropyl)-2-hydroxy-6-methylphenyl |
| 168 | phenyl | 2-chloro-6-ethyl-4-(heptafluoroisopropyl)phenyl |
| 169 | phenyl | 2-bromo-6-ethyl-4-(heptafluoroisopropyl)phenyl |
| 170 | 2-fluorophenyl | 2-bromo-6-ethyl-4-(heptafluoroisopropyl)phenyl |
| 171 | phenyl | 2-ethyl-4-(heptafluoroisopropyl)-6-iodophenyl |
| 172 | 2-fluorophenyl | 2-ethyl-4-(heptafluoroisopropyl)-6-iodophenyl |
| 173 | 4-nitrophenyl | 2-ethyl-4-(heptafluoroisopropyl)-6-iodophenyl |
| 174 | 4-cyanophenyl | 2-ethyl-4-(heptafluoroisopropyl)-6-iodophenyl |
| 175 | 4-nitrophenyl | 4-(heptafluoroisopropyl)-2-methyl-6-n-propylphenyl |
| 176 | phenyl | 4-(heptafluoroisopropyl)-2-isopropyl-6-methylphenyl |
| 177 | 2-fluorophenyl | 4-(heptafluoroisopropyl)-2-isopropyl-6-methylphenyl |
| 178 | phenyl | 2-bromo-4-(heptafluoroisopropyl)-6-n-propylphenyl |
| 179 | 2-fluorophenyl | 2-bromo-4-(heptafluoroisopropyl)-6-n-propylphenyl |
| 180 | 4-nitrophenyl | 2-bromo-4-(heptafluoroisopropyl)-6-n-propylphenyl |

TABLE 1-continued

| Compound No. | Q₁ | Q₂ |
|---|---|---|
| 181 | 4-cyanophenyl | 2-bromo-4-(heptafluoroisopropyl)-6-n-propylphenyl |
| 182 | phenyl | 4-(heptafluoroisopropyl)-2-iodo-6-n-propylphenyl |
| 183 | 2-fluorophenyl | 4-(heptafluoroisopropyl)-2-iodo-6-n-propylphenyl |
| 184 | 4-nitrophenyl | 4-(heptafluoroisopropyl)-2-iodo-6-n-propylphenyl |
| 185 | 4-cyanophenyl | 4-(heptafluoroisopropyl)-2-iodo-6-n-propylphenyl |
| 186 | 4-trifluoromethylphenyl | 4-(heptafluoroisopropyl)-2-iodo-6-n-propylphenyl |
| 187 | phenyl | 2-chloro-4-(heptafluoroisopropyl)-6-n-butylphenyl |
| 188 | 2-fluorophenyl | 2-chloro-4-(heptafluoroisopropyl)-6-n-butylphenyl |
| 189 | phenyl | 2-bromo-4-(heptafluoroisopropyl)-6-n-butylphenyl |
| 190 | 2-fluorophenyl | 2-bromo-4-(heptafluoroisopropyl)-6-n-butylphenyl |
| 191 | phenyl | 4-(heptafluoroisopropyl)-2-iodo-6-n-buthylphenyl |
| 192 | 2-fluorophenyl | 4-(heptafluoroisopropyl)-2-iodo-6-n-buthylphenyl |
| 193 | phenyl | 2-(2-butyl)-6-chloro-4-(heptafluoroisopropyl)phenyl |
| 194 | phenyl | 2-bromo-6-(2-butyl)-4-(heptafluoroisopropyl)phenyl |
| 195 | 2-fluorophenyl | 2-bromo-6-(2-butyl)-4-(heptafluoroisopropyl)phenyl |
| 196 | phenyl | 2-(2-butyl)-4-(heptafluoroisopropyl)-6-iodophenyl |
| 197 | 2-fluorophenyl | 2-bromo-6-cyano-4-(heptafluoroisopropyl)phenyl |
| 198 | phenyl | 2-bromo-4-(heptafluoroisopropyl)-6-methylthiophenyl |
| 199 | 2-fluorophenyl | 2-bromo-4-(heptafluoroisopropyl)-6-methylthiophenyl |
| 200 | phenyl | 2-bromo-4-(heptafluoroisopropyl)-6-(methylsulfinyl)phenyl |
| 201 | 2-fluorophenyl | 2-chloro-4-(heptafluoroisopropyl)-6-(methylsulfonyl)phenyl |
| 202 | 2-chloropyridin-3-yl | 2-chloro-4-(heptafluoroisopropyl)-6-(methylsulfonyl)phenyl |
| 203 | phenyl | 2-bromo-4-(heptafluoroisopropyl)-6-(methylsulfonyl)phenyl |
| 204 | 2-fluorophenyl | 2-bromo-4-(heptafluoroisopropyl)-6-(methylsulfonyl)phenyl |
| 205 | 4-fluorophenyl | 2-bromo-4-(heptafluoroisopropyl)-6-(methylsulfonyl)phenyl |
| 206 | 4-nitrophenyl | 2-bromo-4-(heptafluoroisopropyl)-6-(methylsulfonyl)phenyl |
| 207 | 4-cyanophenyl | 2-bromo-4-(heptafluoroisopropyl)-6-(methylsulfonyl)phenyl |
| 208 | 2-chloropyridin-3-yl | 2-bromo-4-(heptafluoroisopropyl)-6-(methylsulfonyl)phenyl |
| 209 | phenyl | 4-(heptafluoroisopropyl)-2-methylthiomethyl-6-trifluoromethylphenyl |
| 210 | phenyl | 2-bromo-4-(heptafluoroisopropyl)-6-(trifluoromethylthio)phenyl |
| 211 | phenyl | 2,6-dimethyl-4-(nonafluoro-n-butyl)phenyl |
| 212 | phenyl | 2,6-dimethyl-4-(nonafluoro-2-butyl)phenyl |
| 213 | 2-trifluoromethylphenyl | 2,6-dimethyl-4-(nonafluoro-2-butyl)phenyl |
| 214 | 4-trifluoromethylphenyl | 2,6-dimethyl-4-(nonafluoro-2-butyl)phenyl |
| 215 | 4-trifluoromethoxyphenyl | 2,6-dimethyl-4-(nonafluoro-2-butyl)phenyl |
| 216 | 3-fluorophenyl | 2,6-dimethyl-4-(nonafluoro-2-butyl)phenyl |
| 217 | 4-fluorophenyl | 2,6-dimethyl-4-(nonafluoro-2-butyl)phenyl |
| 218 | 2-chlorophenyl | 2,6-dimethyl-4-(nonafluoro-2-butyl)phenyl |
| 219 | 4-chlorophenyl | 2,6-dimethyl-4-(nonafluoro-2-butyl)phenyl |
| 220 | 2-bromophenyl | 2,6-dimethyl-4-(nonafluoro-2-butyl)phenyl |
| 221 | 2-iodophenyl | 2,6-dimethyl-4-(nonafluoro-2-butyl)phenyl |
| 222 | 3-cyanophenyl | 2,6-dimethyl-4-(nonafluoro-2-butyl)phenyl |
| 223 | 4-cyanophenyl | 2,6-dimethyl-4-(nonafluoro-2-butyl)phenyl |
| 224 | 2-nitrophenyl | 2,6-dimethyl-4-(nonafluoro-2-butyl)phenyl |
| 225 | 3-nitrophenyl | 2,6-dimethyl-4-(nonafluoro-2-butyl)phenyl |
| 226 | 4-nitrophenyl | 2,6-dimethyl-4-(nonafluoro-2-butyl)phenyl |
| 227 | 2-chloro-4-fluorophenyl | 2,6-dimethyl-4-(nonafluoro-2-butyl)phenyl |
| 228 | 2-chloro-6-fluorophenyl | 2,6-dimethyl-4-(nonafluoro-2-butyl)phenyl |
| 229 | 4-chloro-2-fluorophenyl | 2,6-dimethyl-4-(nonafluoro-2-butyl)phenyl |
| 230 | 2,3-difluorophenyl | 2,6-dimethyl-4-(nonafluoro-2-butyl)phenyl |
| 231 | 2,3,6-trifluorophenyl | 2,6-dimethyl-4-(nonafluoro-2-butyl)phenyl |
| 232 | 2,5-difluorophenyl | 2,6-dimethyl-4-(nonafluoro-2-butyl)phenyl |
| 233 | 2,6-difluorophenyl | 2,6-dimethyl-4-(nonafluoro-2-butyl)phenyl |
| 234 | 2,4-dichlorophenyl | 2,6-dimethyl-4-(nonafluoro-2-butyl)phenyl |
| 235 | 2,6-dichlorophenyl | 2,6-dimethyl-4-(nonafluoro-2-butyl)phenyl |
| 236 | 3,4-dichlorophenyl | 2,6-dimethyl-4-(nonafluoro-2-butyl)phenyl |
| 237 | 2-methylthiopyridin-3-yl | 2,6-dimethyl-4-(nonafluoro-2-butyl)phenyl |
| 238 | 2-chloro-4-fluorophenyl | 2,6-dimethyl-4-(nonafluoro-2-butyl)phenyl |
| 239 | 2-chloro-6-fluorophenyl | 2,6-dimethyl-4-(nonafluoro-2-butyl)phenyl |
| 240 | 4-chloro-2-fluorophenyl | 2,6-dimethyl-4-(nonafluoro-2-butyl)phenyl |
| 241 | 4-chloro-2-nitrophenyl | 2,6-dimethyl-4-(nonafluoro-2-butyl)phenyl |
| 242 | 2,3,6-trifluorophenyl | 2,6-dimethyl-4-(nonafluoro-2-butyl)phenyl |
| 243 | pyridin-2-yl | 2,6-dimethyl-4-(nonafluoro-2-butyl)phenyl |
| 244 | pyridin-3-yl | 2,6-dimethyl-4-(nonafluoro-2-butyl)phenyl |
| 245 | 2-fluoropyridin-3-yl | 2,6-dimethyl-4-(nonafluoro-2-butyl)phenyl |
| 246 | 2-chloropyridin-3-yl | 2,6-dimethyl-4-(nonafluoro-2-butyl)phenyl |
| 247 | 2-chloropyridin-5-yl | 2,6-dimethyl-4-(nonafluoro-2-butyl)phenyl |
| 248 | 2-methylthiopyridin-3-yl | 2,6-dimethyl-4-(nonafluoro-2-butyl)phenyl |
| 249 | pyrazin-2-yl | 2,6-dimethyl-4-(nonafluoro-2-butyl)phenyl |
| 250 | furan-2-yl | 2,6-dimethyl-4-(nonafluoro-2-butyl)phenyl |
| 251 | furan-3-yl | 2,6-dimethyl-4-(nonafluoro-2-butyl)phenyl |
| 252 | 2-tetrahydrofuranyl | 2,6-dimethyl-4-(nonafluoro-2-butyl)phenyl |
| 253 | benzofuran-2-yl | 2,6-dimethyl-4-(nonafluoro-2-butyl)phenyl |
| 254 | thiophen-2-yl | 2,6-dimethyl-4-(nonafluoro-2-butyl)phenyl |
| 255 | 2,6-difluorophenyl | 2,6-dichloro-4-(trifluoromethylthio)phenyl |

TABLE 1-continued

| Compound No. | $Q_1$ | $Q_2$ |
|---|---|---|
| 256 | phenyl | 2,6-dibromo-4-(trifluoromethylthio)phenyl |
| 257 | 2,6-difluorophenyl | 2,6-dibromo-4-(trifluoromethylthio)phenyl |
| 258 | phenyl | 2,6-dibromo-4-(pentafluoroethylthio)phenyl |
| 259 | 2-fluorophenyl | 2,6-dibromo-4-(pentafluoroethylthio)phenyl |
| 260 | phenyl | 2,6-dimethyl-4-(heptafluoro-n-propylthio)phenyl |
| 261 | 2-fluorophenyl | 2,6-dimethyl-4-(heptafluoro-n-propylthio)phenyl |
| 262 | phenyl | 2,6-dichloro-4-(heptafluoro-n-propylthio)phenyl |
| 263 | phenyl | 2,6-dibromo-4-(heptafluoro-n-propylthio)phenyl |
| 264 | 2-methylphenyl | 2,6-dibromo-4-(heptafluoro-n-propylthio)phenyl |
| 265 | 4-methylphenyl | 2,6-dibromo-4-(heptafluoro-n-propylthio)phenyl |
| 266 | 2-fluorophenyl | 2,6-dibromo-4-(heptafluoro-n-propylthio)phenyl |
| 267 | 3-fluorophenyl | 2,6-dibromo-4-(heptafluoro-n-propylthio)phenyl |
| 268 | 4-fluorophenyl | 2,6-dibromo-4-(heptafluoro-n-propylthio)phenyl |
| 269 | 2-chlorophenyl | 2,6-dibromo-4-(heptafluoro-n-propylthio)phenyl |
| 270 | 4-chlorophenyl | 2,6-dibromo-4-(heptafluoro-n-propylthio)phenyl |
| 271 | 2-bromophenyl | 2,6-dibromo-4-(heptafluoro-n-propylthio)phenyl |
| 272 | 2-iodophenyl | 2,6-dibromo-4-(heptafluoro-n-propylthio)phenyl |
| 273 | 3-cyanophenyl | 2,6-dibromo-4-(heptafluoro-n-propylthio)phenyl |
| 274 | 4-cyanophenyl | 2,6-dibromo-4-(heptafluoro-n-propylthio)phenyl |
| 275 | 2-nitrophenyl | 2,6-dibromo-4-(heptafluoro-n-propylthio)phenyl |
| 276 | 3-nitrophenyl | 2,6-dibromo-4-(heptafluoro-n-propylthio)phenyl |
| 277 | 4-nitrophenyl | 2,6-dibromo-4-(heptafluoro-n-propylthio)phenyl |
| 278 | 2-trifluoromethylphenyl | 2,6-dibromo-4-(heptafluoro-n-propylthio)phenyl |
| 279 | 4-trifluoromethylphenyl | 2,6-dibromo-4-(heptafluoro-n-propylthio)phenyl |
| 280 | 4-trifluoromethoxylphenyl | 2,6-dibromo-4-(heptafluoro-n-propylthio)phenyl |
| 281 | 2,3-difluorophenyl | 2,6-dibromo-4-(heptafluoro-n-propylthio)phenyl |
| 282 | 2,4-difluorophenyl | 2,6-dibromo-4-(heptafluoro-n-propylthio)phenyl |
| 283 | 2,5-difluorophenyl | 2,6-dibromo-4-(heptafluoro-n-propylthio)phenyl |
| 284 | 2,6-difluorophenyl | 2,6-dibromo-4-(heptafluoro-n-propylthio)phenyl |
| 285 | 3-aminophenyl | 2,6-dibromo-4-(heptafluoro-n-propylthio)phenyl |
| 286 | 3-(acetylamino)phenyl | 2,6-dibromo-4-(heptafluoro-n-propylthio)phenyl |
| 287 | 3-(methylsulfonylamino)phenyl | 2,6-dibromo-4-(heptafluoro-n-propylthio)phenyl |
| 288 | 2,4-dinitrophenyl | 2,6-dibromo-4-(heptafluoro-n-propylthio)phenyl |
| 289 | 3,4-dinitrophenyl | 2,6-dibromo-4-(heptafluoro-n-propylthio)phenyl |
| 290 | 3-methyl-4-nitrophenyl | 2,6-dibromo-4-(heptafluoro-n-propylthio)phenyl |
| 291 | 5-amino-2-fluorophenyl | 2,6-dibromo-4-(heptafluoro-n-propylthio)phenyl |
| 292 | 2-fluoro-5-nitrophenyl | 2,6-dibromo-4-(heptafluoro-n-propylthio)phenyl |
| 293 | 2-fluoro-5-(methylsulfonylamino)phenyl | 2,6-dibromo-4-(heptafluoro-n-propylthio)phenyl |
| 294 | 2-methoxy-4-nitrophenyl | 2,6-dibromo-4-(heptafluoro-n-propylthio)phenyl |
| 295 | 3-methoxy-4-nitrophenyl | 2,6-dibromo-4-(heptafluoro-n-propylthio)phenyl |
| 296 | 5-(acetylamino)-2-fluorophenyl | 2,6-dibromo-4-(heptatfluoro-n-propylthio)phenyl |
| 297 | 2,4-dichlorophenyl | 2,6-dibromo-4-(heptafluoro-n-propylthio)phenyl |
| 298 | 2,6-dichlorophenyl | 2,6-dibromo-4-(heptafluoro-n-propylthio)phenyl |
| 299 | 3,4-dichlorophenyl | 2,6-dibromo-4-(heptafluoro-n-propylthio)phenyl |
| 300 | 2-chloro-4-nitrophenyl | 2,6-dibromo-4-(heptafluoro-n-propylthio)phenyl |
| 301 | 2-chloro-4-fluorophenyl | 2,6-dibromo-4-(heptafluoro-n-propylthio)phenyl |
| 302 | 2-chloro-6-fluorophenyl | 2,6-dibromo-4-(heptafluoro-n-propylthio)phenyl |
| 303 | 4-chloro-2-fluorophenyl | 2,6-dibromo-4-(heptafluoro-n-propylthio)phenyl |
| 304 | 4-chloro-2-nitrophenyl | 2,6-dibromo-4-(heptafluoro-n-propylthio)phenyl |
| 305 | 2,3,6-trifluorophenyl | 2,6-dibromo-4-(heptafluoro-n-propylthio)phenyl |
| 306 | pyridin-2-yl | 2,6-dibromo-4-(heptafluoro-n-propylthio)phenyl |
| 307 | pyridin-3-yl | 2,6-dibromo-4-(heptatfluoro-n-propylthio)phenyl |
| 308 | 2-fluoropyridin-3-yl | 2,6-dibromo-4-(heptafluoro-n-propylthio)phenyl |
| 309 | 2-chloropyridin-3-yl | 2,6-dibromo-4-(heptafluoro-n-propylthio)phenyl |
| 310 | 2-chloropyridin-5-yl | 2,6-dibromo-4-(heptafluoro-n-propylthio)phenyl |
| 311 | 2-methylthiopyridin-3-yl | 2,6-dibromo-4-(heptafluoro-n-propylthio)phenyl |
| 312 | 2,6-dichloropyridin-3-yl | 2,6-dibromo-4-(heptafluoro-n-propylthio)phenyl |
| 313 | 2,6-dichloropyridin-4-yl | 2,6-dibromo-4-(heptafluoro-n-propylthio)phenyl |
| 314 | 2-chloro-6-methylpyridin-3-yl | 2,6-dibromo-4-(heptafluoro-n-propylthio)phenyl |
| 315 | pyridine-N-oxide-2-yl | 2,6-dibromo-4-(heptafluoro-n-propylthio)phenyl |
| 316 | pyrazin-2-yl | 2,6-dibromo-4-(heptafluoro-n-propylthio)phenyl |
| 317 | 1-methyl-3-nitro-1H-pyrazol-4-yl | 2,6-dibromo-4-(heptafluoro-n-propylthio)phenyl |
| 318 | 1-methyl-3-trifluoromethyl-1H-pyrazol-4-yl | 2,6-dibromo-4-(heptafluoro-n-propylthio)phenyl |
| 319 | 1-methyl-5-trifluoromethyl-1H-pyrazol-4-yl | 2,6-dibromo-4-(heptafluoro-n-propylthio)phenyl |
| 320 | 2-tetrahydrofuranyl | 2,6-dibromo-4-(heptafluoro-n-propylthio)phenyl |
| 321 | 2-phenylthiazol-4-yl | 2,6-dibromo-4-(heptafluoro-n-propylthio)phenyl |
| 322 | furan-2-yl | 2,6-dibromo-4-(heptafluoro-n-propylthio)phenyl |
| 323 | furan-3-yl | 2,6-dibromo-4-(heptafluoro-n-propylthio)phenyl |
| 324 | 2-tetrahydrofuranyl | 2,6-dibromo-4-(heptafluoro-n-propylthio)phenyl |
| 325 | benzofuran-2-yl | 2,6-dibromo-4-(heptafluoro-n-propylthio)phenyl |

TABLE 1-continued

| Compound No. | Q₁ | Q₂ |
|---|---|---|
| 326 | thiophen-2-yl | 2,6-dibromo-4-(heptafluoro-n-propylthio)phenyl |
| 327 | phenyl | 2,6-diiodo-4-(heptafluoro-n-propylthio)phenyl |
| 328 | 2-fluorophenyl | 2,6-diiodo-4-(heptafluoro-n-propylthio)phenyl |
| 329 | phenyl | 2,6-dicloro-4-(heptafluoroisopropylthio)phenyl |
| 330 | 2-fluorophenyl | 2,6-dicloro-4-(heptafluoroisopropylthio)phenyl |
| 331 | 2-chloropyridin-3-yl | 2,6-dichloro-4-(heptafluoroisopropylthio)phenyl |
| 332 | phenyl | 2,6-dibromo-4-(heptafluoroisopropylthio)phenyl |
| 333 | phenyl | 2,6-dibromo-4-(nonafluoro-n-butylthio)phenyl |
| 334 | 2-fluorophenyl | 2,6-dibromo-4-(nonafluoro-n-butylthio)phenyl |
| 335 | phenyl | 2,6-dibromo-4-(heptafluoro-n-propylsulfinyl)phenyl |
| 336 | 2-methylphenyl | 2,6-dibromo-4-(heptafluoro-n-propylsulfinyl)phenyl |
| 337 | 4-methylphenyl | 2,6-dibromo-4-(heptafluoro-n-propylsulfinyl)phenyl |
| 338 | 2-fluorophenyl | 2,6-dibromo-4-(heptafluoro-n-propylsulfinyl)phenyl |
| 339 | 3-fluorophenyl | 2,6-dibromo-4-(heptafluoro-n-propylsulfinyl)phenyl |
| 340 | 4-fluorophenyl | 2,6-dibromo-4-(heptafluoro-n-propylsulfinyl)phenyl |
| 341 | 2-chlorophenyl | 2,6-dibromo-4-(heptafluoro-n-propylsulfinyl)phenyl |
| 342 | 4-chlorophenyl | 2,6-dibromo-4-(heptafluoro-n-propylsulfinyl)phenyl |
| 343 | 2-bromophenyl | 2,6-dibromo-4-(heptafluoro-n-propylsulfinyl)phenyl |
| 344 | 2-iodophenyl | 2,6-dibromo-4-(heptafluoro-n-propylsulfinyl)phenyl |
| 345 | 3-cyanophenyl | 2,6-dibromo-4-(heptafluoro-n-propylsulfinyl)phenyl |
| 346 | 4-cyanophenyl | 2,6-dibromo-4-(heptafluoro-n-propylsulfinyl)phenyl |
| 347 | 2-nitrophenyl | 2,6-dibromo-4-(heptafluoro-n-propylsulfinyl)phenyl |
| 348 | 3-nitrophenyl | 2,6-dibromo-4-(heptafluoro-n-propylsulfinyl)phenyl |
| 349 | 4-nitrophenyl | 2,6-dibromo-4-(heptafluoro-n-propylsulfinyl)phenyl |
| 350 | 2-trifluoromethylphenyl | 2,6-dibromo-4-(heptafluoro-n-propylsulfinyl)phenyl |
| 351 | 4-trifluoromethylphenyl | 2,6-dibromo-4-(heptafluoro-n-propylsulfinyl)phenyl |
| 352 | 4-trifluoromethoxylphenyl | 2,6-dibromo-4-(heptafluoro-n-propylsulfinyl)phenyl |
| 353 | 2,3-difluorophenyl | 2,6-dibromo-4-(heptafluoro-n-propylsulfinyl)phenyl |
| 354 | 2,4-difluorophenyl | 2,6-dibromo-4-(heptafluoro-n-propylsulfinyl)phenyl |
| 355 | 2,5-difluorophenyl | 2,6-dibromo-4-(heptafluoro-n-propylsulfinyl)phenyl |
| 356 | 2,6-difluorophenyl | 2,6-dibromo-4-(heptafluoro-n-propylsulfinyl)phenyl |
| 357 | 2,4-dichlorophenyl | 2,6-dibromo-4-(heptafluoro-n-propylsulfinyl)phenyl |
| 358 | 2,6-dichlorophenyl | 2,6-dibromo-4-(heptafluoro-n-propylsulfinyl)phenyl |
| 359 | 3,4-dichlorophenyl | 2,6-dibromo-4-(heptafluoro-n-propylsulfinyl)phenyl |
| 360 | 2-chloro-4-nitrophenyl | 2,6-dibromo-4-(heptafluoro-n-propylsulfinyl)phenyl |
| 361 | 2-chloro-4-fluorophenyl | 2,6-dibromo-4-(heptafluoro-n-propylsulfinyl)phenyl |
| 362 | 2-chloro-6-fluorophenyl | 2,6-dibromo-4-(heptafluoro-n-propylsulfinyl)phenyl |
| 363 | 4-chloro-2-fluorophenyl | 2,6-dibromo-4-(heptafluoro-n-propylsulfinyl)phenyl |
| 364 | 4-chloro-2-nitrophenyl | 2,6-dibromo-4-(heptafluoro-n-propylsulfinyl)phenyl |
| 365 | 2,3,6-trifluorophenyl | 2,6-dibromo-4-(heptafluoro-n-propylsulfinyl)phenyl |
| 366 | pyridin-2-yl | 2,6-dibromo-4-(heptafluoro-n-propylsulfinyl)phenyl |
| 367 | pyridin-3-yl | 2,6-dibromo-4-(heptafluoro-n-propylsulfinyl)phenyl |
| 368 | 2-fluoropyridin-3-yl | 2,6-dibromo-4-(heptafluoro-n-propylsulfinyl)phenyl |
| 369 | 2-chloropyridin-3-yl | 2,6-dibromo-4-(heptafluoro-n-propylsulfinyl)phenyl |
| 370 | 2-chloropyridin-5-yl | 2,6-dibromo-4-(heptafluoro-n-propylsulfinyl)phenyl |
| 371 | 2-methylthiopyridin-3-yl | 2,6-dibromo-4-(heptafluoro-n-propylsulfinyl)phenyl |
| 372 | pyrazin-2-yl | 2,6-dibromo-4-(heptafluoro-n-propylsulfinyl)phenyl |
| 373 | furan-2-yl | 2,6-dibromo-4-(heptafluoro-n-propylsulfinyl)phenyl |
| 374 | thiophen-2-yl | 2,6-dibromo-4-(heptafluoro-n-propylsulfinyl)phenyl |
| 375 | 2,6-difluorophenyl | 2,6-dichloro-4-(trifluoromethylsulfonyl)phenyl |
| 376 | phenyl | 2,6-dibromo-4-(trifluoromethylsulfonyl)phenyl |
| 377 | 2,6-difluorophenyl | 2,6-dibromo-4-(trifluoromethylsulfonyl)phenyl |
| 378 | 2-fluorophenyl | 2,6-dichloro-4-(heptafluoroisopropylsulfonyl)phenyl |
| 379 | phenyl | 2,6-dichloro-4-(heptafluoroisopropylsulfonyl)phenyl |
| 380 | phenyl | 2,6-dichloro-4-(heptafluoroisopropylsulfonyl)phenyl |
| 381 | 2-methylphenyl | 2,6-dichloro-4-(heptafluoroisopropylsulfonyl)phenyl |
| 382 | 4-methylphenyl | 2,6-dichloro-4-(heptafluoroisopropylsulfonyl)phenyl |
| 383 | 2-fluorophenyl | 2,6-dichloro-4-(heptafluoroisopropylsulfonyl)phenyl |
| 384 | 3-fluorophenyl | 2,6-dichloro-4-(heptafluoroisopropylsulfonyl)phenyl |
| 385 | 4-fluorophenyl | 2,6-dichloro-4-(heptafluoroisopropylsulfonyl)phenyl |
| 386 | 2-chlorophenyl | 2,6-dichloro-4-(heptafluoroisopropylsulfonyl)phenyl |
| 387 | 4-chlorophenyl | 2,6-dichloro-4-(heptafluoroisopropylsulfonyl)phenyl |
| 388 | 2-bromophenyl | 2,6-dichloro-4-(heptafluoroisopropylsulfonyl)phenyl |
| 389 | 2-iodophenyl | 2,6-dichloro-4-(heptafluoroisopropylsulfonyl)phenyl |
| 390 | 3-cyanophenyl | 2,6-dichloro-4-(heptofluoroisopropylsulfonyl)phenyl |
| 391 | 4-cyanophenyl | 2,6-dibromo-4-(heptafluoro-n-propylsulfonyl)phenyl |
| 392 | 2-nitrophenyl | 2,6-dibromo-4-(heptafluoro-n-propylsulfonyl)phenyl |
| 393 | 3-nitrophenyl | 2,6-dibromo-4-(heptafluoro-n-propylsulfonyl)phenyl |
| 394 | 4-nitrophenyl | 2,6-dibromo-4-(heptafluoro-n-propylsulfonyl)phenyl |
| 395 | 2-trifluoromethylphenyl | 2,6-dibromo-4-(heptafluoro-n-propylsulfonyl)phenyl |
| 396 | 4-trifluoromethylphenyl | 2,6-dibromo-4-(heptafluoro-n-propylsulfonyl)phenyl |
| 397 | 4-trifluoromethoxylphenyl | 2,6-dibromo-4-(heptafluoro-n-propylsulfonyl)phenyl |
| 398 | 2,3-difluorophenyl | 2,6-dibromo-4-(heptafluoro-n-propylsulfonyl)phenyl |
| 399 | 2,4-difluorophenyl | 2,6-dibromo-4-(heptafluoro-n-propylsulfonyl)phenyl |
| 400 | 2,5-difluorophenyl | 2,6-dibromo-4-(heptafluoro-n-propylsulfonyl)phenyl |
| 401 | 2,6-difluorophenyl | 2,6-dibromo-4-(heptafluoro-n-propylsulfonyl)phenyl |
| 402 | 2,4-dichlorophenyl | 2,6-dibromo-4-(heptafluoro-n-propylsulfonyl)phenyl |

TABLE 1-continued

| Compound No. | Q₁ | Q₂ |
|---|---|---|
| 403 | 2,6-dichlorophenyl | 2,6-dibromo-4-(heptafluoro-n-propylsulfonyl)phenyl |
| 404 | 3,4-dichlorophenyl | 2,6-dibromo-4-(heptafluoro-n-propylsulfonyl)phenyl |
| 405 | 2-chloro-4-nitrophenyl | 2,6-dibromo-4-(heptafluoro-n-propylsulfonyl)phenyl |
| 406 | 2-chloro-4-fluorophenyl | 2,6-dibromo-4-(heptafluoro-n-propylsulfonyl)phenyl |
| 407 | 2-chloro-6-fluorophenyl | 2,6-dibromo-4-(heptafluoro-n-propylsulfonyl)phenyl |
| 408 | 4-chloro-2-fluorophenyl | 2,6-dibromo-4-(heptafluoro-n-propylsulfonyl)phenyl |
| 409 | 4-chloro-2-nitrophenyl | 2,6-dibromo-4-(heptafluoro-n-propylsulfonyl)phenyl |
| 410 | 2,3,6-trifluorophenyl | 2,6-dibromo-4-(heptafluoro-n-propylsulfonyl)phenyl |
| 411 | pyridin-2-yl | 2,6-dibromo-4-(heptafluoro-n-propylsulfonyl)phenyl |
| 412 | pyridin-3-yl | 2,6-dibromo-4-(heptafluoro-n-propylsulfonyl)phenyl |
| 413 | 2-fluoropyridin-3-yl | 2,6-dibromo-4-(heptafluoro-n-propylsulfonyl)phenyl |
| 414 | 2-chloropyridin-3-yl | 2,6-dibromo-4-(heptafluoro-n-propylsulfonyl)phenyl |
| 415 | 2-chloropyridin-5-yl | 2,6-dibromo-4-(heptafluoro-n-propylsulfonyl)phenyl |
| 416 | 2-methylthiopyridin-3-yl | 2,6-dibromo-4-(heptafluoro-n-propylsulfonyl)phenyl |
| 417 | pyrazin-2-yl | 2,6-dibromo-4-(heptafluoro-n-propylsulfonyl)phenyl |
| 418 | furan-2-yl | 2,6-dibromo-4-(heptafluoro-n-propylsulfonyl)phenyl |
| 419 | thiophen-2-yl | 2,6-dibromo-4-(heptafluoro-n-propylsulfonyl)phenyl |
| 420 | phenyl | 2,6-dimethyl v-4-(heptafluoro-n-propylthio)phenyl |
| 421 | 2-methylphenyl | 2,6-dimethyl-4-(heptafluoro-n-propylthio)phenyl |
| 422 | 4-methylphenyl | 2,6-dimethyl-4-(heptafluoro-n-propylthio)phenyl |
| 423 | 2-fluorophenyl | 2,6-dimethyl-4-(heptafluoro-n-propylthio)phenyl |
| 424 | 3-fluorophenyl | 2,6-dimethyl-4-(heptafluoro-n-propylthio)phenyl |
| 425 | 4-fluorophenyl l | 2,6-dimethyl-4-(heptafluoro-n-propylthio)phenyl |
| 426 | 2-chlorophenyl | 2,6-dimethyl-4-(heptafluoro-n-propylthio)phenyl |
| 427 | 4-chlorophenyl | 2,6-dimethyl-4-(heptafluoro-n-propylthio)phenyl |
| 428 | 2-bromophenyl | 2,6-dimethyl-4-(heptafluoro-n-propylthio)phenyl |
| 429 | 2-iodophenyl | 2,6-dimethyl-4-(heptafluoro-n-propylthio)phenyl |
| 430 | 3-cyanophenyl | 2,6-dimethyl-4-(heptafluoro-n-propylthio)phenyl |
| 431 | 4-cyanophenyl | 2,6-dimethyl-4-(heptafluoro-n-propylthio)phenyl |
| 432 | 2-nitrophenyl | 2,6-dimethyl-4-(heptafluoro-n-propylthio)phenyl |
| 433 | 3-nitrophenyl | 2,6-dimethyl-4-(heptafluoro-n-propylthio)phenyl |
| 434 | 4-nitrophenyl | 2,6-dimethyl-4-(heptafluoro-n-propylthio)phenyl |
| 435 | 2-trifluoromethylphenyl | 2,6-dimethyl-4-(heptafluoro-n-propylthio)phenyl |
| 436 | 4-trifluoromethylphenyl | 2,6-dimethyl-4-(heptafluoro-n-propylthio)phenyl |
| 437 | 4-trifluoromethoxylphenyl | 2,6-dimethyl-4-(heptafluoro-n-propylthio)phenyl |
| 438 | 2,3-difluorophenyl | 2,6-dimethyl-4-(heptafluoro-n-propylthio)phenyl |
| 439 | 2,4-difluorophenyl | 2,6-dimethyl-4-(heptafluoro-n-propylthio)phenyl |
| 440 | 2,5-difluorophenyl | 2,6-dimethyl-4-(heptafluoro-n-propylthio)phenyl |
| 441 | 2,6-difluorophenyl | 2,6-dimethyl-4-(heptafluoro-n-propylthio)phenyl |
| 442 | 2,4-dichlorophenyl | 2,6-dimethyl-4-(heptafluoro-n-propylthio)phenyl |
| 443 | 2,6-dichlorophenyl | 2,6-dimethyl-4-(heptafluoro-n-propylthio)phenyl |
| 444 | 3,4-dichlorophenyl | 2,6-dimethyl-4-(heptafluoro-n-propylthio)phenyl |
| 445 | 2-chloro-4-nitrophenyl | 2,6-dimethyl-4-(heptafluoro-n-propylthio)phenyl |
| 446 | 2-chloro-4-fluorophenyl | 2,6-dimethyl-4-(heptafluoro-n-propylthio)phenyl |
| 447 | 2-chloro-6-fluorophenyl | 2,6-dimethyl-4-(heptafluoro-n-propylthio)phenyl |
| 448 | 4-chloro-2-fluorophenyl | 2,6-dimethyl-4-(heptafluoro-n-propylthio)phenyl |
| 449 | 4-chloro-2-nitrophenyl | 2,6-dimethyl-4-(heptafluoro-n-propylthio)phenyl |
| 450 | 2,3,6-trifluorophenyl | 2,6-dimethyl-4-(heptafluoro-n-propylthio)phenyl |
| 451 | pyridin-2-yl | 2,6-dimethyl-4-(heptafluoro-n-propylthio)phenyl |
| 452 | pyridin-3-yl | 2,6-dimethyl-4-(heptafluoro-n-propylthio)phenyl |
| 453 | 2-fluoropyridin-3-yl | 2,6-dimethyl-4-(heptafluoro-n-propylthio)phenyl |
| 454 | 2-chloropyridin-3-yl | 2,6-dimethyl-4-(heptafluoro-n-propylthio)phenyl |
| 455 | 2-chloropyridin-5-yl | 2,6-dimethyl-4-(heptafluoro-n-propylthio)phenyl |
| 456 | 2-methylthiopyridin-3-yl | 2,6-dimethyl-4-(heptafluoro-n-propylthio)phenyl |
| 457 | pyrazin-2-yl | 2,6-dimethyl-4-(heptafluoro-n-propylthio)phenyl |
| 458 | furan-2-yl | 2,6-dimethyl-4-(heptafluoro-n-propylthio)phenyl |
| 459 | thiophen-2-yl | 2,6-dimethyl-4-(heptafluoro-n-propylthio)phenyl |
| 460 | 2,6-difluorophenyl | 2,6-dichloro-4-(trifluoromethylsulfonyl)phenyl |
| 461 | phenyl | 2-bromo-6-(heptafluoroisopropyloxy)-4-methylpyridin-3-yl |
| 462 | 2-fluorophenyl | 2-bromo-6-(heptafluoroisopropyloxy)-4-methylpyridin-3-yl |
| 463 | phenyl | 2,4-dimethyl-6-(2,2,2-trifluoro-1-trifluoromethylethoxy)pyridin-3-yl |
| 464 | phenyl | 2-chloro-4-methyl-6-(2,2,2-trifluoro-1-trifluoromethylethoxy)pyridin-3-yl |
| 465 | phenyl | 2-bromo-4-methyl-6-(2,2,2-trifluoro-1-trifluoromethylethoxy)pyridin-3-yl |
| 466 | 2-fluorophenyl | 2-bromo-4-methyl-6-(2,2,2-trifluoro-1-trifluoromethylethoxy)pyridin-3-yl |
| 467 | phenyl | 2-iodo-4-methyl-6-(2,2,2-tritluoro-1-trifluoromethylethoxy)pyridin-3-yl |

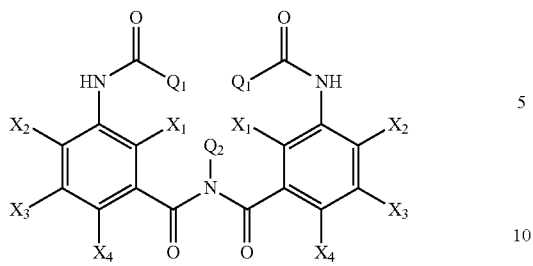

TABLE 2

| Compound No. | Q$_1$ | X$_1$ | X$_2$ | X$_3$ | X$_4$ | Q$_2$ |
|---|---|---|---|---|---|---|
| 601 | phenyl | F | H | H | H | 2,6-dimethyl-4-(heptafluoroisopropyl)phenyl |
| 602 | 2-methylphenyl | F | H | H | H | 2,6-dimethyl-4-(heptafluoroisopropyl)phenyl |
| 603 | 3-methylphenyl | F | H | H | H | 2,6-dimethyl-4-(heptafluoroisopropyl)phenyl |
| 604 | 4-methylphenyl | F | H | H | H | 2,6-dimethyl-4-(heptafluoroisopropyl)phenyl |
| 605 | 2-nitrophenyl | F | H | H | H | 2,6-dimethyl-4-(heptafluoroisopropyl)phenyl |
| 606 | 3-nitrophenyl | F | H | H | H | 2,6-dimethyl-4-(heptafluoroisopropyl)phenyl |
| 607 | 4-nitrophenyl | F | H | H | H | 2,6-dimethyl-4-(heptafluoroisopropyl)phenyl |
| 608 | 3-cyanophenyl | F | H | H | H | 2,6-dimethyl-4-(heptafluoroisopropyl)phenyl |
| 609 | 4-cyanophenyl | F | H | H | H | 2,6-dimethyl-4-(heptafluoroisopropyl)phenyl |
| 610 | 2-fluorophenyl | F | H | H | H | 2,6-dimethyl-4-(heptafluoroisopropyl)phenyl |
| 611 | 3-fluorophenyl | F | H | H | H | 2,6-dimethyl-4-(heptafluoroisopropyl)phenyl |
| 612 | 4-fluorophenyl | F | H | H | H | 2,6-dimethyl-4-(heptafluoroisopropyl)phenyl |
| 613 | 2-chlorophenyl | F | H | H | H | 2,6-dimethyl-4-(heptafluoroisopropyl)phenyl |
| 614 | 4-chlorophenyl | F | H | H | H | 2,6-dimethyl-4-(heptafluoroisopropyl)phenyl |
| 615 | 2-bromophenyl | F | H | H | H | 2,6-dimethyl-4-(heptafluoroisopropyl)phenyl |
| 616 | 2-iodophenyl | F | H | H | H | 2,6-dimethyl-4-(heptafluoroisopropyl)phenyl |
| 617 | 2-trifluoromethylphenyl | F | H | H | H | 2,6-dimethyl-4-(heptafluoroisopropyl)phenyl |
| 618 | 4-trifluoromethylphenyl | F | H | H | H | 2,6-dimethyl-4-(heptafluoroisopropyl)phenyl |
| 619 | 4-trifluoromethoxyphenyl | F | H | H | H | 2,6-dimethyl-4-(heptafluoroisopropyl)phenyl |
| 620 | 4-(dimethylamino)phenyl | F | H | H | H | 2,6-dimethyl-4-(heptafluoroisopropyl)phenyl |
| 621 | 2,3-difluorophenyl | F | H | H | H | 2,6-dimethyl-4-(heptafluoroisopropyl)phenyl |
| 622 | 2,4-difluorophenyl | F | H | H | H | 2,6-dimethyl-4-(heptafluoroisopropyl)phenyl |
| 623 | 2,5-difluorophenyl | F | H | H | H | 2,6-dimethyl-4-(heptafluoroisopropyl)phenyl |
| 624 | 2,6-difluorophenyl | F | H | H | H | 2,6-dimethyl-4-(heptafluoroisopropyl)phenyl |
| 625 | 2,4-dichlorophenyl | F | H | H | H | 2,6-dimethyl-4-(heptafluoroisopropyl)phenyl |
| 626 | 2,6-dichlorophenyl | F | H | H | H | 2,6-dimethyl-4-(heptafluoroisopropyl)phenyl |
| 627 | 3,4-dichlorophenyl | F | H | H | H | 2,6-dimethyl-4-(heptafluoroisopropyl)phenyl |
| 628 | 2-fluoro-4-nitrophenyl | F | H | H | H | 2,6-dimethyl-4-(heptafluoroisopropyl)phenyl |
| 629 | 4-fluoro-2-nitrophenyl | F | H | H | H | 2,6-dimethyl-4-(heptafluoroisopropyl)phenyl |
| 630 | 2-chloro-4-fluorophenyl | F | H | H | H | 2,6-dimethyl-4-(heptafluoroisopropyl)phenyl |

TABLE 2-continued

| Compound No. | Q1 | X1 | X2 | X3 | X4 | Q2 |
|---|---|---|---|---|---|---|
| 631 | 4-chloro-2-fluorophenyl | F | H | H | H | 2,6-dimethyl-4-(heptafluoroisopropyl)phenyl |
| 632 | 2-chloro-6-fluorophenyl | F | H | H | H | 2,6-dimethyl-4-(heptafluoroisopropyl)phenyl |
| 633 | 2-chloro-4-nitrophenyl | F | H | H | H | 2,6-dimethyl-4-(heptafluoroisopropyl)phenyl |
| 634 | 4-chloro-2-nitrophenyl | F | H | H | H | 2,6-dimethyl-4-(heptafluoroisopropyl)phenyl |
| 635 | 2,3,6-trifluorophenyl | F | H | H | H | 2,6-dimethyl-4-(heptafluoroisopropyl)phenyl |
| 636 | pyridin-2-yl | F | H | H | H | 2,6-dimethyl-4-(heptafluoroisopropyl)phenyl |
| 637 | pyridin-3-yl | F | H | H | H | 2,6-dimethyl-4-(heptafluoroisopropyl)phenyl |
| 638 | 2-fluoropyridin-3-yl | F | H | H | H | 2,6-dimethyl-4-(heptafluoroisopropyl)phenyl |
| 639 | 2-chloropyridin-3-yl | F | H | H | H | 2,6-dimethyl-4-(heptafluoroisopropyl)phenyl |
| 640 | 2-chloropyridin-5-yl | F | H | H | H | 2,6-dimethyl-4-(heptafluoroisopropyl)phenyl |
| 641 | 2-methylthiopyridin-3-yl | F | H | H | H | 2,6-dimethyl-4-(heptafluoroisopropyl)phenyl |
| 642 | pyrazin-2-yl | F | H | H | H | 2,6-dimethyl-4-(heptafluoroisopropyl)phenyl |
| 643 | furan-2-yl | F | H | H | H | 2,6-dimethyl-4-(heptafluoroisopropyl)phenyl |
| 644 | furan-3-yl | F | H | H | H | 2,6-dimethyl-4-(heptafluoroisopropyl)phenyl |
| 645 | 2-tetrahydrofuranyl | F | H | H | H | 2,6-dimethyl-4-(heptafluoroisopropyl)phenyl |
| 646 | benzofuran-2-yl | F | H | H | H | 2,6-dimethyl-4-(heptafluoroisopropyl)phenyl |
| 647 | thiophen-2-yl | F | H | H | H | 2,6-dimethyl-4-(heptafluoroisopropyl)phenyl |
| 648 | 2-methyl-5,6-dihydro-4H-pyran-3-yl | F | H | H | H | 2,6-dimethyl-4-(heptafluoroisopropyl)phenyl |
| 649 | phenyl | H | Cl | H | H | 2,6-dimethyl-4-(heptafluoroisopropyl)phenyl |
| 650 | phenyl | H | F | H | H | 2,6-dimethyl-4-(heptafluoroisopropyl)phenyl |
| 651 | 4-nitrophenyl | H | F | H | H | 2,6-dimethyl-4-(heptafluoroisopropyl)phenyl |
| 652 | 4-cyanophenyl | H | F | H | H | 2,6-dimethyl-4-(heptafluoroisopropyl)phenyl |
| 653 | 2-fluorophenyl | H | F | H | H | 2,6-dimethyl-4-(heptafluoroisopropyl)phenyl |
| 654 | 4-fluorophenyl | H | F | H | H | 2,6-dimethyl-4-(heptafluoroisopropyl)phenyl |
| 655 | 4-trifluoromethylphenyl | H | F | H | H | 2,6-dimethyl-4-(heptafluoroisopropyl)phenyl |
| 656 | 2,4-difluorophenyl | H | F | H | H | 2,6-dimethyl-4-(heptafluoroisopropyl)phenyl |
| 657 | 2-chloropyridin-3-yl | H | F | H | H | 2,6-dimethyl-4-(heptafluoroisopropyl)phenyl |
| 658 | phenyl | H | H | CF3 | H | 2,6-dimethyl-4-(heptafluoroisopropyl)phenyl |
| 659 | phenyl | H | H | H | F | 2,6-dimethyl-4-(heptafluoroisopropyl)phenyl |
| 660 | phenyl | H | H | H | Cl | 2,6-dimethyl-4-(heptafluoroisopropyl)phenyl |
| 661 | phenyl | H | H | H | Br | 2,6-dimethyl-4-(heptafluoroisopropyl)phenyl |
| 662 | phenyl | H | H | H | I | 2,6-dimethyl-4-(heptafluoroisopropyl)phenyl |
| 663 | phenyl | F | H | H | F | 2,6-dimethyl-4-(heptafluoroisopropyl)phenyl |
| 664 | phenyl | H | Br | H | Br | 2,6-dimethyl-4-(heptafluoroisopropyl)phenyl |
| 665 | phenyl | F | H | H | H | 2,6-dimethyl-4-(nonafluoro-2-butyl)phenyl |
| 666 | 2-methylphenyl | F | H | H | H | 2,6-dimethyl-4-(nonafluoro-2-butyl)phenyl |
| 667 | 4-methylphenyl | F | H | H | H | 2,6-dimethyl-4-(nonafluoro-2-butyl)phenyl |
| 668 | 2-fluorophenyl | F | H | H | H | 2,6-dimethyl-4-(nonafluoro-2-butyl)phenyl |

TABLE 2-continued

| Compound No. | Q₁ | X₁ | X₂ | X₃ | X₄ | Q₂ |
|---|---|---|---|---|---|---|
| 669 | 3-fluorophenyl | F | H | H | H | 2,6-dimethyl-4-(nonafluoro-2-butyl)phenyl |
| 670 | 4-fluorophenyl | F | H | H | H | 2,6-dimethyl-4-(nonafluoro-2-butyl)phenyl |
| 671 | 2-chlorophenyl | F | H | H | H | 2,6-dimethyl-4-(nonafluoro-2-butyl)phenyl |
| 672 | 4-chlorophenyl | F | H | H | H | 2,6-dimethyl-4-(nonafluoro-2-butyl)phenyl |
| 673 | 2-bromophenyl | F | H | H | H | 2,6-dimethyl-4-(nonafluoro-2-butyl)phenyl |
| 674 | 2-iodophenyl | F | H | H | H | 2,6-dimethyl-4-(nonafluoro-2-butyl)phenyl |
| 675 | 3-cyanophenyl | F | H | H | H | 2,6-dimethyl-4-(nonafluoro-2-butyl)phenyl |
| 676 | 4-cyanophenyl | F | H | H | H | 2,6-dimethyl-4-(nonafluoro-2-butyl)phenyl |
| 677 | 2-nitrophenyl | F | F | H | H | 2,6-dimethyl-4-(nonafluoro-2-butyl)phenyl |
| 678 | 3-nitrophenyl | F | H | H | H | 2,6-dimethyl-4-(nonafluoro-2-butyl)phenyl |
| 679 | 4-nitrophenyl | F | H | H | H | 2,6-dimethyl-4-(nonafluoro-2-butyl)phenyl |
| 680 | 2-trifluoromethylphenyl | F | H | H | H | 2,6-dimethyl-4-(nonafluoro-2-butyl)phenyl |
| 681 | 4-trifluoromethylphenyl | F | H | H | H | 2,6-dimethyl-4-(nonafluoro-2-butyl)phenyl |
| 682 | 4-trifluoromethoxyphenyl | F | H | H | H | 2,6-dimethyl-4-(nonafluoro-2-butyl)phenyl |
| 683 | 2,3-difluorophenyl | F | H | H | H | 2,6-dimethyl-4-(nonafluoro-2-butyl)phenyl |
| 684 | 2,4-difluorophenyl | F | H | H | H | 2,6-dimethyl-4-(nonafluoro-2-butyl)phenyl |
| 685 | 2,5-difluorophenyl | F | H | H | H | 2,6-dimethyl-4-(nonafluoro-2-butyl)phenyl |
| 686 | 2,6-difluorophenyl | F | H | H | H | 2,6-dimethyl-4-(nonafluoro-2-butyl)phenyl |
| 687 | 2,4-dichlorophenyl | F | H | H | H | 2,6-dimethyl-4-(nonafluoro-2-butyl)phenyl |
| 688 | 2,6-dichlorophenyl | F | H | H | H | 2,6-dimethyl-4-(nonafluoro-2-butyl)phenyl |
| 689 | 3,4-dichlorophenyl | F | H | H | H | 2,6-dimethyl-4-(nonafluoro-2-butyl)phenyl |
| 690 | 2-chloro-4-nitrophenyl | F | H | H | H | 2,6-dimethyl-4-(nonafluoro-2-butyl)phenyl |
| 691 | 2-chloro-4-fluorophenyl | F | H | H | H | 2,6-dimethyl-4-(nonafluoro-2-butyl)phenyl |
| 692 | 2-chloro-6-fluorophenyl | F | H | H | H | 2,6-dimethyl-4-(nonafluoro-2-butyl)phenyl |
| 693 | 4-chloro-2-fluorophenyl | F | H | H | H | 2,6-dimethyl-4-(nonafluoro-2-butyl)phenyl |
| 694 | 4-chloro-2-nitrophenyl | F | H | H | H | 2,6-dimethyl-4-(nonafluoro-2-butyl)phenyl |
| 695 | 2,3,6-trifluorophenyl | F | H | H | H | 2,6-dimethyl-4-(nonafluoro-2-butyl)phenyl |
| 696 | pyridin-2-yl | F | H | H | H | 2,6-dimethyl-4-(nonafluoro-2-butyl)phenyl |
| 697 | pyridin-3-yl | F | H | H | H | 2,6-dimethyl-4-(nonafluoro-2-butyl)phenyl |
| 698 | 2-fluoropyridin-3-yl | F | H | H | H | 2,6-dimethyl-4-(nonafluoro-2-butyl)phenyl |
| 699 | 2-chloropyridin-3-yl | F | H | H | H | 2,6-dimethyl-4-(nonafluoro-2-butyl)phenyl |
| 700 | 2-chloropyridin-5-yl | F | H | H | H | 2,6-dimethyl-4-(nonafluoro-2-butyl)phenyl |
| 701 | 2-methylthiopyridin-3-yl | F | H | H | H | 2,6-dimethyl-4-(nonafluoro-2-butyl)phenyl |
| 702 | pyrazin-2-yl | F | H | H | H | 2,6-dimethyl-4-(nonafluoro-2-butyl)phenyl |
| 703 | furan-2-yl | F | H | H | H | 2,6-dimethyl-4-(nonafluoro-2-butyl)phenyl |
| 704 | furan-3-yl | F | H | H | H | 2,6-dimethyl-4-(nonafluoro-2-butyl)phenyl |
| 705 | 2-tetrahydrofuranyl | F | H | H | H | 2,6-dimethyl-4-(nonafluoro-2-butyl)phenyl |
| 706 | benzofuran-2-yl | F | H | H | H | 2,6-dimethyl-4-(nonafluoro-2-butyl)phenyl |

TABLE 2-continued

| Compound No. | Q1 | X1 | X2 | X3 | X4 | Q2 |
|---|---|---|---|---|---|---|
| 707 | thiophen-2-yl | F | H | H | H | 2,6-dimethyl-4-(nonafluoro-2-butyl)phenyl |
| 708 | phenyl | F | H | H | H | 2,6-dibromo-4-(heptafluoro-n-propylthio)phenyl |
| 709 | 2-methylphenyl | F | H | H | H | 2,6-dibromo-4-(heptafluoro-n-propylthio)phenyl |
| 710 | 4-methylphenyl | F | H | H | H | 2,6-dibromo-4-(heptafluoro-n-propylthio)phenyl |
| 711 | 2-fluorophenyl | F | H | H | H | 2,6-dibromo-4-(heptafluoro-n-propylthio)phenyl |
| 712 | 3-fluorophenyl | F | H | H | H | 2,6-dibromo-4-(heptafluoro-n-propylthio)phenyl |
| 713 | 4-fluorophenyl | F | H | H | H | 2,6-dibromo-4-(heptafluoro-n-propylthio)phenyl |
| 714 | 2-chorophenyl | F | H | H | H | 2,6-dibromo-4-(heptafluoro-n-propylthio)phenyl |
| 715 | 4-chorophenyl | F | H | H | H | 2,6-dibromo-4-(heptafluoro-n-propylthio)phenyl |
| 716 | 2-bromophenyl | F | H | H | H | 2,6-dibromo-4-(heptafluoro-n-propylthio)phenyl |
| 717 | 2-iodophenyl | F | H | H | H | 2,6-dibromo-4-(heptafluoro-n-propylthio)phenyl |
| 718 | 3-cyanophenyl | F | H | H | H | 2,6-dibromo-4-(heptafluoro-n-propylthio)phenyl |
| 719 | 4-cyanophenyl | F | H | H | H | 2,6-dibromo-4-(heptafluoro-n-propylthio)phenyl |
| 720 | 2-nitrophenyl | F | H | H | H | 2,6-dibromo-4-(heptafluoro-n-propylthio)phenyl |
| 721 | 3-nitrophenyl | F | H | H | H | 2,6-dibromo-4-(heptafluoro-n-propylthio)phenyl |
| 722 | 4-nitrophenyl | F | H | H | H | 2,6-dibromo-4-(heptafluoro-n-propylthio)phenyl |
| 723 | 2-trifluoromethylphenyl | F | H | H | H | 2,6-dibromo-4-(heptafluoro-n-propylthio)phenyl |
| 724 | 4-trifluoromethylphenyl | F | H | H | H | 2,6-dibromo-4-(heptafluoro-n-propylthio)phenyl |
| 725 | 4-trifluoromethoxyphenyl | F | H | H | H | 2,6-dibromo-4-(heptafluoro-n-propylthio)phenyl |
| 726 | 2,3-difluorophenyl | F | H | H | H | 2,6-dibromo-4-(heptafluoro-n-propylthio)phenyl |
| 727 | 2,4-difluorophenyl | F | H | H | H | 2,6-dibromo-4-(heptafluoro-n-propylthio)phenyl |
| 728 | 2,5-difluorophenyl | F | H | H | H | 2,6-dibromo-4-(heptafluoro-n-propylthio)phenyl |
| 729 | 2,6-difluorophenyl | F | H | H | H | 2,6-dibromo-4-(heptafluoro-n-propylthio)phenyl |
| 730 | 2,4-dichlorophenyl | F | H | H | H | 2,6-dibromo-4-(heptafluoro-n-propylthio)phenyl |
| 731 | 2,6-dichlorophenyl | F | H | H | H | 2,6-dibromo-4-(heptafluoro-n-propylthio)phenyl |
| 732 | 3,4-dichlorophenyl | F | H | H | H | 2,6-dibromo-4-(heptafluoro-n-propylthio)phenyl |
| 733 | 2-chloro-4-nitrophenyl | F | H | H | H | 2,6-dibromo-4-(heptafluoro-n-propylthio)phenyl |
| 734 | 2-chloro-4-fluorophenyl | F | H | H | H | 2,6-dibromo-4-(heptafluoro-n-propylthio)phenyl |
| 735 | 2-chloro-6-fluorophenyl | F | H | H | H | 2,6-dibromo-4-(heptafluoro-n-propylthio)phenyl |
| 736 | 4-chloro-2-fluorophenyl | F | H | H | H | 2,6-dibromo-4-(heptafluoro-n-propylthio)phenyl |
| 737 | 4-chloro-2-nitrophenyl | F | H | H | H | 2,6-dibromo-4-(heptafluoro-n-propylthio)phenyl |
| 738 | 2,3,6-trifluorophenyl | F | H | H | H | 2,6-dibromo-4-(heptafluoro-n-propylthio)phenyl |
| 739 | pyridin-2-yl | F | H | H | H | 2,6-dibromo-4-(heptafluoro-n-propylthio)phenyl |
| 740 | pyridin-3-yl | F | H | H | H | 2,6-dibromo-4-(heptafluoro-n-propylthio)phenyl |
| 741 | 2-fluoropyridin-3-yl | F | H | H | H | 2,6-dibromo-4-(heptafluoro-n-propylthio)phenyl |
| 742 | 2-chloropyridin-3-yl | F | H | H | H | 2,6-dibromo-4-(heptafluoro-n-propylthio)phenyl |
| 743 | 2-chloropyridin-5-yl | F | H | H | H | 2,6-dibromo-4-(heptafluoro-n-propylthio)phenyl |
| 744 | 2-methylthiopyridin-3-yl | F | H | H | H | 2,6-dibromo-4-(heptafluoro-n-propylthio)phenyl |

TABLE 2-continued

| Compound No. | Q₁ | X₁ | X₂ | X₃ | X₄ | Q₂ |
|---|---|---|---|---|---|---|
| 745 | pyrazin-2-yl | F | H | H | H | 2,6-dibromo-4-(heptafluoro-n-propylthio)phenyl |
| 746 | furan-2-yl | F | H | H | H | 2,6-dibromo-4-(heptafluoro-n-propylthio)phenyl |
| 747 | furan-3-yl | F | H | H | H | 2,6-dibromo-4-(heptafluoro-n-propylthio)phenyl |
| 748 | 2-tetrahydrofuranyl | F | H | H | H | 2,6-dibromo-4-(heptafluoro-n-propylthio)phenyl |
| 749 | benzofuran-2-yl | F | H | H | H | 2,6-dibromo-4-(heptafluoro-n-propylthio)phenyl |
| 750 | thiophen-2-yl | F | H | H | H | 2,6-dibromo-4-(heptafluoro-n-propylthio)phenyl |
| 751 | phenyl | F | H | H | H | 2,6-dibromo-4-(heptafluoro-n-propylsulfinyl)phenyl |
| 752 | 2-methylphenyl | F | H | H | H | 2,6-dibromo-4-(heptafluoro-n-propylsulfinyl)phenyl |
| 753 | 4-methylphenyl | F | H | H | H | 2,6-dibromo-4-(heptafluoro-n-propylsulfinyl)phenyl |
| 754 | 2-fluorophenyl | F | H | H | H | 2,6-dibromo-4-(heptafluoro-n-propylsulfinyl)phenyl |
| 755 | 3-fluorophenyl | F | H | H | H | 2,6-dibromo-4-(heptafluoro-n-propylsulfinyl)phenyl |
| 756 | 4-fluorophenyl | F | H | H | H | 2,6-dibromo-4-(heptafluoro-n-propylsulfinyl)phenyl |
| 757 | 2-chorophenyl | F | H | H | H | 2,6-dibromo-4-(heptafluoro-n-propylsulfinyl)phenyl |
| 758 | 4-chorophenyl | F | H | H | H | 2,6-dibromo-4-(heptafluoro-n-propylsulfinyl)phenyl |
| 759 | 2-bromophenyl | F | H | H | H | 2,6-dibromo-4-(heptafluoro-n-propylsulfinyl)phenyl |
| 760 | 2-iodophenyl | F | H | H | H | 2,6-dibromo-4-(heptafluoro-n-propylsulfinyl)phenyl |
| 761 | 3-cyanophenyl | F | H | H | H | 2,6-dibromo-4-(heptafluoro-n-propylsulfinyl)phenyl |
| 762 | 4-cyanophenyl | F | H | H | H | 2,6-dibromo-4-(heptafluoro-n-propylsulfinyl)phenyl |
| 763 | 2-nitrophenyl | F | H | H | H | 2,6-dibromo-4-(heptafluoro-n-propylsulfinyl)phenyl |
| 764 | 3-nitrophenyl | F | H | H | H | 2,6-dibromo-4-(heptafluoro-n-propylsulfinyl)phenyl |
| 765 | 4-nitrophenyl | F | H | H | H | 2,6-dibromo-4-(heptafluoro-n-propylsulfinyl)phenyl |
| 766 | 2-trifluoromethylphenyl | F | H | H | H | 2,6-dibromo-4-(heptafluoro-n-propylsulfinyl)phenyl |
| 767 | 4-trifluoromethylphenyl | F | H | H | H | 2,6-dibromo-4-(heptafluoro-n-propylsulfinyl)phenyl |
| 768 | 4-trifluoromethoxyphenyl | F | H | H | H | 2,6-dibromo-4-(heptafluoro-n-propylsulfinyl)phenyl |
| 769 | 2,3-difluorophenyl | F | H | H | H | 2,6-dibromo-4-(heptafluoro-n-propylsulfinyl)phenyl |
| 770 | 2,4-difluorophenyl | F | H | H | H | 2,6-dibromo-4-(heptafluoro-n-propylsulfinyl)phenyl |
| 771 | 2,5-difluorophenyl | F | H | H | H | 2,6-dibromo-4-(heptafluoro-n-propylsulfinyl)phenyl |
| 772 | 2,6-difluorophenyl | F | H | H | H | 2,6-dibromo-4-(heptafluoro-n-propylsulfinyl)phenyl |
| 773 | 2,4-dichlorophenyl | F | H | H | H | 2,6-dibromo-4-(heptafluoro-n-propylsulfinyl)phenyl |
| 774 | 2,6-dichlorophenyl | F | H | H | H | 2,6-dibromo-4-(heptafluoro-n-propylsulfinyl)phenyl |
| 775 | 3,4-dichlorophenyl | F | H | H | H | 2,6-dibromo-4-(heptafluoro-n-propylsulfinyl)phenyl |
| 776 | 2-chloro-4-nitrophenyl | F | H | H | H | 2,6-dibromo-4-(heptafluoro-n-propylsulfinyl)phenyl |
| 777 | 2-chloro-4-fluorophenyl | F | H | H | H | 2,6-dibromo-4-(heptafluoro-n-propylsulfinyl)phenyl |
| 778 | 2-chloro-6-fluorophenyl | F | H | H | H | 2,6-dibromo-4-(heptafluoro-n-propylsulfinyl)phenyl |
| 779 | 4-chloro-2-fluorophenyl | F | H | H | H | 2,6-dibromo-4-(heptafluoro-n-propylsulfinyl)phenyl |
| 780 | 4-chloro-2-nitrophenyl | F | H | H | H | 2,6-dibromo-4-(heptafluoro-n-propylsulfinyl)phenyl |
| 781 | 2,3,6-trifluorophenyl | F | H | H | H | 2,6-dibromo-4-(heptafluoro-n-propylsulfinyl)phenyl |
| 782 | pyridin-2-yl | F | H | H | H | 2,6-dibromo-4-(heptafluoro-n-propylsulfinyl)phenyl |

TABLE 2-continued

| Compound No. | Q1 | X1 | X2 | X3 | X4 | Q2 |
|---|---|---|---|---|---|---|
| 783 | pyridin-3-yl | F | H | H | H | 2,6-dibromo-4-(heptafluoro-n-propylsulfinyl)phenyl |
| 784 | 2-fluoropyridin-3-yl | F | H | H | H | 2,6-dibromo-4-(heptafluoro-n-propylsulfinyl)phenyl |
| 785 | 2-chloropyridin-3-yl | F | H | H | H | 2,6-dibromo-4-(heptafluoro-n-propylsulfinyl)phenyl |
| 786 | 2-chloropyridin-5-yl | F | H | H | H | 2,6-dibromo-4-(heptafluoro-n-propylsulfinyl)phenyl |
| 787 | 2-methylthiopyridin-3-yl | F | H | H | H | 2,6-dibromo-4-(heptafluoro-n-propylsulfinyl)phenyl |
| 788 | pyrazin-2-yl | F | H | H | H | 2,6-dibromo-4-(heptafluoro-n-propylsulfinyl)phenyl |
| 789 | furan-2-yl | F | H | H | H | 2,6-dibromo-4-(heptafluoro-n-propylsulfinyl)phenyl |
| 790 | thiophen-2-yl | F | H | H | H | 2,6-dibromo-4-(heptafluoro-n-propylsulfinyl)phenyl |
| 791 | phenyl | F | H | H | H | 2,6-dimethyl-4-(heptafluoro-n-propylthio)phenyl |
| 792 | 2-methylphenyl | F | H | H | H | 2,6-dimethyl-4-(heptafluoro-n-propylthio)phenyl |
| 793 | 4-methylphenyl | F | H | H | H | 2,6-dimethyl-4-(heptafluoro-n-propylthio)phenyl |
| 794 | 2-fluorophenyl | F | H | H | H | 2,6-dimethyl-4-(heptafluoro-n-propylthio)phenyl |
| 795 | 3-fluorophenyl | F | H | H | H | 2,6-dimethyl-4-(heptafluoro-n-propylthio)phenyl |
| 796 | 4-fluorophenyl | F | H | H | H | 2,6-dimethyl-4-(heptafluoro-n-propylthio)phenyl |
| 797 | 2-chorophenyl | F | H | H | H | 2,6-dimethyl-4-(heptafluoro-n-propylthio)phenyl |
| 798 | 4-chorophenyl | F | H | H | H | 2,6-dimethyl-4-(heptafluoro-n-propylthio)phenyl |
| 799 | 2-bromophenyl | F | H | H | H | 2,6-dimethyl-4-(heptafluoro-n-propylthio)phenyl |
| 800 | 2-iodophenyl | F | H | H | H | 2,6-dimethyl-4-(heptafluoro-n-propylthio)phenyl |
| 801 | 3-cyanophenyl | F | H | H | H | 2,6-dimethyl-4-(heptafluoro-n-propylthio)phenyl |
| 802 | 4-cyanophenyl | F | H | H | H | 2,6-dimethyl-4-(heptafluoro-n-propylthio)phenyl |
| 803 | 2-nitrophenyl | F | H | H | H | 2,6-dimethyl-4-(heptafluoro-n-propylthio)phenyl |
| 804 | 3-nitrophenyl | F | H | H | H | 2,6-dimethyl-4-(heptafluoro-n-propylthio)phenyl |
| 805 | 4-nitrophenyl | F | H | H | H | 2,6-dimethyl-4-(heptafluoro-n-propylthio)phenyl |
| 806 | 2-trifluoromethyl phenyl | F | H | H | H | 2,6-dimethyl-4-(heptafluoro-n-propylthio)phenyl |
| 807 | 4-trifluoromethyl phenyl | F | H | H | H | 2,6-dimethyl-4-(heptafluoro-n-propylthio)phenyl |
| 808 | 4-trifluoromethoxy phenyl | F | H | H | H | 2,6-dimethyl-4-(heptafluoro-n-propylthio)phenyl |
| 809 | 2,3-difluorophenyl | F | H | H | H | 2,6-dimethyl-4-(heptafluoro-n-propylthio)phenyl |
| 810 | 2,4-difluorophenyl | F | H | H | H | 2,6-dimethyl-4-(heptafluoro-n-propylthio)phenyl |
| 811 | 2,5-difluorophenyl | F | H | H | H | 2,6-dimethyl-4-(heptafluoro-n-propylthio)phenyl |
| 812 | 2,6-difluorophenyl | F | H | H | H | 2,6-dimethyl-4-(heptafluoro-n-propylthio)phenyl |
| 813 | 2,4-dichlorophenyl | F | H | H | H | 2,6-dimethyl-4-(heptafluoro-n-propylthio)phenyl |
| 814 | 2,6-dichlorophenyl | F | H | H | H | 2,6-dimethyl-4-(heptafluoro-n-propylthio)phenyl |
| 815 | 3,4-dichlorophenyl | F | H | H | H | 2,6-dimethyl-4-(heptafluoro-n-propylthio)phenyl |
| 816 | 2-chloro-4-nitrophenyl | F | H | H | H | 2,6-dimethyl-4-(heptafluoro-n-propylthio)phenyl |
| 817 | 2-chloro-4-fluorophenyl | F | H | H | H | 2,6-dimethyl-4-(heptafluoro-n-propylthio)phenyl |
| 818 | 2-chloro-6-fluorophenyl | F | H | H | H | 2,6-dimethyl-4-(heptafluoro-n-propylthio)phenyl |
| 819 | 4-chloro-2-fluorophenyl | F | H | H | H | 2,6-dimethyl-4-(heptafluoro-n-propylthio)phenyl |
| 820 | 4-chloro-2-nitrophenyl | F | H | H | H | 2,6-dimethyl-4-(heptafluoro-n-propylthio)phenyl |

TABLE 2-continued

| Compound No. | $Q_1$ | $X_1$ | $X_2$ | $X_3$ | $X_4$ | $Q_2$ |
|---|---|---|---|---|---|---|
| 821 | 2,3,6-trifluorophenyl | F | H | H | H | 2,6-dimethyl-4-(heptafluoro-n-propylthio)phenyl |
| 822 | pyridin-2-yl | F | H | H | H | 2,6-dimethyl-4-(heptafluoro-n-propylthio)phenyl |
| 823 | pyridin-3-yl | F | H | H | H | 2,6-dimethyl-4-(heptafluoro-n-propylthio)phenyl |
| 824 | 2-fluoropyridin-3-yl | F | H | H | H | 2,6-dimethyl-4-(heptafluoro-n-propylthio)phenyl |
| 825 | 2-chloropyridin-3-yl | F | H | H | H | 2,6-dimethyl-4-(heptafluoro-n-propylthio)phenyl |
| 826 | 2-chloropyridin-5-yl | F | H | H | H | 2,6-dimethyl-4-(heptafluoro-n-propylthio)phenyl |
| 827 | 2-methylthiopyridin-3-yl | F | H | H | H | 2,6-dimethyl-4-(heptafluoro-n-propylthio)phenyl |
| 828 | pyrazin-2-yl | F | H | H | H | 2,6-dimethyl-4-(heptafluoro-n-propylthio)phenyl |
| 829 | furan-2-yl | F | H | H | H | 2,6-dimethyl-4-(heptafluoro-n-propylthio)phenyl |
| 830 | thiophen-2-yl | F | H | H | H | 2,6-dimethyl-4-(heptafluoro-n-propylthio)phenyl |
| 831 | phenyl | Cl | H | H | H | 2,6-dimethyl-4-(heptafluoro-n-propylthio)phenyl |
| 832 | 2-fluorophenyl | Cl | H | H | H | 2,6-dimethyl-4-(heptafluoro-n-propylthio)phenyl |
| 833 | 2-chloropyridin-3-yl | Cl | H | H | H | 2,6-dimethyl-4-(heptafluoro-n-propylthio)phenyl |

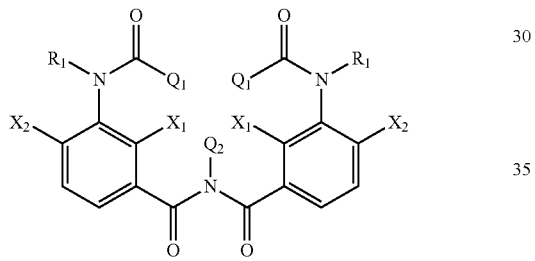

TABLE 3

| Compound No. | $Q_1$ | $R_1$ | $X_1$ | $X_2$ | $Q_2$ |
|---|---|---|---|---|---|
| 834 | phenyl | Me | H | H | 2,6-dimethyl-4-(heptafluoroisopropyl)phenyl |
| 835 | 2-methylphenyl | Me | H | H | 2,6-dimethyl-4-(heptafluoroisopropyl)phenyl |
| 836 | 4-methylphenyl | Me | H | H | 2,6-dimethyl-4-(heptafluoroisopropyl)phenyl |
| 837 | 2-fluorophenyl | Me | H | H | 2,6-dimethyl-4-(heptafluoroisopropyl)phenyl |
| 838 | 3-fluorophenyl | Me | H | H | 2,6-dimethyl-4-(heptafluoroisopropyl)phenyl |
| 839 | 4-fluorophenyl | Me | H | H | 2,6-dimethyl-4-(heptafluoroisopropyl)phenyl |
| 840 | 2-chorophenyl | Me | H | H | 2,6-dimethyl-4-(heptafluoroisopropyl)phenyl |
| 841 | 4-chorophenyl | Me | H | H | 2,6-dimethyl-4-(heptafluoroisopropyl)phenyl |
| 842 | 2-bromophenyl | Me | H | H | 2,6-dimethyl-4-(heptafluoroisopropyl)phenyl |
| 843 | 2-iodophenyl | Me | H | H | 2,6-dimethyl-4-(heptafluoroisopropyl)phenyl |
| 844 | 3-cyanophenyl | Me | H | H | 2,6-dimethyl-4-(heptafluoroisopropyl)phenyl |
| 845 | 4-cyanophenyl | Me | H | H | 2,6-dimethyl-4-(heptafluoroisopropyl)phenyl |
| 846 | 2-nitrophenyl | Me | H | H | 2,6-dimethyl-4-(heptafluoroisopropyl)phenyl |

TABLE 3-continued

| Compound No. | Q₁ | R₁ | X₁ | X₂ | Q₂ |
|---|---|---|---|---|---|
| 847 | 3-nitrophenyl | Me | H | H | 2,6-dimethyl-4-(heptafluoroisopropyl)phenyl |
| 848 | 4-nitrophenyl | Me | H | H | 2,6-dimethyl-4-(heptafluoroisopropyl)phenyl |
| 849 | 2-trifluoromethylphenyl | Me | H | H | 2,6-dimethyl-4-(heptafluoroisopropyl)phenyl |
| 850 | 4-trifluoromethylphenyl | Me | H | H | 2,6-dimethyl-4-(heptafluoroisopropyl)phenyl |
| 851 | 4-trifluoromethoxyphenyl | Me | H | H | 2,6-dimethyl-4-(heptafluoroisopropyl)phenyl |
| 852 | 2,3-difluorophenyl | Me | H | H | 2,6-dimethyl-4-(heptafluoroisopropyl)phenyl |
| 853 | 2,4-difluorophenyl | Me | H | H | 2,6-dimethyl-4-(heptafluoroisopropyl)phenyl |
| 854 | 2,5-difluorophenyl | Me | H | H | 2,6-dimethyl-4-(heptafluoroisopropyl)phenyl |
| 855 | 2,6-difluorophenyl | Me | H | H | 2,6-dimethyl-4-(heptafluoroisopropyl)phenyl |
| 856 | 2,4-dichlorophenyl | Me | H | H | 2,6-dimethyl-4-(heptafluoroisopropyl)phenyl |
| 857 | 2,6-dichlorophenyl | Me | H | H | 2,6-dimethyl-4-(heptafluoroisopropyl)phenyl |
| 858 | 3,4-dichlorophenyl | Me | H | H | 2,6-dimethyl-4-(heptafluoroisopropyl)phenyl |
| 859 | 2-chloro-4-nitrophenyl | Me | H | H | 2,6-dimethyl-4-(heptafluoroisopropyl)phenyl |
| 860 | 2-chloro-4-fluorophenyl | Me | H | H | 2,6-dimethyl-4-(heptafluoroisopropyl)phenyl |
| 861 | 2-chloro-6-fluorophenyl | Me | H | H | 2,6-dimethyl-4-(heptafluoroisopropyl)phenyl |
| 862 | 4-chloro-2-fluorophenyl | Me | H | H | 2,6-dimethyl-4-(heptafluoroisopropyl)phenyl |
| 863 | 4-chloro-2-nitrophenyl | Me | H | H | 2,6-dimethyl-4-(heptafluoroisopropyl)phenyl |
| 864 | 2,3,6-trifluorophenyl | Me | H | H | 2,6-dimethyl-4-(heptafluoroisopropyl)phenyl |
| 865 | 3-(acetylamino)phenyl | Me | H | H | 2,6-dimethyl-4-(heptafluoroisopropyl)phenyl |
| 866 | pyridin-2-yl | Me | H | H | 2,6-dimethyl-4-(heptafluoroisopropyl)phenyl |
| 867 | pyridin-3-yl | Me | H | H | 2,6-dimethyl-4-(heptafluoroisopropyl)phenyl |
| 868 | 2-fluoropyridin-3-yl | Me | H | H | 2,6-dimethyl-4-(heptafluoroisopropyl)phenyl |
| 869 | 2-chloropyridin-3-yl | Me | H | H | 2,6-dimethyl-4-(heptafluoroisopropyl)phenyl |
| 870 | 2-chloropyridin-5-yl | Me | H | H | 2,6-dimethyl-4-(heptafluoroisopropyl)phenyl |
| 871 | 2-trifluoromethylpyridin-3-yl | Me | H | H | 2,6-dimethyl-4-(heptafluoroisopropyl)phenyl |
| 872 | 2-methylthiopyridin-3-yl | Me | H | H | 2,6-dimethyl-4-(heptafluoroisopropyl)phenyl |
| 873 | pyrazin-2-yl | Me | H | H | 2,6-dimethyl-4-(heptafluoroisopropyl)phenyl |
| 874 | furan-2-yl | Me | H | H | 2,6-dimethyl-4-(heptafluoroisopropyl)phenyl |
| 875 | furan-3-yl | Me | H | H | 2,6-dimethyl-4-(heptafluoroisopropyl)phenyl |
| 876 | 2-tetrahydrofuranyl | Me | H | H | 2,6-dimethyl-4-(heptafluoroisopropyl)phenyl |
| 877 | benzofuran-2-yl | Me | H | H | 2,6-dimethyl-4-(heptafluoroisopropyl)phenyl |
| 878 | thiophen-2-yl | Me | H | H | 2,6-dimethyl-4-(heptafluoroisopropyl)phenyl |
| 879 | phenyl | Me | H | H | 2-bromo-4-(heptafluoroisopropyl)-6-(methylsulfonyl)phenyl |
| 880 | 2-methylphenyl | Me | H | H | 2-bromo-4-(heptafluoroisopropyl)-6-(methylsulfonyl)phenyl |
| 881 | 4-methylphenyl | Me | H | H | 2-bromo-4-(heptafluoroisopropyl)-6-(methylsulfonyl)phenyl |
| 882 | 2-fluorophenyl | Me | H | H | 2-bromo-4-(heptafluoroisopropyl)-6-(methylsulfonyl)phenyl |
| 883 | 3-fluorophenyl | Me | H | H | 2-bromo-4-(heptafluoroisopropyl)-6-(methylsulfonyl)phenyl |
| 884 | 4-fluorophenyl | Me | H | H | 2-bromo-4-(heptafluoroisopropyl)-6-(methylsulfonyl)phenyl |

TABLE 3-continued

| Compound No. | Q1 | R1 | X1 | X2 | Q2 |
|---|---|---|---|---|---|
| 885 | 2-chorophenyl | Me | H | H | 2-bromo-4-(heptafluoroisopropyl)-6-(methylsulfonyl)phenyl |
| 886 | 4-chorophenyl | Me | H | H | 2-bromo-4-(heptafluoroisopropyl)-6-(methylsulfonyl)phenyl |
| 887 | 2-bromophenyl | Me | H | H | 2-bromo-4-(heptafluoroisopropyl)-6-(methylsulfonyl)phenyl |
| 888 | 2-iodophenyl | Me | H | H | 2-bromo-4-(heptafluoroisopropyl)-6-(methylsulfonyl)phenyl |
| 889 | 3-cyanophenyl | Me | H | H | 2-bromo-4-(heptafluoroisopropyl)-6-(methylsulfonyl)phenyl |
| 890 | 4-cyanophenyl | Me | H | H | 2-bromo-4-(heptafluoroisopropyl)-6-(methylsulfonyl)phenyl |
| 891 | 2-nitrophenyl | Me | H | H | 2-bromo-4-(heptafluoroisopropyl)-6-(methylsulfonyl)phenyl |
| 892 | 3-nitrophenyl | Me | H | H | 2-bromo-4-(heptafluoroisopropyl)-6-(methylsulfonyl)phenyl |
| 893 | 4-nitrophenyl | Me | H | H | 2-bromo-4-(heptafluoroisopropyl)-6-(methylsulfonyl)phenyl |
| 894 | 2-trifluoromethylphenyl | Me | H | H | 2-bromo-4-(heptafluoroisopropyl)-6-(methylsulfonyl)phenyl |
| 895 | 4-trifluoromethylphenyl | Me | H | H | 2-bromo-4-(heptafluoroisopropyl)-6-(methylsulfonyl)phenyl |
| 896 | 4-trifluoromethoxyphenyl | Me | H | H | 2-bromo-4-(heptafluoroisopropyl)-6-(methylsulfonyl)phenyl |
| 897 | 2,3-difluorophenyl | Me | H | H | 2-bromo-4-(heptafluoroisopropyl)-6-(methylsulfonyl)phenyl |
| 898 | 2,4-difluorophenyl | Me | H | H | 2-bromo-4-(heptafluoroisopropyl)-6-(methylsulfonyl)phenyl |
| 899 | 2,5-difluorophenyl | Me | H | H | 2-bromo-4-(heptafluoroisopropyl)-6-(methylsulfonyl)phenyl |
| 900 | 2,6-difluorophenyl | Me | H | H | 2-bromo-4-(heptafluoroisopropyl)-6-(methylsulfonyl)phenyl |
| 901 | 2,4-dichlorophenyl | Me | H | H | 2-bromo-4-(heptafluoroisopropyl)-6-(methylsulfonyl)phenyl |
| 902 | 2,6-dichlorophenyl | Me | H | H | 2-bromo-4-(heptafluoroisopropyl)-6-(methylsulfonyl)phenyl |
| 903 | 3,4-dichlorophenyl | Me | H | H | 2-bromo-4-(heptafluoroisopropyl)-6-(methylsulfonyl)phenyl |
| 904 | 2-chloro-4-nitrophenyl | Me | H | H | 2-bromo-4-(heptafluoroisopropyl)-6-(methylsulfonyl)phenyl |
| 905 | 2-chloro-4-fluorophenyl | Me | H | H | 2-bromo-4-(heptafluoroisopropyl)-6-(methylsulfonyl)phenyl |
| 906 | 2-chloro-6-fluorophenyl | Me | H | H | 2-bromo-4-(heptafluoroisopropyl)-6-(methylsulfonyl)phenyl |
| 907 | 4-chloro-2-fluorophenyl | Me | H | H | 2-bromo-4-(heptafluoroisopropyl)-6-(methylsulfonyl)phenyl |
| 908 | 4-chloro-2-nitrophenyl | Me | H | H | 2-bromo-4-(heptafluoroisopropyl)-6-(methylsulfonyl)phenyl |
| 909 | 2,3,6-trifluorophenyl | Me | H | H | 2-bromo-4-(heptafluoroisopropyl)-6-(methylsulfonyl)phenyl |
| 910 | pyridin-2-yl | Me | H | H | 2-bromo-4-(heptafluoroisopropyl)-6-(methylsulfonyl)phenyl |
| 911 | pyridin-3-yl | Me | H | H | 2-bromo-4-(heptafluoroisopropyl)-6-(methylsulfonyl)phenyl |
| 912 | 2-fluoropyridin-3-yl | Me | H | H | 2-bromo-4-(heptafluoroisopropyl)-6-(methylsulfonyl)phenyl |
| 913 | 2-chloropyridin-3-yl | Me | H | H | 2-bromo-4-(heptafluoroisopropyl)-6-(methylsulfonyl)phenyl |
| 914 | 2-chloropyridin-5-yl | Me | H | H | 2-bromo-4-(heptafluoroisopropyl)-6-(methylsulfonyl)phenyl |
| 915 | 2-methylthiopyridin-3-yl | Me | H | H | 2-bromo-4-(heptafluoroisopropyl)-6-(methylsulfonyl)phenyl |
| 916 | pyrazin-2-yl | Me | H | H | 2-bromo-4-(heptafluoroisopropyl)-6-(methylsulfonyl)phenyl |
| 917 | furan-2-yl | Me | H | H | 2-bromo-4-(heptafluoroisopropyl)-6-(methylsulfonyl)phenyl |
| 918 | thiophen-2-yl | Me | H | H | 2-bromo-4-(heptafluoroisopropyl)-6-(methylsulfonyl)phenyl |
| 919 | phenyl | Me | H | H | 2-n-propyl-6-iodo-4-(heptafluoroisopropyl)phenyl |
| 920 | 2-methylphenyl | Me | H | H | 2-n-propyl-6-iodo-4-(heptafluoroisopropyl)phenyl |
| 921 | 4-methylphenyl | Me | H | H | 2-n-propyl-6-iodo-4-(heptafluoroisopropyl)phenyl |
| 922 | 2-fluorophenyl | Me | H | H | 2-n-propyl-6-iodo-4-(heptafluoroisopropyl)phenyl |

TABLE 3-continued

| Compound No. | Q1 | R1 | X1 | X2 | Q2 |
|---|---|---|---|---|---|
| 923 | 3-fluorophenyl | Me | H | H | 2-n-propyl-6-iodo-4-(heptafluoroisopropyl)phenyl |
| 924 | 4-fluorophenyl | Me | H | H | 2-n-propyl-6-iodo-4-(heptafluoroisopropyl)phenyl |
| 925 | 2-chorophenyl | Me | H | H | 2-n-propyl-6-iodo-4-(heptafluoroisopropyl)phenyl |
| 926 | 4-chorophenyl | Me | H | H | 2-n-propyl-6-iodo-4-(heptafluoroisopropyl)phenyl |
| 927 | 2-bromophenyl | Me | H | H | 2-n-propyl-6-iodo-4-(heptafluoroisopropyl)phenyl |
| 928 | 2-iodophenyl | Me | H | H | 2-n-propyl-6-iodo-4-(heptafluoroisopropyl)phenyl |
| 929 | 3-cyanophenyl | Me | H | H | 2-n-propyl-6-iodo-4-(heptafluoroisopropyl)phenyl |
| 930 | 4-cyanophenyl | Me | H | H | 2-n-propyl-6-iodo-4-(heptafluoroisopropyl)phenyl |
| 931 | 2-nitrophenyl | Me | H | H | 2-n-propyl-6-iodo-4-(heptafluoroisopropyl)phenyl |
| 932 | 3-nitrophenyl | Me | H | H | 2-n-propyl-6-iodo-4-(heptafluoroisopropyl)phenyl |
| 933 | 4-nitrophenyl | Me | H | H | 2-n-propyl-6-iodo-4-(heptafluoroisopropyl)phenyl |
| 934 | 2-trifluoromethylphenyl | Me | H | H | 2-n-propyl-6-iodo-4-(heptafluoroisopropyl)phenyl |
| 935 | 4-trifluoromethylphenyl | Me | H | H | 2-n-propyl-6-iodo-4-(heptafluoroisopropyl)phenyl |
| 936 | 4-trifluoromethoxyphenyl | Me | H | H | 2-n-propyl-6-iodo-4-(heptafluoroisopropyl)phenyl |
| 937 | 2,3-difluorophenyl | Me | H | H | 2-n-propyl-6-iodo-4-(heptafluoroisopropyl)phenyl |
| 938 | 2,4-difluorophenyl | Me | H | H | 2-n-propyl-6-iodo-4-(heptafluoroisopropyl)phenyl |
| 939 | 2,5-difluorophenyl | Me | H | H | 2-n-propyl-6-iodo-4-(heptafluoroisopropyl)phenyl |
| 940 | 2,6-difluorophenyl | Me | H | H | 2-n-propyl-6-iodo-4-(heptafluoroisopropyl)phenyl |
| 941 | 2,4-dichlorophenyl | Me | H | H | 2-n-propyl-6-iodo-4-(heptafluoroisopropyl)phenyl |
| 942 | 2,6-dichlorophenyl | Me | H | H | 2-n-propyl-6-iodo-4-(heptafluoroisopropyl)phenyl |
| 943 | 3,4-dichlorophenyl | Me | H | H | 2-n-propyl-6-iodo-4-(heptafluoroisopropyl)phenyl |
| 944 | 2-chloro-4-nitrophenyl | Me | H | H | 2-n-propyl-6-iodo-4-(heptafluoroisopropyl)phenyl |
| 945 | 2-chloro-4-fluorophenyl | Me | H | H | 2-n-propyl-6-iodo-4-(heptafluoroisopropyl)phenyl |
| 946 | 2-chloro-6-fluorophenyl | Me | H | H | 2-n-propyl-6-iodo-4-(heptafluoroisopropyl)phenyl |
| 947 | 4-chloro-2-fluorophenyl | Me | H | H | 2-n-propyl-6-iodo-4-(heptafluoroisopropyl)phenyl |
| 948 | 4-chloro-2-nitrophenyl | Me | H | H | 2-n-propyl-6-iodo-4-(heptafluoroisopropyl)phenyl |
| 949 | 2,3,6-trifluorophenyl | Me | H | H | 2-n-propyl-6-iodo-4-(heptafluoroisopropyl)phenyl |
| 950 | pyridin-2-yl | Me | H | H | 2-n-propyl-6-iodo-4-(heptafluoroisopropyl)phenyl |
| 951 | pyridin-3-yl | Me | H | H | 2-n-propyl-6-iodo-4-(heptafluoroisopropyl)phenyl |
| 952 | 2-fluoropyridin-3-yl | Me | H | H | 2-n-propyl-6-iodo-4-(heptafluoroisopropyl)phenyl |
| 953 | 2-chloropyridin-3-yl | Me | H | H | 2-n-propyl-6-iodo-4-(heptafluoroisopropyl)phenyl |
| 954 | 2-chloropyridin-5-yl | Me | H | H | 2-n-propyl-6-iodo-4-(heptafluoroisopropyl)phenyl |
| 955 | 2-methylthiopyridin-3-yl | Me | H | H | 2-n-propyl-6-iodo-4-(heptafluoroisopropyl)phenyl |
| 956 | pyrazin-2-yl | Me | H | H | 2-n-propyl-6-iodo-4-(heptafluoroisopropyl)phenyl |
| 957 | furan-2-yl | Me | H | H | 2-n-propyl-6-iodo-4-(heptafluoroisopropyl)phenyl |
| 958 | 2-fluorophenyl | Me | H | H | 2,6-dimethyl-4-(heptafluoro-n-propylthio)phenyl |
| 959 | phenyl | Me | H | H | 2,6-dibromo-4-(heptafluoro-n-propylthio)phenyl |
| 960 | 2-methylphenyl | Me | H | H | 2,6-dibromo-4-(heptafluoro-n-propylthio)phenyl |

TABLE 3-continued

| Compound No. | Q₁ | R₁ | X₁ | X₂ | Q₂ |
|---|---|---|---|---|---|
| 961 | 4-methylphenyl | Me | H | H | 2,6-dibromo-4-(heptafluoro-n-propylthio)phenyl |
| 962 | 2-fluorophenyl | Me | H | H | 2,6-dibromo-4-(heptafluoro-n-propylthio)phenyl |
| 963 | 3-fluorophenyl | Me | H | H | 2,6-dibromo-4-(heptafluoro-n-propylthio)phenyl |
| 964 | 4-fluorophenyl | Me | H | H | 2,6-dibromo-4-(heptafluoro-n-propylthio)phenyl |
| 965 | 2-chorophenyl | Me | H | H | 2,6-dibromo-4-(heptafluoro-n-propylthio)phenyl |
| 966 | 4-chorophenyl | Me | H | H | 2,6-dibromo-4-(heptafluoro-n-propylthio)phenyl |
| 967 | 2-bromophenyl | Me | H | H | 2,6-dibromo-4-(heptafluoro-n-propylthio)phenyl |
| 968 | 2-iodophenyl | Me | H | H | 2,6-dibromo-4-(heptafluoro-n-propylthio)phenyl |
| 969 | 3-cyanophenyl | Me | H | H | 2,6-dibromo-4-(heptafluoro-n-propylthio)phenyl |
| 970 | 4-cyanophenyl | Me | H | H | 2,6-dibromo-4-(heptafluoro-n-propylthio)phenyl |
| 971 | 2-nitrophenyl | Me | H | H | 2,6-dibromo-4-(heptafluoro-n-propylthio)phenyl |
| 972 | 3-nitrophenyl | Me | H | H | 2,6-dibromo-4-(heptafluoro-n-propylthio)phenyl |
| 973 | 4-nitrophenyl | Me | H | H | 2,6-dibromo-4-(heptafluoro-n-propylthio)phenyl |
| 974 | 2-trifluoromethylphenyl | Me | H | H | 2,6-dibromo-4-(heptafluoro-n-propylthio)phenyl |
| 975 | 4-trifluoromethylphenyl | Me | H | H | 2,6-dibromo-4-(heptafluoro-n-propylthio)phenyl |
| 976 | 4-trifluoromethoxyphenyl | Me | H | H | 2,6-dibromo-4-(heptafluoro-n-propylthio)phenyl |
| 977 | 2,3-difluorophenyl | Me | H | H | 2,6-dibromo-4-(heptafluoro-n-propylthio)phenyl |
| 978 | 2,4-difluorophenyl | Me | H | H | 2,6-dibromo-4-(heptafluoro-n-propylthio)phenyl |
| 979 | 2,5-difluorophenyl | Me | H | H | 2,6-dibromo-4-(heptafluoro-n-propylthio)phenyl |
| 980 | 2,6-difluorophenyl | Me | H | H | 2,6-dibromo-4-(heptafluoro-n-propylthio)phenyl |
| 981 | 2,4-dichlorophenyl | Me | H | H | 2,6-dibromo-4-(heptafluoro-n-propylthio)phenyl |
| 982 | 2,6-dichlorophenyl | Me | H | H | 2,6-dibromo-4-(heptafluoro-n-propylthio)phenyl |
| 983 | 3,4-dichlorophenyl | Me | H | H | 2,6-dibromo-4-(heptafluoro-n-propylthio)phenyl |
| 984 | 2-chloro-4-nitrophenyl | Me | H | H | 2,6-dibromo-4-(heptafluoro-n-propylthio)phenyl |
| 985 | 2-chloro-4-fluorophenyl | Me | H | H | 2,6-dibromo-4-(heptafluoro-n-propylthio)phenyl |
| 986 | 2-chloro-6-fluorophenyl | Me | H | H | 2,6-dibromo-4-(heptafluoro-n-propylthio)phenyl |
| 987 | 4-chloro-2-fluorophenyl | Me | H | H | 2,6-dibromo-4-(heptafluoro-n-propylthio)phenyl |
| 988 | 4-chloro-2-nitrophenyl | Me | H | H | 2,6-dibromo-4-(heptafluoro-n-propylthio)phenyl |
| 989 | 2,3,6-trifluorophenyl | Me | H | H | 2,6-dibromo-4-(heptafluoro-n-propylthio)phenyl |
| 990 | pyridin-2-yl | Me | H | H | 2,6-dibromo-4-(heptafluoro-n-propylthio)phenyl |
| 991 | pyridin-3-yl | Me | H | H | 2,6-dibromo-4-(heptafluoro-n-propylthio)phenyl |
| 992 | 2-fluoropyridin-3-yl | Me | H | H | 2,6-dibromo-4-(heptafluoro-n-propylthio)phenyl |
| 993 | 2-chloropyridin-3-yl | Me | H | H | 2,6-dibromo-4-(heptafluoro-n-propylthio)phenyl |
| 994 | 2-chloropyridin-5-yl | Me | H | H | 2,6-dibromo-4-(heptafluoro-n-propylthio)phenyl |
| 995 | 2-methylthiopyridin-3-yl | Me | H | H | 2,6-dibromo-4-(heptafluoro-n-propylthio)phenyl |
| 996 | pyrazin-2-yl | Me | H | H | 2,6-dibromo-4-(heptafluoro-n-propylthio)phenyl |
| 997 | furan-2-yl | Me | H | H | 2,6-dibromo-4-(heptafluoro-n-propylthio)phenyl |
| 998 | thiophen-2-yl | Me | H | H | 2,6-dibromo-4-(heptafluoro-n-propylthio)phenyl |

TABLE 3-continued

| Compound No. | Q₁ | R₁ | X₁ | X₂ | Q₂ |
|---|---|---|---|---|---|
| 999 | phenyl | Me | H | H | 2,6-dibromo-4-(heptafluoro-n-propylsulfinyl)phenyl |
| 1000 | 2-methylphenyl | Me | H | H | 2,6-dibromo-4-(heptafluoro-n-propylsulfinyl)phenyl |
| 1001 | 4-methylphenyl | Me | H | H | 2,6-dibromo-4-(heptafluoro-n-propylsulfinyl)phenyl |
| 1002 | 2-fluorophenyl | Me | H | It | 2,6-dibromo-4-(heptafluoro-n-propylsulfinyl)phenyl |
| 1003 | 3-fluorophenyl | Me | H | H | 2,6-dibromo-4-(heptafluoro-n-propylsulfinyl)phenyl |
| 1004 | 4-fluorophenyl | Me | H | H | 2,6-dibromo-4-(heptafluoro-n-propylsulfinyl)phenyl |
| 1005 | 2-chorophenyl | Me | H | H | 2,6-dibromo-4-(heptafluoro-n-propylsulfinyl)phenyl |
| 1006 | 4-chorophenyl | Me | H | H | 2,6-dibromo-4-(heptafluoro-n-propylsulfinyl)phenyl |
| 1007 | 2-bromophenyl | Me | H | H | 2,6-dibromo-4-(heptafluoro-n-propylsulfinyl)phenyl |
| 1008 | 2-iodophenyl | Me | H | H | 2,6-dibromo-4-(heptafluoro-n-propylsulfinyl)phenyl |
| 1009 | 3-cyanophenyl | Me | H | H | 2,6-dibromo-4-(heptafluoro-n-propylsulfinyl)phenyl |
| 1010 | 4-cyanophenyl | Me | H | H | 2,6-dibromo-4-(heptafluoro-n-propylsulfinyl)phenyl |
| 1011 | 2-nitrophenyl | Me | H | H | 2,6-dibromo-4-(heptafluoro-n-propylsulfinyl)phenyl |
| 1012 | 3-nitrophenyl | Me | H | H | 2,6-dibromo-4-(heptafluoro-n-propylsulfinyl)phenyl |
| 1013 | 4-nitrophenyl | Me | H | H | 2,6-dibromo-4-(heptafluoro-n-propylsulfinyl)phenyl |
| 1014 | 2-trifluoromethylphenyl | Me | H | H | 2,6-dibromo-4-(heptafluoro-n-propylsulfinyl)phenyl |
| 1015 | 4-trifluoromethylphenyl | Me | H | H | 2,6-dibromo-4-(heptafluoro-n-propylsulfinyl)phenyl |
| 1016 | 4-trifluoromethoxyphenyl | Me | H | H | 2,6-dibromo-4-(heptafluoro-n-propylsulfinyl)phenyl |
| 1017 | 2,3-difluorophenyl | Me | H | H | 2,6-dibromo-4-(heptafluoro-n-propylsultlnyl)phenyl |
| 1018 | 2,4-difluorophenyl | Me | H | H | 2,6-dibromo-4-(heptafluoro-n-propylsulfinyl)phenyl |
| 1019 | 2,5-difluorophenyl | Me | H | H | 2,6-dibromo-4-(heptafluoro-n-propylsulfinyl)phenyl |
| 1020 | 2,6-difluorophenyl | Me | H | H | 2,6-dibromo-4-(heptafluoro-n-propylsulfinyl)phenyl |
| 1021 | 2,4-dichlorophenyl | Me | H | H | 2,6-dibromo-4-(heptafluoro-n-propylsulfinyl)phenyl |
| 1022 | 2,6-dichlorophenyl | Me | H | H | 2,6-dibromo-4-(heptafluoro-n-propylsulfinyl)phenyl |
| 1023 | 3,4-dichlorophenyl | Me | H | H | 2,6-dibromo-4-(heptafluoro-n-propylsulfinyl)phenyl |
| 1024 | 2-chloro-4-nitrophenyl | Me | H | H | 2,6-dibromo-4-(heptafluoro-n-propylsulfinyl)phenyl |
| 1025 | 2-chloro-4-fluorophenyl | Me | H | H | 2,6-dibromo-4-(heptafluoro-n-propylsulfinyl)phenyl |
| 1026 | 2-chloro-6-fluorophenyl | Me | H | H | 2,6-dibromo-4-(heptafluoro-n-propylsulfinyl)phenyl |
| 1027 | 4-chloro-2-fluorophenyl | Me | H | H | 2,6-dibromo-4-(heptafluoro-n-propylsulfinyl)phenyl |
| 1028 | 4-chloro-2-nitrophenyl | Me | H | H | 2,6-dibromo-4-(heptafluoro-n-propylsulfinyl)phenyl |
| 1029 | 2,3,6-trifluorophenyl | Me | H | H | 2,6-dibromo-4-(heptafluoro-n-propylsulfinyl)phenyl |
| 1130 | pyridin-2-yl | Me | H | H | 2,6-dibromo-4-(heptafluoro-n-propylsulfinyl)phenyl |
| 1131 | pyridin-3-yl | Me | H | H | 2,6-dibromo-4-(heptafluoro-n-propylsulfinyl)phenyl |
| 1132 | 2-fluoropyridin-3-yl | Me | H | H | 2,6-dibromo-4-(heptafluoro-n-propylsulfinyl)phenyl |
| 1133 | 2-chloropyridin-3-yl | Me | H | H | 2,6-dibromo-4-(heptafluoro-n-propylsulfinyl)phenyl |
| 1034 | 2-chloropyridin-5-yl | Me | H | H | 2,6-dibromo-4-(heptafluoro-n-propylsulfinyl)phenyl |
| 1035 | 2-methylthiopyridin-3-yl | Me | H | H | 2,6-dibromo-4-(heptafluoro-n-propylsulfinyl)phenyl |
| 1036 | pyrazin-2-yl | Me | H | H | 2,6-dibromo-4-(heptafluoro-n-propylsulfinyl)phenyl |

TABLE 3-continued

| Compound No. | Q₁ | R₁ | X₁ | X₂ | Q₂ |
|---|---|---|---|---|---|
| 1037 | furan-2-yl | Me | H | H | 2,6-dibromo-4-(heptafluoro-n-propylsulfinyl)phenyl |
| 1038 | 2-trifluoromethylphenyl | Me | H | H | 2,6-dibromo-4-(heptafluoro-n-propylsulfinyl)phenyl |
| 1039 | 4-trifluoromethylphenyl | Et | H | H | 2,6-dimethyl-4-(heptafluoroisopropyl)phenyl |
| 1040 | 4-trifluoromethoxyphenyl | Et | H | H | 2,6-dimethyl-4-(heptafluoroisopropyl)phenyl |
| 1041 | phenyl | Me | F | H | 2,6-dimethyl-4-(heptafluoroisopropyl)phenyl |
| 1042 | 2-methylphenyl | Me | F | H | 2,6-dimethyl-4-(heptafluoroisopropyl)phenyl |
| 1043 | 3-methylphenyl | Me | F | H | 2,6-dimethyl-4-(heptafluoroisopropyl)phenyl |
| 1044 | 4-methylphenyl | Me | F | H | 2,6-dimethyl-4-(heptafluoroisopropyl)phenyl |
| 1045 | 2-nitrophenyl | Me | F | H | 2,6-dimethyl-4-(heptafluoroisopropyl)phenyl |
| 1046 | 3-nitrophenyl | Me | F | H | 2,6-dimethyl-4-(heptafluoroisopropyl)phenyl |
| 1047 | 4-nitrophenyl | Me | F | H | 2,6-dimethyl-4-(heptafluoroisopropyl)phenyl |
| 1048 | 2-cyanophenyl | Me | F | H | 2,6-dimethyl-4-(heptafluoroisopropyl)phenyl |
| 1049 | 3-cyanophenyl | Me | F | H | 2,6-dimethyl-4-(heptafluoroisopropyl)phenyl |
| 1050 | 4-cyanophenyl | Me | F | H | 2,6-dimethyl-4-(heptafluoroisopropyl)phenyl |
| 1051 | 2-fluorophenyl | Me | F | H | 2,6-dimethyl-4-(heptafluoroisopropyl)phenyl |
| 1052 | 3-fluorophenyl | Me | F | H | 2,6-dimethyl-4-(heptafluoroisopropyl)phenyl |
| 1053 | 4-fluorophenyl | Me | F | H | 2,6-dimethyl-4-(heptafluoroisopropyl)phenyl |
| 1054 | 2-chlorophenyl | Me | F | H | 2,6-dimethyl-4-(heptafluoroisopropyl)phenyl |
| 1055 | 4-chlorophenyl | Me | F | H | 2,6-dimethyl-4-(heptafluoroisopropyl)phenyl |
| 1056 | 2-bromophenyl | Me | F | H | 2,6-dimethyl-4-(heptafluoroisopropyl)phenyl |
| 1057 | 2-iodophenyl | Me | F | H | 2,6-dimethyl-4-(heptafluoroisopropyl)phenyl |
| 1058 | 3-trifluoromethylphenyl | Me | F | H | 2,6-dimethyl-4-(heptafluoroisopropyl)phenyl |
| 1059 | 2-methylthiopyridin-3-yl | Me | F | H | 2,6-dimethyl-4-(heptafluoroisopropyl)phenyl |
| 1060 | 4-trifluoromethoxyphenyl | Me | F | H | 2,6-dimethyl-4-(heptafluoroisopropyl)phenyl |
| 1061 | 2,3-difluorophenyl | Me | F | H | 2,6-dimethyl-4-(heptafluoroisopropyl)phenyl |
| 1062 | 2,4-difluorophenyl | Me | F | H | 2,6-dimethyl-4-(heptafluoroisopropyl)phenyl |
| 1063 | 2,5-difluorophenyl | Me | F | H | 2,6-dimethyl-4-(heptafluoroisopropyl)phenyl |
| 1064 | 2,6-difluorophenyl | Me | F | H | 2,6-dimethyl-4-(heptafluoroisopropyl)phenyl |
| 1065 | 2,4-dichlorophenyl | Me | F | H | 2,6-dimethyl-4-(heptafluoroisopropyl)phenyl |
| 1066 | 2,6-dichlorophenyl | Me | F | H | 2,6-dimethyl-4-(heptafluoroisopropyl)phenyl |
| 1067 | 3,4-dichlorophenyl | Me | F | H | 2,6-dimethyl-4-(heptafluoroisopropyl)phenyl |
| 1068 | 2-fluoro-4-nitrophenyl | Me | F | H | 2,6-dimethyl-4-(heptafluoroisopropyl)phenyl |
| 1069 | 4-fluoro-2-nitrophenyl | Me | F | H | 2,6-dimethyl-4-(heptafluoroisopropyl)phenyl |
| 1070 | 2-chloro-4-fluorophenyl | Me | F | H | 2,6-dimethyl-4-(heptafluoroisopropyl)phenyl |
| 1071 | 4-chloro-2-fluorophenyl | Me | F | H | 2,6-dimethyl-4-(heptafluoroisopropyl)phenyl |
| 1072 | 2-chloro-6-fluorophenyl | Me | F | H | 2,6-dimethyl-4-(heptafluoroisopropyl)phenyl |
| 1073 | 2-chloro-4-nitrophenyl | Me | F | H | 2,6-dimethyl-4-(heptafluoroisopropyl)phenyl |
| 1074 | 4-chloro-2-nitrophenyl | Me | F | H | 2,6-dimethyl-4-(heptafluoroisopropyl)phenyl |

TABLE 3-continued

| Compound No. | Q₁ | R₁ | X₁ | X₂ | Q₂ |
|---|---|---|---|---|---|
| 1075 | 2,3,6-trifluorophenyl | Me | F | H | 2,6-dimethyl-4-(heptafluoroisopropyl)phenyl |
| 1076 | pyridin-2-yl | Me | F | H | 2,6-dimethyl-4-(heptafluoroisopropyl)phenyl |
| 1077 | pyridin-3-yl | Me | F | H | 2,6-dimethyl-4-(heptafluoroisopropyl)phenyl |
| 1078 | 2-chloropyridin-3-yl | Me | F | H | 2,6-dimethyl-4-(heptafluoroisopropyl)phenyl |
| 1079 | 2-fluoropyridin-3-yl | Me | F | H | 2,6-dimethyl-4-(heptafluoroisopropyl)phenyl |
| 1080 | 2-chloropyridin-5-yl | Me | F | H | 2,6-dimethyl-4-(heptafluoroisopropyl)phenyl |
| 1081 | 2-methylthiopyridin-3-yl | Me | F | H | 2,6-dimethyl-4-(heptafluoroisopropyl)phenyl |
| 1082 | pyrazin-2-yl | Me | F | H | 2,6-dimethyl-4-(heptafluoroisopropyl)phenyl |
| 1083 | furan-2-yl | Me | F | H | 2,6-dimethyl-4-(heptafluoroisopropyl)phenyl |
| 1084 | furan-3-yl | Me | F | H | 2,6-dimethyl-4-(heptafluoroisopropyl)phenyl |
| 1085 | 2-tetrahydrofuranyl | Me | F | H | 2,6-dimethyl-4-(heptafluoroisopropyl)phenyl |
| 1086 | benzofuran-2-yl | Me | F | H | 2,6-dimethyl-4-(heptafluoroisopropyl)phenyl |
| 1087 | thiophen-2-yl | Me | F | H | 2,6-dimetliyl-4-(heptafluoroisopropyl)phenyl |
| 1088 | phenyl | Me | F | H | 2,6-dimethyl-4-(nonafluoro-2-butyl)phenyl |
| 1089 | 2-methylphenyl | Me | F | H | 2,6-dimethyl-4-(nonafluoro-2-butyl)phenyl |
| 1090 | 3-methylphenyl | Me | F | H | 2,6-dimethyl-4-(nonafluoro-2-butyl)phenyl |
| 1091 | 4-methylphenyl | Me | F | H | 2,6-dimethyl-4-(nonafluoro-2-butyl)phenyl |
| 1092 | 2-nitrophenyl | Me | F | H | 2,6-dimethyl-4-(nonafluoro-2-butyl)phenyl |
| 1093 | 3-nitrophenyl | Me | F | H | 2,6-dimethyl-4-(nonafluoro-2-butyl)phenyl |
| 1094 | 4-nitrophenyl | Me | F | H | 2,6-dimethyl-4-(nonafluoro-2-butyl)phenyl |
| 1095 | 2-cyanophenyl | Me | F | H | 2,6-dimethyl-4-(nonafluoro-2-butyl)phenyl |
| 1096 | 3-cyanophenyl | Me | F | H | 2,6-dimethyl-4-(nonafluoro-2-butyl)phenyl |
| 1097 | 4-cyanophenyl | Me | F | H | 2,6-dimethyl-4-(nonafluoro-2-butyl)phenyl |
| 1098 | 2-fluorophenyl | Me | F | H | 2,6-dimethyl-4-(nonafluoro-2-butyl)phenyl |
| 1099 | 3-fluorophenyl | Me | F | H | 2,6-dimethyl-4-(nonafluoro-2-butyl)phenyl |
| 1100 | 4-fluorophenyl | Me | F | H | 2,6-dimethyl-4-(nonafluoro-2-butyl)phenyl |
| 1101 | 2-chlorophenyl | Me | F | H | 2,6-dimethyl-4-(nonafluoro-2-butyl)phenyl |
| 1102 | 4-chlorophenyl | Me | F | H | 2,6-dimethyl-4-(nonafluoro-2-butyl)phenyl |
| 1103 | 2-bromophenyl | Me | F | H | 2,6-dimethyl-4-(nonafluoro-2-butyl)phenyl |
| 1104 | 2-iodophenyl | Me | F | H | 2,6-dimethyl-4-(nonafluoro-2-butyl)phenyl |
| 1105 | 2-trifluoromethylphenyl | Me | F | H | 2,6-dimethyl-4-(nonafluoro-2-butyl)phenyl |
| 1106 | 4-trifluoromethylphenyl | Me | F | H | 2,6-dimethyl-4-(nonafluoro-2-butyl)phenyl |
| 1107 | 4-trifluoromethoxyphenyl | Me | F | H | 2,6-dimethyl-4-(nonafluoro-2-butyl)phenyl |
| 1108 | 2,3-difluorophenyl | Me | F | H | 2,6-dimethyl-4-(nonafluoro-2-butyl)phenyl |
| 1109 | 2,4-difluorophenyl | Me | F | H | 2,6-dimethyl-4-(nonafluoro-2-butyl)phenyl |
| 1110 | 2,5-difluorophenyl | Me | F | H | 2,6-dimethyl-4-(nonafluoro-2-butyl)phenyl |
| 1111 | 2,6-difluorophenyl | Me | F | H | 2,6-dimethyl-4-(nonafluoro-2-butyl)phenyl |
| 1112 | 2,4-dichlorophenyl | Me | F | FT | 2,6-dimethyl-4-(nonafluoro-2-butyl)phenyl |

TABLE 3-continued

| Compound No. | Q₁ | R₁ | X₁ | X₂ | Q₂ |
|---|---|---|---|---|---|
| 1113 | 2,6-dichlorophenyl | Me | F | H | 2,6-dimethyl-4-(nonafluoro-2-butyl)phenyl |
| 1114 | 3,4-dichlorophenyl | Me | F | H | 2,6-dimethyl-4-(nonafluoro-2-butyl)phenyl |
| 1115 | 2-fluoro-4-nitrophenyl | Me | F | FT | 2,6-dimethyl-4-(nonafluoro-2-butyl)phenyl |
| 1116 | 4-fluoro-2-nitrophenyl | Me | F | H | 2,6-dimethyl-4-(nonafluoro-2-butyl)phenyl |
| 1117 | 2-chloro-4-fluorophenyl | Me | F | H | 2,6-dimethyl-4-(nonafluoro-2-butyl)phenyl |
| 1118 | 4-chloro-2-fluorophenyl | Me | F | H | 2,6-dimethyl-4-(nonafluoro-2-butyl)phenyl |
| 1119 | 2-chloro-6-fluorophenyl | Me | F | H | 2,6-dimethyl-4-(nonafluoro-2-butyl)phenyl |
| 1120 | 2-chloro-4-nitrophenyl | Me | F | H | 2,6-dimethyl-4-(nonafluoro-2-butyl)phenyl |
| 1121 | 4-chloro-2-nitrophenyl | Me | F | H | 2,6-dimethyl-4-(nonafluoro-2-butyl)phenyl |
| 1122 | 2,3,6-trifluorophenyl | Me | F | H | 2,6-dimethyl-4-(nonafluoro-2-butyl)phenyl |
| 1123 | pyridin-2-yl | Me | F | H | 2,6-dimethyl-4-(nonafluoro-2-butyl)phenyl |
| 1124 | pyridin-3-yl | Me | F | H | 2,6-dimethyl-4-(nonafluoro-2-butyl)phenyl |
| 1125 | 2-fluoropyridin-3-yl | Me | F | H | 2,6-dimethyl-4-(nonafluoro-2-butyl)phenyl |
| 1126 | 2-chloropyridin-3-yl | Me | F | H | 2,6-dimethyl-4-(nonafluoro-2-butyl)phenyl |
| 1127 | 2-chloropyridin-5-yl | Me | F | H | 2,6-dimethyl-4-(nonafluoro-2-butyl)phenyl |
| 1128 | 2-methylthiopyridin-3-yl | Me | F | H | 2,6-dimethyl-4-(nonafluoro-2-butyl)phenyl |
| 1129 | pyrazin-2-yl | Me | F | H | 2,6-dimethyl-4-(nonafluoro-2-butyl)phenyl |
| 1130 | furan-2-yl | Me | F | H | 2,6-dimethyl-4-(nonafluoro-2-butyl)phenyl |
| 1131 | furan-3-yl | Me | F | H | 2,6-dimethyl-4-(nonafluoro-2-butyl)phenyl |
| 1132 | 2-tetrahydrofuranyl | Me | F | H | 2,6-dimethyl-4-(nonafluoro-2-butyl)phenyl |
| 1133 | benzofuran-2-yl | Me | F | H | 2,6-dimethyl-4-(nonafluoro-2-butyl)phenyl |
| 1134 | thiophen-2-yl | Me | F | H | 2,6-dimethyl-4-(nonafluoro-2-butyl)phenyl |
| 1135 | phenyl | Me | F | H | 2-bromo-4-(heptafluoroisopropyl)-6-(methylsulfonyl)phenyl |
| 1136 | 2-methylphenyl | Me | F | H | 2-bromo-4-(heptafluoroisopropyl)-6-(methylsulfonyl)phenyl |
| 1137 | 4-methylphenyl | Me | F | H | 2-bromo-4-(heptafluoroisopropyl)-6-(methylsulfonyl)phenyl |
| 1138 | 2-fluorophenyl | Me | F | H | 2-bromo-4-(heptafluoroisopropyl)-6-(methylsulfonyl)phenyl |
| 1139 | 3-fluorophenyl | Me | F | H | 2-bromo-4-(heptafluoroisopropyl)-6-(methylsulfonyl)phenyl |
| 1140 | 4-fluorophenyl | Me | F | H | 2-bromo-4-(heptafluoroisopropyl)-6-(methylsulfonyl)phenyl |
| 1141 | 2-chlorophenyl | Me | F | H | 2-bromo-4-(heptafluoroisopropyl)-6-(methylsulfonyl)phenyl |
| 1142 | 4-chlorophenyl | Me | F | H | 2-bromo-4-(heptafluoroisopropyl)-6-(methylsulfonyl)phenyl |
| 1143 | 2-bromophenyl | Me | F | H | 2-bromo-4-(heptafluoroisopropyl)-6-(methylsulfonyl)phenyl |
| 1144 | 2-iodophenyl | Me | F | H | 2-bromo-4-(heptafluoroisopropyl)-6-(methylsulfonyl)phenyl |
| 1145 | 3-cyanophenyl | Me | F | H | 2-bromo-4-(heptafluoroisopropyl)-6-(methylsulfonyl)phenyl |
| 1146 | 4-cyanophenyl | Me | F | H | 2-bromo-4-(heptafluoroisopropyl)-6-(methylsulfonyl)phenyl |
| 1147 | 2-nitrophenyl | Me | F | H | 2-bromo-4-(heptafluoroisopropyl)-6-(methylsulfonyl)phenyl |
| 1148 | 3-nitrophenyl | Me | F | H | 2-bromo-4-(heptafluoroisopropyl)-6-(methylsulfonyl)phenyl |
| 1149 | 4-nitrophenyl | Me | F | H | 2-bromo-4-(heptafluoroisopropyl)-6-(methylsulfonyl)phenyl |
| 1150 | 2-trifluoromethylphenyl | Me | F | H | 2-bromo-4-(heptafluoroisopropyl)-6-(methylsulfonyl)phenyl |

TABLE 3-continued

| Compound No. | Q₁ | R₁ | X₁ | X₂ | Q₂ |
|---|---|---|---|---|---|
| 1151 | 4-trifluoromethylphenyl | Me | F | H | 2-bromo-4-(heptafluoroisopropyl)-6-(methylsulfonyl)phenyl |
| 1152 | 4-trifluoromethoxyphenyl | Me | F | H | 2-bromo-4-(heptafluoroisopropyl)-6-(methylsulfonyl)phenyl |
| 1153 | 2,3-difluorophenyl | Me | F | H | 2-bromo-4-(heptafluoroisopropyl)-6-(methylsulfonyl)phenyl |
| 1154 | 2,4-difluorophenyl | Me | F | H | 2-bromo-4-(heptafluoroisopropyl)-6-(methylsulfonyl)phenyl |
| 1155 | 2,5-difluorophenyl | Me | F | H | 2-bromo-4-(heptafluoroisopropyl)-6-(methylsulfonyl)phenyl |
| 1156 | 2,6-difluorophenyl | Me | F | H | 2-bromo-4-(heptafluoroisopropyl)-6-(methylsulfonyl)phenyl |
| 1157 | 2,4-dichlorophenyl | Me | F | H | 2-bromo-4-(heptafluoroisopropyl)-6-(methylsulfonyl)phenyl |
| 1158 | 2,6-dichlorophenyl | Me | F | H | 2-bromo-4-(heptafluoroisopropyl)-6-(methylsulfonyl)phenyl |
| 1159 | 3,4-dichlorophenyl | Me | F | H | 2-bromo-4-(heptafluoroisopropyl)-6-(methylsulfonyl)phenyl |
| 1160 | 2-chloro-4-nitrophenyl | Me | F | H | 2-bromo-4-(heptafluoroisopropyl)-6-(methylsulfonyl)phenyl |
| 1161 | 2-chloro-4-fluorophenyl | Me | F | H | 2-bromo-4-(heptafluoroisopropyl)-6-(methylsulfonyl)phenyl |
| 1162 | 2-chloro-6-fluorophenyl | Me | F | H | 2-bromo-4-(heptafluoroisopropyl)-6-(methylsulfonyl)phenyl |
| 1163 | 4-chloro-2-fluorophenyl | Me | F | H | 2-bromo-4-(heptafluoroisopropyl)-6-(methylsulfonyl)phenyl |
| 1164 | 4-chloro-2-nitrophenyl | Me | F | H | 2-bromo-4-(heptafluoroisopropyl)-6-(methylsulfonyl)phenyl |
| 1165 | 2,3,6-trifluorophenyl | Me | F | H | 2-bromo-4-(heptafluoroisopropyl)-6-(methylsulfonyl)phenyl |
| 1166 | pyridin-2-yl | Me | F | H | 2-bromo-4-(heptafluoroisopropyl)-6-(methylsulfonyl)phenyl |
| 1167 | pyridin-3-yl | Me | F | H | 2-bromo-4-(heptafluoroisopropyl)-6-(methylsulfonyl)phenyl |
| 1168 | 2-fluoropyridin-3-yl | Me | F | H | 2-bromo-4-(heptafluoroisopropyl)-6-(methylsulfonyl)phenyl |
| 1169 | 2-chloropyridin-3-yl | Me | F | H | 2-bromo-4-(heptafluoroisopropyl)-6-(methylsulfonyl)phenyl |
| 1170 | 2-chloropyridin-5-yl | Me | F | H | 2-bromo-4-(heptafluoroisopropyl)-6-(methylsulfonyl)phenyl |
| 1171 | 2-methylthiopyridin-3-yl | Me | F | H | 2-bromo-4-(heptafluoroisopropyl)-6-(methylsulfonyl)phenyl |
| 1172 | pyrazin-2-yl | Me | F | H | 2-bromo-4-(heptafluoroisopropyl)-6-(methylsulfonyl)phenyl |
| 1173 | furan-2-yl | Me | F | H | 2-bromo-4-(heptafluoroisopropyl)-6-(methylsulfonyl)phenyl |
| 1174 | thiophen-2-yl | Me | F | H | 2-bromo-4-(heptafluoroisopropyl)-6-(methylsulfonyl)phenyl |
| 1175 | phenyl | Me | F | H | 2-n-propyl-6-iodo-4-(heptafluoroisopropyl)phenyl |
| 1176 | 2-methylphenyl | Me | F | H | 2-n-propyl-6-iodo-4-(heptafluoroisopropyl)phenyl |
| 1177 | 4-methylphenyl | Me | F | H | 2-n-propyl-6-iodo-4-(heptafluoroisopropyl)phenyl |
| 1178 | 2-fluorophenyl | Me | F | H | 2-n-propyl-6-iodo-4-(heptafluoroisopropyl)phenyl |
| 1179 | 3-fluorophenyl | Me | F | H | 2-n-propyl-6-iodo-4-(heptafluoroisopropyl)phenyl |
| 1180 | 4-fluorophenyl | Me | F | H | 2-n-propyl-6-iodo-4-(heptafluoroisopropyl)phenyl |
| 1181 | 2-chlorophenyl | Me | F | H | 2-n-propyl-6-iodo-4-(heptafluoroisopropyl)phenyl |
| 1182 | 4-chlorophenyl | Me | F | H | 2-n-propyl-6-iodo-4-(heptafluoroisopropyl)phenyl |
| 1183 | 2-bromophenyl | Me | F | H | 2-n-propyl-6-iodo-4-(heptafluoroisopropyl)phenyl |
| 1184 | 2-iodophenyl | Me | F | H | 2-n-propyl-6-iodo-4-(heptafluoroisopropyl)phenyl |
| 1185 | 3-cyanophenyl | Me | F | H | 2-n-propyl-6-iodo-4-(heptafluoroisopropyl)phenyl |
| 1186 | 4-cyanophenyl | Me | F | H | 2-n-propyl-6-iodo-4-(heptafluoroisopropyl)phenyl |
| 1187 | 2-nitrophenyl | Me | F | H | 2-n-propyl-6-iodo-4-(heptafluoroisopropyl)phenyl |
| 1188 | 3-nitrophenyl | Me | F | H | 2-n-propyl-6-iodo-4-(heptafluoroisopropyl)phenyl |

TABLE 3-continued

| Compound No. | Q1 | R1 | X1 | X2 | Q2 |
|---|---|---|---|---|---|
| 1189 | 4-nitrophenyl | Me | F | H | 2-n-propyl-6-iodo-4-(heptafluoroisopropyl)phenyl |
| 1190 | 2-trifluoromethylphenyl | Me | F | H | 2-n-propyl-6-iodo-4-(heptafluoroisopropyl)phenyl |
| 1191 | 4-trifluoromethylphenyl | Me | F | H | 2-n-propyl-6-iodo-4-(heptafluoroisopropyl)phenyl |
| 1192 | 4-trifluoromethoxyphenyl | Me | F | H | 2-n-propyl-6-iodo-4-(heptafluoroisopropyl)phenyl |
| 1193 | 2,3-difluorophenyl | Me | F | H | 2-n-propyl-6-iodo-4-(heptafluoroisopropyl)phenyl |
| 1194 | 2,4-difluorophenyl | Me | F | H | 2-n-propyl-6-iodo-4-(heptafluoroisopropyl)phenyl |
| 1195 | 2,5-difluorophenyl | Me | F | H | 2-n-propyl-6-iodo-4-(heptafluoroisopropyl)phenyl |
| 1196 | 2,6-difluorophenyl | Me | F | H | 2-n-propyl-6-iodo-4-(heptafluoroisopropyl)phenyl |
| 1197 | 2,4-dichlorophenyl | Me | F | H | 2-n-propyl-6-iodo-4-(heptafluoroisopropyl)phenyl |
| 1198 | 2,6-dichlorophenyl | Me | F | H | 2-n-propyl-6-iodo-4-(heptafluoroisopropyl)phenyl |
| 1199 | 3,4-dichlorophenyl | Me | F | H | 2-n-propyl-6-iodo-4-(heptafluoroisopropyl)phenyl |
| 1200 | 2-chloro-4-nitrophenyl | Me | F | H | 2-n-propyl-6-iodo-4-(heptafluoroisopropyl)phenyl |
| 1201 | 2-chloro-4-fluorophenyl | Me | F | H | 2-n-propyl-6-iodo-4-(heptafluoroisopropyl)phenyl |
| 1202 | 2-chloro-6-fluorophenyl | Me | F | H | 2-n-propyl-6-iodo-4-(heptafluoroisopropyl)phenyl |
| 1203 | 4-chloro-2-fluorophenyl | Me | F | H | 2-n-propyl-6-iodo-4-(heptafluoroisopropyl)phenyl |
| 1204 | 4-chloro-2-nitrophenyl | Me | F | H | 2-n-propyl-6-iodo-4-(heptafluoroisopropyl)phenyl |
| 1205 | 2,3,6-trifluorophenyl | Me | F | H | 2-n-propyl-6-iodo-4-(heptafluoroisopropyl)phenyl |
| 1206 | pyridin-2-yl | Me | F | H | 2-n-propyl-6-iodo-4-(heptafluoroisopropyl)phenyl |
| 1207 | pyridin-3-yl | Me | F | H | 2-n-propyl-6-iodo-4-(heptafluoroisopropyl)phenyl |
| 1208 | 2-fluoropyridin-3-yl | Me | F | H | 2-n-propyl-6-iodo-4-(heptafluoroisopropyl)phenyl |
| 1209 | 2-chloropyridin-3-yl | Me | F | H | 2-n-propyl-6-iodo-4-(heptafluoroisopropyl)phenyl |
| 1210 | 2-chloropyridin-5-yl | Me | F | H | 2-n-propyl-6-iodo-4-(heptafluoroisopropyl)phenyl |
| 1211 | 2-methylthiopyridin-3-yl | Me | F | H | 2-n-propyl-6-iodo-4-(heptafluoroisopropyl)phenyl |
| 1212 | pyrazin-2-yl | Me | F | H | 2-n-propyl-6-iodo-4-(heptafluoroisopropyl)phenyl |
| 1213 | furan-2-yl | Me | F | H | 2-n-propyl-6-iodo-4-(heptafluoroisopropyl)phenyl |
| 1214 | thiophen-2-yl | Me | F | H | 2-n-propyl-6-iodo-4-(heptafluoroisopropyl)phenyl |
| 1215 | phenyl | Me | F | H | 2,6-dibromo-4-(heptafluoro-n-propylthio)phenyl |
| 1216 | 2-methylphenyl | Me | F | H | 2,6-dibromo-4-(heptafluoro-n-propylthio)phenyl |
| 1217 | 4-methylphenyl | Me | F | H | 2,6-dibromo-4-(heptafluoro-n-propylthio)phenyl |
| 1218 | 2-fluorophenyl | Me | F | H | 2,6-dibromo-4-(heptafluoro-n-propylthio)phenyl |
| 1219 | 3-fluorophenyl | Me | F | H | 2,6-dibromo-4-(heptafluoro-n-propylthio)phenyl |
| 1220 | 4-fluorophenyl | Me | F | H | 2,6-dibromo-4-(heptafluoro-n-propylthio)phenyl |
| 1221 | 2-chlorophenyl | Me | F | H | 2,6-dibromo-4-(heptafluoro-n-propylthio)phenyl |
| 1222 | 4-chlorophenyl | Me | F | H | 2,6-dibromo-4-(heptafluoro-n-propylthio)phenyl |
| 1223 | 2-bromophenyl | Me | F | H | 2,6-dibromo-4-(heptafluoro-n-propylthio)phenyl |
| 1224 | 2-iodophenyl | Me | F | H | 2,6-dibromo-4-(heptafluoro-n-propylthio)phenyl |
| 1225 | 3-cyanophenyl | Me | F | H | 2,6-dibromo-4-(heptafluoro-n-propylthio)phenyl |
| 1226 | 4-cyanophenyl | Me | F | H | 2,6-dibromo-4-(heptafluoro-n-propylthio)phenyl |

TABLE 3-continued

| Compound No. | Q₁ | R₁ | X₁ | X₂ | Q₂ |
|---|---|---|---|---|---|
| 1227 | 2-nitrophenyl | Me | F | H | 2,6-dibromo-4-(heptafluoro-n-propylthio)phenyl |
| 1228 | 3-nitrophenyl | Me | F | H | 2,6-dibromo-4-(heptafluoro-n-propylthio)phenyl |
| 1229 | 4-nitrophenyl | Me | F | H | 2,6-dibromo-4-(heptafluoro-n-propylthio)phenyl |
| 1230 | 2-trifluoromethylphenyl | Me | F | H | 2,6-dibromo-4-(heptafluoro-n-propylthio)phenyl |
| 1231 | 4-trifluoromethylphenyl | Me | F | H | 2,6-dibromo-4-(heptafluoro-n-propylthio)phenyl |
| 1232 | 4-trifluoromethoxyphenyl | Me | F | H | 2,6-dibromo-4-(heptafluoro-n-propylthio)phenyl |
| 1233 | 2,3-difluorophenyl | Me | F | H | 2,6-dibromo-4-(heptafluoro-n-propylthio)phenyl |
| 1234 | 2,4-difluorophenyl | Me | F | H | 2,6-dibromo-4-(heptafluoro-n-propylthio)phenyl |
| 1235 | 2,5-difluorophenyl | Me | F | H | 2,6-dibromo-4-(heptafluoro-n-propylthio)phenyl |
| 1236 | 2,6-difluorophenyl | Me | F | H | 2,6-dibromo-4-(heptafluoro-n-propylthio)phenyl |
| 1237 | 2,4-dichlorophenyl | Me | F | H | 2,6-dibromo-4-(heptafluoro-n-propylthio)phenyl |
| 1238 | 2,6-dichlorophenyl | Me | F | H | 2,6-dibromo-4-(heptafluoro-n-propylthio)phenyl |
| 1239 | 3,4-dichlorophenyl | Me | F | H | 2,6-dibromo-4-(heptafluoro-n-propylthio)phenyl |
| 1240 | 2-chloro-4-nitrophenyl | Me | F | H | 2,6-dibromo-4-(heptafluoro-n-propylthio)phenyl |
| 1241 | 2-chloro-4-fluorophenyl | Me | F | H | 2,6-dibromo-4-(heptafluoro-n-propylthio)phenyl |
| 1242 | 2-chloro-6-fluorophenyl | Me | F | H | 2,6-dibromo-4-(heptafluoro-n-propylthio)phenyl |
| 1243 | 4-chloro-2-fluorophenyl | Me | F | H | 2,6-dibromo-4-(heptafluoro-n-propylthio)phenyl |
| 1244 | 4-chloro-2-nitrophenyl | Me | F | H | 2,6-dibromo-4-(heptafluoro-n-propylthio)phenyl |
| 1245 | 2,3,6-trifluorophenyl | Me | F | H | 2,6-dibromo-4-(heptafluoro-n-propylthio)phenyl |
| 1246 | pyridin-2-yl | Me | F | H | 2,6-dibromo-4-(heptafluoro-n-propylthio)phenyl |
| 1247 | pyridin-3-yl | Me | F | H | 2,6-dibromo-4-(heptafluoro-n-propylthio)phenyl |
| 1248 | 2-fluoropyridin-3-yl | Me | F | H | 2,6-dibromo-4-(heptafluoro-n-propylthio)phenyl |
| 1249 | 2-chloropyridin-3-yl | Me | F | H | 2,6-dibromo-4-(heptafluoro-n-propylthio)phenyl |
| 1250 | 2-chloropyridin-5-yl | Me | F | H | 2,6-dibromo-4-(heptafluoro-n-propylthio)phenyl |
| 1251 | 2-methylthiopyridin-3-yl | Me | F | H | 2,6-dibromo-4-(heptafluoro-n-propylthio)phenyl |
| 1252 | pyrazin-2-yl | Me | F | H | 2,6-dibromo-4-(heptafluoro-n-propylthio)phenyl |
| 1253 | furan-2-yl | Me | F | H | 2,6-dibromo-4-(heptafluoro-n-propylthio)phenyl |
| 1254 | thiophen-2-yl | Me | F | H | 2,6-dibromo-4-(heptafluoro-n-propylthio)phenyl |
| 1255 | phenyl | Me | F | H | 2,6-dibromo-4-(heptafluoro-n-propylsulfinyl)phenyl |
| 1256 | 2-methylphenyl | Me | F | H | 2,6-dibromo-4-(heptafluoro-n-propylsulfinyl)phenyl |
| 1257 | 4-methylphenyl | Me | F | H | 2,6-dibromo-4-(heptafluoro-n-propylsulfinyl)phenyl |
| 1258 | 2-fluorophenyl | Me | F | H | 2,6-dibromo-4-(heptafluoro-n-propylsulfinyl)phenyl |
| 1259 | 3-fluorophenyl | Me | F | H | 2,6-dibromo-4-(heptafluoro-n-propylsulfinyl)phenyl |
| 1260 | 4-fluorophenyl | Me | F | H | 2,6-dibromo-4-(heptafluoro-n-propylsulfinyl)phenyl |
| 1261 | 2-chlorophenyl | Me | F | H | 2,6-dibromo-4-(heptafluoro-n-propylsulfinyl)phenyl |
| 1262 | 4-chlorophenyl | Me | F | H | 2,6-dibromo-4-(heptafluoro-n-propylsulfinyl)phenyl |
| 1263 | 2-bromophenyl | Me | F | H | 2,6-dibromo-4-(heptafluoro-n-propylsulfinyl)phenyl |
| 1264 | 2-iodophenyl | Me | F | H | 2,6-dibromo-4-(heptafluoro-n-propylsulfinyl)phenyl |

TABLE 3-continued

| Compound No. | Q1 | R1 | X1 | X2 | Q2 |
|---|---|---|---|---|---|
| 1265 | 3-cyanophenyl | Me | F | H | 2,6-dibromo-4-(heptafluoro-n-propylsulfinyl)phenyl |
| 1266 | 4-cyanophenyl | Me | F | H | 2,6-dibromo-4-(heptafluoro-n-propylsulfinyl)phenyl |
| 1267 | 2-nitrophenyl | Me | F | H | 2,6-dibromo-4-(heptafluoro-n-propylsulfinyl)phenyl |
| 1268 | 3-nitrophenyl | Me | F | H | 2,6-dibromo-4-(heptafluoro-n-propylsulfinyl)phenyl |
| 1269 | 4-nitrophenyl | Me | F | H | 2,6-dibromo-4-(heptafluoro-n-propylsulfinyl)phenyl |
| 1270 | 2-trifluoromethylphenyl | Me | F | H | 2,6-dibromo-4-(heptafluoro-n-propylsulfinyl)phenyl |
| 1271 | 4-trifluoromethylphenyl | Me | F | H | 2,6-dibromo-4-(heptafluoro-n-propylsulfinyl)phenyl |
| 1272 | 4-trifluoromethoxyphenyl | Me | F | H | 2,6-dibromo-4-(heptafluoro-n-propylsulfinyl)phenyl |
| 1273 | 2,3-difluorophenyl | Me | F | H | 2,6-dibromo-4-(heptafluoro-n-propylsulfinyl)phenyl |
| 1274 | 2,4-difluorophenyl | Me | F | H | 2,6-dibromo-4-(heptafluoro-n-propylsulfinyl)phenyl |
| 1275 | 2,5-difluorophenyl | Me | F | H | 2,6-dibromo-4-(heptafluoro-n-propylsulfinyl)phenyl |
| 1276 | 2,6-difluorophenyl | Me | F | H | 2,6-dibromo-4-(heptafluoro-n-propylsulfinyl)phenyl |
| 1277 | 2,4-dichlorophenyl | Me | F | H | 2,6-dibromo-4-(heptafluoro-n-propylsulfinyl)phenyl |
| 1278 | 2,6-dichlorophenyl | Me | F | H | 2,6-dibromo-4-(heptafluoro-n-propylsulfinyl)phenyl |
| 1279 | 3,4-dichlorophenyl | Me | F | H | 2,6-dibromo-4-(heptafluoro-n-propylsulfinyl)phenyl |
| 1280 | 2-chloro-4-nitrophenyl | Me | F | H | 2,6-dibromo-4-(heptafluoro-n-propylsulfinyl)phenyl |
| 1281 | 2-chloro-4-fluorophenyl | Me | F | H | 2,6-dibromo-4-(heptafluoro-n-propylsulfinyl)phenyl |
| 1282 | 2-chloro-6-fluorophenyl | Me | F | H | 2,6-dibromo-4-(heptafluoro-n-propylsulfinyl)phenyl |
| 1283 | 4-chloro-2-fluorophenyl | Me | F | H | 2,6-dibromo-4-(heptafluoro-n-propylsulfinyl)phenyl |
| 1284 | 4-chloro-2-nitrophenyl | Me | F | H | 2,6-dibromo-4-(heptafluoro-n-propylsulfinyl)phenyl |
| 1285 | 2,3,6-trifluorophenyl | Me | F | H | 2,6-dibromo-4-(heptafluoro-n-propylsulfinyl)phenyl |
| 1286 | pyridin-2-yl | Me | F | H | 2,6-dibromo-4-(heptafluoro-n-propylsulfinyl)phenyl |
| 1287 | pyridin-3-yl | Me | F | H | 2,6-dibromo-4-(heptafluoro-n-propylsulfinyl)phenyl |
| 1288 | 2-fluoropyridin-3-yl | Me | F | H | 2,6-dibromo-4-(heptafluoro-n-propylsulfinyl)phenyl |
| 1289 | 2-chloropyridin-3-yl | Me | F | H | 2,6-dibromo-4-(heptafluoro-n-propylsulfinyl)phenyl |
| 1290 | 2-chloropyridin-5-yl | Me | F | H | 2,6-dibromo-4-(heptafluoro-n-propylsulfinyl)phenyl |
| 1291 | 2-methylthiopyridin-3-yl | Me | F | H | 2,6-dibromo-4-(heptafluoro-n-propylsulfinyl)phenyl |
| 1292 | pyrazin-2-yl | Me | F | H | 2,6-dibromo-4-(heptafluoro-n-propylsulfinyl)phenyl |
| 1293 | furan-2-yl | Me | F | H | 2,6-dibromo-4-(heptafluoro-n-propylsulfinyl)phenyl |
| 1294 | thiophen-2-yl | Me | F | H | 2,6-dibromo-4-(heptafluoro-n-propylsulfinyl)phenyl |
| 1295 | phenyl | Et | F | H | 2,6-dimethyl-4-(heptafluoroisopropyl)phenyl |
| 1296 | phenyl | Me | H | F | 2,6-dimethyl-4-(heptafluoroisopropyl)phenyl |
| 1297 | 4-nitrophenyl | Me | H | F | 2,6-dimethyl-4-(heptafluoroisopropyl)phenyl |
| 1298 | 4-cyanophenyl | Me | H | F | 2,6-dimethyl-4-(heptafluoroisopropyl)phenyl |
| 1299 | phenyl | Me | H | F | 2-bromo-4-(heptafluoroisopropyl)-6-(methylsulfonyl)phenyl |
| 1300 | 4-nitrophenyl | Me | H | F | 2-bromo-4-(heptafluoroisopropyl)-6-(methylsulfonyl)phenyl |
| 1301 | 4-cyanophenyl | Me | H | F | 2-bromo-4-(heptafluoroisopropyl)-6-(methylsulfonyl)phenyl |
| 1302 | phenyl | Me | H | F | 2-n-propyl-6-iodo-4-(heptafluoroisopropyl)phenyl |

TABLE 3-continued

| Compound No. | $Q_1$ | $R_1$ | $X_1$ | $X_2$ | $Q_2$ |
|---|---|---|---|---|---|
| 1303 | 4-nitrophenyl | Me | H | F | 2-n-propyl-6-iodo-4-(heptafluoroisopropyl)phenyl |
| 1304 | 4-cyanophenyl | Me | H | F | 2-n-propyl-6-iodo-4-(heptafluoroisopropyl)phenyl |
| 1305 | phenyl | Me | H | F | 2,6-dibromo-4-(heptafluoro-n-propylthio)phenyl |
| 1306 | 4-nitrophenyl | Me | H | F | 2,6-dibromo-4-(heptafluoro-n-propylthio)phenyl |
| 1307 | 4-cyanophenyl | Me | H | F | 2,6-dibromo-4-(heptafluoro-n-propylthio)phenyl |
| 1308 | phenyl | Me | H | F | 2,6-dibromo-4-(heptafluoro-n-propylsulfonyl)phenyl |
| 1309 | 4-nitrophenyl | Me | H | F | 2,6-dibromo-4-(heptafluoro-n-propylsulfonyl)phenyl |
| 1310 | 4-cyanophenyl | Me | H | F | 2,6-dibromo-4-(heptafluoro-n-propylsulfonyl)phenyl |
| 1311 | phenyl | H | H | H | 2,6-dimethyl-4-(heptafluoroisopropyl)phenyl |
| 1312 | phenyl | H | H | H | 2-bromo-4-(heptafluoroisopropyl)-6-methylphenyl |
| 1313 | phenyl | H | H | H | 2,6-dibromo-4-(heptafluoro-n-propylthio)phenyl |

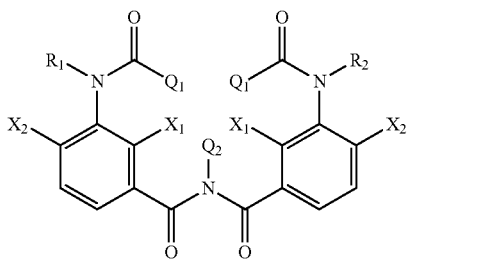

TABLE 4

| Compound No. | $Q_1$ | $R_1$ | $R_2$ | $X_1$ | $X_2$ | $Q_2$ |
|---|---|---|---|---|---|---|
| 1314 | 2-fluorophenyl | Me | H | H | H | 2,6-dibromo-4-(pentafluoroethyl)phenyl |
| 1315 | 2-fluorophenyl | Me | H | H | H | 2-bromo-4-heptafluoroisopropyl)-6-methylphenyl |
| 1316 | 2-fluorophenyl | Me | H | H | H | 2-ethyl-4-(heptafluoroisopropyl)-6-methylphenyl |
| 1317 | 2-fluorophenyl | Me | H | H | H | 4-(heptafluoroisopropyl)-2-iodo-6-methylphenyl |
| 1318 | 2-fluorophenyl | Me | H | H | H | 2-chloro-6-ethyl-4-(heptafluoroisopropyl)phenyl |
| 1319 | 2-fluorophenyl | Me | H | H | H | 2-bromo-6-ethyl-4-(heptafluoroisopropyl)phenyl |
| 1320 | 2-fluorophenyl | Me | H | H | H | 2-ethyl-4-(heptafluoroisopropyl)-6-iodophenyl |
| 1321 | 2-fluorophenyl | Me | H | H | H | 4-(heptafluoroisopropyl)-2-isopropyl-6-methylphenyl |
| 1322 | 2-fluorophenyl | Me | H | H | H | 2-bromo-4-(heptafluoroisopropyl)-6-n-propylphenyl |
| 1323 | 2-fluorophenyl | Me | H | H | H | 2-bromo-4-(heptafluoroisopropyl)-6-(trifluoromethylthio)phenyl |
| 1324 | 2-fluorophenyl | Me | H | H | H | 2,6-dibromo-4-(trifluoromethylthio)phenyl |
| 1325 | 2-fluorophenyl | Me | H | H | H | 2,6-dibromo-4-(pentafluoroethylthio)phenyl |
| 1326 | 2-fluorophenyl | Me | H | H | H | 2,6-dibromo-4-(nonafluoro-n-butylthio)phenyl |
| 1327 | 2-fluorophenyl | Me | H | H | H | 2,6-dichloro-4-(heptafluoroisopropylsulfonyl)phenyl |
| 1328 | 2-fluorophenyl | Me | H | H | H | 2,6-dibromo-4-(heptafluoro-n-propylsulfonyl)phenyl |

TABLE 4-continued

| Compound No. | Q1 | R1 | R2 | X1 | X2 | Q2 |
|---|---|---|---|---|---|---|
| 1329 | 2-fluorophenyl | Me | H | H | H | 2-bromo-6-(heptafluoroisopropyloxy)-4-methylpyridin-3-yl |
| 1330 | 2-fluorophenyl | Me | H | H | H | 2,4-dimethyl-6-(2,2,2-trifluoro-1-trifluoromethylethoxy)pyridin-3-yl |
| 1331 | 2-fluorophenyl | Me | H | H | H | 2-chloro-4-methyl-6-(2,2,2-trifluoro-1-trifluoromethylethoxy)pyridin-3-yl |
| 1332 | 2-fluorophenyl | Me | H | H | H | 2-bromo-4-methyl-6-(2,2,2-trifluoro-1-trifluoromethylethoxy)pyridin-3-yl |
| 1333 | 2-fluorophenyl | Me | H | H | H | 2-iodo-4-methyl-6-(2,2,2-trifluoro-1-trifluoromethylethoxy)pyridin-3-yl |
| 1334 | 2-fluorophenyl | Me | H | F | H | 2,6-dibromo-4-(pentafluoroethyl)phenyl |
| 1335 | 4-fluorophenyl | Me | H | F | H | 2-bromo-4-(heptafluoroisopropyl)-6-methylphenyl |
| 1336 | 4-fluorophenyl | Me | H | F | H | 2-ethyl-4-(heptafluoroisopropyl)-6-methylphenyl |
| 1337 | 4-fluorophenyl | Me | H | F | H | 4-(heptafluoroisopropyl)-2-iodo-6-methylphenyl |
| 1338 | phenyl | Me | H | F | H | 2-chloro-6-ethyl-4-(heptafluoroisopropyl)phenyl |
| 1339 | 4-fluorophenyl | Me | H | F | H | 2-bromo-6-ethyl-4-(heptafluoroisopropyl)phenyl |
| 1340 | phenyl | Me | H | F | H | 2-ethyl-4-(heptafluoroisopropyl)-6-iodophenyl |
| 1341 | phenyl | Me | H | F | H | 4-(heptafluoroisopropyl)-2-isopropyl-6-methylphenyl |
| 1342 | phenyl | Me | H | F | H | 2-bromo-4-(heptafluoroisopropyl)-6-(trifluoromethyl)phenyl |
| 1343 | phenyl | Me | H | F | H | 4-(heptafluoroisopropyl)-2-iodo-6-(trifluoromethyl)phenyl |
| 1344 | 4-fluorophenyl | Me | H | F | H | 2-bromo-4-(heptafluoroisopropyl)-6-(trifluoromethyl)phenyl |
| 1345 | 4-fluorophenyl | Me | H | F | H | 4-(heptafluoroisopropyl)-2-iodo-6-(trifluoromethyl)phenyl |
| 1346 | 2,6-difluorophenyl | Me | H | F | H | 2-bromo-4-(heptafluoroisopropyl)-6-(trifluoromethyl)phenyl |
| 1347 | 2-fluorophenyl | Me | H | F | H | 2,6-dibromo-4-(trifluoromethylthio)phenyl |
| 1348 | phenyl | Me | H | F | H | 2,6-dibromo-4-(pentafluoroethylthio)phenyl |
| 1349 | 4-fluorophenyl | Me | H | F | H | 2,6-dibromo-4-(nonafluoro-n-butylthio)phenyl |
| 1350 | 2-fluorophenyl | Me | H | F | H | 2,6-dichloro-4-(heptafluoroisopropylsulfonyl)phenyl |
| 1351 | 2-fluorophenyl | Me | H | F | H | 2,6-dibromo-4-(heptafluoro-n-propylsulfonyl)phenyl |
| 1352 | 4-fluorophenyl | Me | H | F | H | 2-bromo-6-(heptafluoroisopropyloxy)-4-methylpyridin-3-yl |
| 1353 | 2-fluorophenyl | Me | H | F | H | 2,4-dimethyl-6-(2,2,2-trifluoro-1-trifluoromethylethoxy)pyridin-3-yl |
| 1354 | 2-fuorophenyl | Me | H | F | H | 2-chloro-4-methyl-6-(2,2,2-trifluoro-1-trifluoromethylethoxy)pyridin-3-yl |
| 1355 | 2-fiuorophenyl | Me | H | F | H | 2-bromo-4-methyl-6-(2,2,2-trifluoro-1-trifluoromethylethoxy)pyridin-3-yl |
| 1356 | 2-fluorophenyl | Me | H | F | H | 2-iodo-4-methyl-6-(2,2,2-trifluoro-1-trifluoromethylethoxy)pyridin-3-yl |
| 1357 | 4-nitrophenyl | Me | H | F | H | 2-bromo-4-(heptafluoroisopropyl)-6-(trifluoromethyl)phenyl |
| 1358 | 4-nitrophenyl | Me | H | F | H | 4-(heptafluoroisopropyl)-2-iodo-6-(trifluoromethyl)phenyl |
| 1359 | phenyl | Me | H | F | H | 2,4-bis(heptafluoroisopropyl)-6-(trifluoromethyl)phenyl |
| 1360 | phenyl | Me | H | F | H | 4-bromo-2-(heptafluoroisopropyl)-6-(trifluoromethyl)phenyl |
| 1361 | phenyl | Me | H | F | H | 2,6-dibromo-4-(nonafluoro-s-butyl)-6-(trifluoromethyl)phenyl |

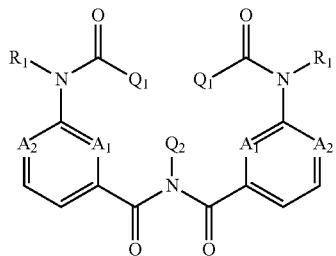

TABLE 5

| Compound No. | $Q_1$ | $R_1$ | $A_1$ | $A_2$ | $Q_2$ |
|---|---|---|---|---|---|
| 1362 | phenyl | H | N | C | 2,6-dimethyl-4-heptafluoroisopropylphenyl |
| 1363 | 2-methylphenyl | H | N | C | 2,6-dimethyl-4-heptafluoroisopropylphenyl |
| 1364 | 4-methylphenyl | H | N | C | 2,6-dimethyl-4-heptafluoroisopropylphenyl |
| 1365 | 2-fluorophenyl | H | N | C | 2,6-dimethyl-4-heptafluoroisopropylphenyl |
| 1366 | 3-fluorophenyl | H | N | C | 2,6-dimethyl-4-heptafluoroisopropylphenyl |
| 1367 | 4-fluorophenyl | H | N | C | 2,6-dimethyl-4-heptafluoroisopropylphenyl |
| 1368 | 2-chlorophenyl | H | N | C | 2,6-dimethyl-4-heptafluoroisopropylphenyl |
| 1369 | 4-chlorophenyl | H | N | C | 2,6-dimethyl-4-heptafluoroisopropylphenyl |
| 1370 | 2-bromophenyl | H | N | C | 2,6-dimethyl-4-heptafluoroisopropylphenyl |
| 1371 | 2-iodphenyl | H | N | C | 2,6-dimethyl-4-heptafluoroisopropylphenyl |
| 1372 | 3-cyanophenyl | H | N | C | 2,6-dimethyl-4-heptafluoroisopropylphenyl |
| 1373 | 4-cyanophenyl | H | N | C | 2,6-dimethyl-4-heptafluoroisopropylphenyl |
| 1374 | 2-nitrophenyl | H | N | C | 2,6-dimethyl-4-heptafluoroisopropylphenyl |
| 1375 | 3-nitrophenyl | H | N | C | 2,6-dimethyl-4-heptafluoroisopropylphenyl |
| 1376 | 4-nitrophenyl | H | N | C | 2,6-dimethyl-4-heptafluoroisopropylphenyl |
| 1377 | 2-trifluoromethylphenyl | H | N | C | 2,6-dimelhyl-4-heptafluoroisopropylphenyl |
| 1378 | 4-trifluoromethylphenyl | H | N | C | 2,6-dimethyl-4-heptafluoroisopropylphenyl |
| 1379 | 4-trifluoromethoxylphenyl | H | N | C | 2,6-dimethyl-4-heptafluoroisopropylphenyl |
| 1380 | 2,3-difluorophenyl | H | N | C | 2,6-dimethyl-4-heptafluoroisopropylphenyl |
| 1381 | 2,4-difluorophenyl | H | N | C | 2,6-dimethyl-4-heptafluoroisopropylphenyl |
| 1382 | 2,5-difluorophenyl | H | N | C | 2,6-dimethyl-4-heptafluoroisopropylphenyl |
| 1383 | 2,6-difluorophenyl | H | N | C | 2,6-dimethyl-4-heptafluoroisopropylphenyl |
| 1384 | 2,4-dichlorophenyl | H | N | C | 2,6-dimethyl-4-heptafluoroisopropylphenyl |
| 1385 | 2,6-dichlorophenyl | H | N | C | 2,6-dimethyl-4-heptafluoroisopropylphenyl |
| 1386 | 3,4-dichlorophenyl | H | N | C | 2,6-dimethyl-4-heptafluoroisopropylphenyl |
| 1387 | 2-chloro-4-nitrophenyl | H | N | C | 2,6-dimethyl-4-heptafluoroisopropylphenyl |
| 1388 | 2-chloro-4-fluorophenyl | H | N | C | 2,6-dimethyl-4-heptafluoroisopropylphenyl |
| 1389 | 2-chloro-6-fluorophenyl | H | N | C | 2,6-dimethyl-4-heptafluoroisopropylphenyl |
| 1390 | 4-chloro-2-fluorophenyl | H | N | C | 2,6-dimethyl-4-heptafluoroisopropylphenyl |
| 1391 | 4-chloro-2-nitrophenyl | H | N | C | 2,6-dimethyl-4-heptafluoroisopropylphenyl |
| 1392 | 2,3,6-trifluorophenyl | H | N | C | 2,6-dimethyl-4-heptafluoroisopropylphenyl |
| 1393 | pyridin-2-yl | H | N | C | 2,6-dimethyl-4-heptafluoroisopropylphenyl |
| 1394 | pyridin-3-yl | H | N | C | 2,6-dimethyl-4-heptafluoroisopropylphenyl |
| 1395 | pyridin-4-yl | H | N | C | 2,6-dimethyl-4-heptafluoroisopropylphenyl |
| 1396 | 2-fluoropyridin-3-yl | H | N | C | 2,6-dimethyl-4-heptafluoroisopropylphenyl |
| 1397 | 2-chloropyridin-3-yl | H | N | C | 2,6-dimethyl-4-heptafluoroisopropylphenyl |
| 1398 | 2-chloropyridin-5-yl | H | N | C | 2,6-dimethyl-4-heptafluoroisopropylphenyl |
| 1399 | 2-methylthiopyridin-3-yl | H | N | C | 2,6-dimethyl-4-heptafluoroisopropylphenyl |
| 1400 | pyrazin-2-yl | H | N | C | 2,6-dimethyl-4-heptafluoroisopropylphenyl |
| 1401 | furan-2-yl | H | N | C | 2,6-dimethyl-4-heptafluoroisopropylphenyl |
| 1402 | thiophen-2-yl | H | N | C | 2,6-dimethyl-4-heptafluoroisopropylphenyl |
| 1403 | phenyl | H | N | C | 2,6-dibromo-4-(heptafluoro-n-propylthio)phenyl |
| 1404 | 2-methylphenyl | H | N | C | 2,6-dibromo-4-(heptafluoro-n-propylthio)phenyl |
| 1405 | 4-methylphenyl | H | N | C | 2,6-dibromo-4-(heptafluoro-n-propylthio)phenyl |
| 1406 | 2-fluorophenyl | H | N | C | 2,6-dibromo-4-(heptafluoro-n-propylthio)phenyl |
| 1407 | 3-fluorophenyl | H | N | C | 2,6-dibromo-4-(heptafluoro-n-propylthio)phenyl |
| 1408 | 4-fluorophenyl | H | N | C | 2,6-dibromo-4-(heptafluoro-n-propylthio)phenyl |
| 3409 | 2-chlorophenyl | H | N | C | 2,6-dibromo-4-(heptafluoro-n-propylthio)phenyl |
| 1410 | 4-chlorophenyl | H | N | C | 2,6-dibromo-4-(heptafluoro-n-propylthio)phenyl |
| 1411 | 2-bromophenyl | H | N | C | 2,6-dibromo-4-(heptafluoro-n-propylthio)phenyl |
| 1412 | 2-iodophenyl | H | N | C | 2,6-dibromo-4-(heptafluoro-n-propylthio)phenyl |
| 1413 | 3-cyanophenyl | H | N | C | 2,6-dibromo-4-(heptafluoro-n-propylthio)phenyl |
| 1414 | 4-cyanophenyl | H | N | C | 2,6-dibromo-4-(heptafluoro-n-propylthio)phenyl |
| 1415 | 2-nitrophenyl | H | N | C | 2,6-dibromo-4-(heptafluoro-n-propylthio)phenyl |
| 1416 | 3-nitrophenyl | II | N | C | 2,6-dibromo-4-(heptafluoro-n-propylthio)phenyl |
| 1417 | 4-nitrophenyl | H | N | C | 2,6-dibromo-4-(heptafluoro-n-propylthio)phenyl |
| 1418 | 2-trifluoromethylphenyl | H | N | C | 2,6-dibromo-4-(heptafluoro-n-propylthio)phenyl |
| 1419 | 4-trifluoromethylphenyl | H | N | C | 2,6-dibromo-4-(heptafluoro-n-propylthio)phenyl |
| 1420 | 4-trifluoromethoxyphenyl | H | N | C | 2,6-dibromo-4-(heptafluoro-n-propylthio)phenyl |

TABLE 5-continued

| Compound No. | Q₁ | R₁ | A₁ | A₂ | Q₂ |
|---|---|---|---|---|---|
| 1421 | 2,3-difluorophenyl | H | N | C | 2,6-dibromo-4-(heptafluoro-n-propylthio)phenyl |
| 1422 | 2,4-difluorophenyl | H | N | C | 2,6-dibromo-4-(heptafluoro-n-propylthio)phenyl |
| 1423 | 2,5-difluorophenyl | H | N | C | 2,6-dibromo-4-(heptafluoro-n-propylthio)phenyl |
| 1424 | 2,6-difluorophenyl | H | N | C | 2,6-dibromo-4-(heptafluoro-n-propylthio)phenyl |
| 1425 | 2,4-dichlorophenyl | H | N | C | 2,6-dibromo-4-(heptafluoro-n-propylthio)phenyl |
| 1426 | 2,6-dichlorophenyl | H | N | C | 2,6-dibromo-4-(heptafluoro-n-propylthio)phenyl |
| 1427 | 3,4-dichlorophenyl | H | N | C | 2,6-dibromo-4-(heptafluoro-n-propylthio)phenyl |
| 1428 | 2-chloro-4-nitrophenyl | H | N | C | 2,6-dibromo-4-(heptafluoro-n-propylthio)phenyl |
| 1429 | 2-chloro-4-fluorophenyl | H | N | C | 2,6-dibromo-4-(heptafluoro-n-propylthio)phenyl |
| 1430 | 2-chloro-6-fluorophenyl | H | N | C | 2,6-dibromo-4-(heptafluoro-n-propylthio)phenyl |
| 1431 | 4-chloro-2-fluoropbenyl | H | N | C | 2,6-dibromo-4-(heptafluoro-n-propylthio)phenyl |
| 1432 | 4-chloro-2-nitrophenyl | H | N | C | 2,6-dibromo-4-(heptafluoro-n-propylthio)phenyl |
| 1433 | 2,3,6-trifluorophenyl | H | N | C | 2,6-dibromo-4-(heptafluoro-n-propylthio)phenyl |
| 1434 | pyridin-2-yl | H | N | C | 2,6-dibromo-4-(heptafluoro-n-propylthio)phenyl |
| 1435 | pyridin-3-yl | H | N | C | 2,6-dibromo-4-(heptafluoro-n-propylthio)phenyl |
| 1436 | 2-fluoropyridin-3-yl | H | N | C | 2,6-dibromo-4-(heptafluoro-n-propylthio)phenyl |
| 1437 | 2-chloropyridin-3-yl | H | N | C | 2,6-dibromo-4-(heptafluoro-n-propylthio)phenyl |
| 1438 | 2-chloropyridin-5-yl | H | N | C | 2,6-dibromo-4-(heptafluoro-n-propylthio)phenyl |
| 1439 | 2-methylthiopyridin-3-yl | H | N | C | 2,6-dibromo-4-(heptafluoro-n-propylthio)phenyl |
| 1440 | pyrazin-2-yl | H | N | C | 2,6-dibromo-4-(heptafluoro-n-propylthio)phenyl |
| 1441 | furan-2-yl | H | N | C | 2,6-dibromo-4-(heptafluoro-n-propylthio)phenyl |
| 1442 | thiophen-2-yl | H | N | C | 2,6-dibromo-4-(heptafluoro-n-propylthio)phenyl |
| 1443 | phenyl | Me | N | C | 2,6-dimethyl-4-heptafluoroisopropyphenyl |
| 1444 | 2-methylphenyl | Me | N | C | 2,6-dimethyl-4-heptafluoroisopropyphenyl |
| 1445 | 4-methylphenyl | Me | N | C | 2,6-dimethyl-4-heptafluoroisopropyphenyl |
| 1446 | 2-fluorophenyl | Me | N | C | 2,6-dimethyl-4-heptafluoroisopropyphenyl |
| 1447 | 3-fluorophenyl | Me | N | C | 2,6-dimethyl-4-heptafluoroisopropyphenyl |
| 1448 | 4-fluorophenyl | Me | N | C | 2,6-dimethyl-4-heptafluoroisopropyphenyl |
| 1449 | 2-chlorophenyl | Me | N | C | 2,6-dimethyl-4-heptafluoroisopropyphenyl |
| 1450 | 4-chlorophenyl | Me | N | C | 2,6-dimethyl-4-heptafluoroisopropyphenyl |
| 1451 | 2-bromophenyl | Me | N | C | 2,6-dimethyl-4-heptafluoroisopropyphenyl |
| 1452 | 2-iodophenyl | Me | N | C | 2,6-dimethyl-4-heptafluoroisopropyphenyl |
| 1453 | 3-cyanophenyl | Me | N | C | 2,6-dimethyl-4-heptafluoroisopropyphenyl |
| 1454 | 4-cyanophenyl | Me | N | C | 2,6-dimethyl-4-heptafluoroisopropyphenyl |
| 1455 | 2-nitrophenyl | Me | N | C | 2,6-dimethyl-4-heptafluoroisopropyphenyl |
| 1456 | 3-nitrophenyl | Me | N | C | 2,6-dimethyl-4-heptafluoroisopropyphenyl |
| 1457 | 4-nitrophenyl | Me | N | C | 2,6-dimethyl-4-heptafluoroisopropyphenyl |
| 1458 | 2-trifluoromethylphenyl | Me | N | C | 2,6-dimethyl-4-heptafluoroisopropyphenyl |
| 1459 | 4-trifluoromethylphenyl | Me | N | C | 2,6-dimethyl-4-heptafluoroisopropyphenyl |
| 1460 | 4-trifluoromethoxyphenyl | Me | N | C | 2,6-dimethyl-4-heptafluoroisopropyphenyl |
| 1461 | 2,3-difluorophenyl | Me | N | C | 2,6-dimethyl-4-heptafluoroisopropyphenyl |
| 1462 | 2,4-difluorophenyl | Me | N | C | 2,6-dimethyl-4-heptafluoroisopropyphenyl |
| 1463 | 2,5-difluorophenyl | Me | N | C | 2,6-dimethyl-4-heptafluoroisopropyphenyl |
| 1464 | 2,6-difluorophenyl | Me | N | C | 2,6-dimethyl-4-heptafluoroisopropyphenyl |
| 1465 | 2,4-dichlorophenyl | Me | N | C | 2,6-dimethyl-4-heptafluoroisopropyphenyl |
| 1466 | 2,6-dichlorophenyl | Me | N | C | 2,6-dimethyl-4-heptafluoroisopropyphenyl |
| 1467 | 3,4-dichlorophenyl | Me | N | C | 2,6-dimethyl-4-heptafluoroisopropyphenyl |
| 1468 | 2-chloro-4-nitrophenyl | Me | N | C | 2,6-dimethyl-4-heptafluoroisopropyphenyl |
| 1469 | 2-chloro-4-fluorophenyl | Me | N | C | 2,6-dimethyl-4-heptafluoroisopropyphenyl |
| 1470 | 2-chloro-6-fluorophenyl | Me | N | C | 2,6-dimethyl-4-heptafluoroisopropyphenyl |
| 1471 | 4-chloro-2-fluorophenyl | Me | N | C | 2,6-dimethyl-4-heptafluoroisopropyphenyl |
| 1472 | 4-chloro-2-nitrophenyl | Me | N | C | 2,6-dimethyl-4-heptafluoroisopropyphenyl |
| 1473 | 2,3,6-trifluorophenyl | Me | N | C | 2,6-dimethyl-4-heptafluoroisopropyphenyl |
| 1474 | pyridin-2-yl | Me | N | C | 2,6-dimethyl-4-heptafluoroisopropyphenyl |
| 1475 | pyridin-3-yl | Me | N | C | 2,6-dimethyl-4-heptafluoroisopropyphenyl |
| 1476 | 2-fluoropyridin-3-yl | Me | N | C | 2,6-dimethyl-4-heptafluoroisopropyphenyl |
| 1477 | 2-chloropyridin-3-yl | Me | N | C | 2,6-dimethyl-4-heptafluoroisopropyphenyl |
| 1478 | 2-chloropyridin-5-yl | Me | N | C | 2,6-dimethyl-4-heptafluoroisopropyphenyl |
| 1479 | 2-methylthiopyridin-3-yl | Me | N | C | 2,6-dimethyl-4-heptafluoroisopropyphenyl |
| 1480 | pyrazin-2-yl | Me | N | C | 2,6-dimethyl-4-heptafluoroisopropyphenyl |
| 1481 | furan-2-yl | Me | N | C | 2,6-dimethyl-4-heptafluoroisopropyphenyl |
| 1482 | thiophen-2-yl | Me | N | C | 2,6-dimethyl-4-heptafluoroisopropyphenyl |
| 1483 | phenyl | Me | N | C | 2,6-dibromo-4-(heptafluoro-n-propylthio)phenyl |
| 1484 | 2-methylphenyl | Me | N | C | 2,6-dibromo-4-(heptafluoro-n-propylthio)phenyl |
| 1485 | 4-methylphenyl | Me | N | C | 2,6-dibromo-4-(heptafluoro-n-propylthio)phenyl |
| 1486 | 2-fluorophenyl | Me | N | C | 2,6-dibromo-4-(heptafluoro-n-propylthio)phenyl |
| 1487 | 3-fluorophenyl | Me | N | C | 2,6-dibromo-4-(heptafluoro-n-propylthio)phenyl |
| 1488 | 4-fluorophenyl | Me | N | C | 2,6-dibromo-4-(heptafluoro-n-propylthio)phenyl |
| 1489 | 2-chlorophenyl | Me | N | C | 2,6-dibromo-4-(heptafluoro-n-propylthio)phenyl |
| 1490 | 4-chlorophenyl | Me | N | C | 2,6-dibromo-4-(heptafluoro-n-propylthio)phenyl |
| 1491 | 2-bromophenyl | Me | N | C | 2,6-dibromo-4-(heptafluoro-n-propylthio)phenyl |
| 1492 | 2-iodophenyl | Me | N | C | 2,6-dibromo-4-(heptafluoro-n-propylthio)phenyl |
| 1493 | 3-cyanophenyl | Me | N | C | 2,6-dibromo-4-(heptafluoro-n-propylthio)phenyl |
| 1494 | 4-cyanophenyl | Me | N | C | 2,6-dibromo-4-(heptafluoro-n-propylthio)phenyl |
| 1495 | 2-nitrophenyl | Me | N | C | 2,6-dibromo-4-(heptafluoro-n-propylthio)phenyl |

TABLE 5-continued

| Compound No. | Q$_1$ | R$_1$ | A$_1$ | A$_2$ | Q$_2$ |
|---|---|---|---|---|---|
| 1496 | 3-nitrophenyl | Me | N | C | 2,6-dibromo-4-(heptafluoro-n-propylthio)phenyl |
| 1497 | 4-nitrophenyl | Me | N | C | 2,6-dibromo-4-(heptafluoro-n-propylthio)phenyl |
| 1498 | 2-trifluoromethylphenyl | Me | N | C | 2,6-dibromo-4-(heptafluoro-n-propylthio)phenyl |
| 1499 | 4-trifluoromethylphenyl | Me | N | C | 2,6-dibromo-4-(heptafluoro-n-propylthio)phenyl |
| 1500 | 4-trifluoromethoxyphenyl | Me | N | C | 2,6-dibromo-4-(heptafluoro-n-propylthio)phenyl |
| 1501 | 2,3-difluorophenyl | Me | N | C | 2,6-dibromo-4-(heptafluoro-n-propylthio)phenyl |
| 1502 | 2,4-difluorophenyl | Me | N | C | 2,6-dibromo-4-(heptafluoro-n-propylthio)phenyl |
| 1503 | 2,5-difluorophenyl | Me | N | C | 2,6-dibromo-4-(heptafluoro-n-propylthio)phenyl |
| 1504 | 2,6-difluorophenyl | Me | N | C | 2,6-dibromo-4-(heptafluoro-n-propylthio)phenyl |
| 1505 | 2,4-dichlorophenyl | Me | N | C | 2,6-dibromo-4-(heptafluoro-n-propylthio)phenyl |
| 1506 | 2,6-dichlorophenyl | Me | N | C | 2,6-dibromo-4-(heptafluoro-n-propylthio)phenyl |
| 1507 | 3,4-dichlorophenyl | Me | N | C | 2,6-dibromo-4-(heptafluoro-n-propylthio)phenyl |
| 1508 | 2-chloro-4-nitrophenyl | Me | N | C | 2,6-dibromo-4-(heptafluoro-n-propylthio)phenyl |
| 1509 | 2-chloro-4-fluorophenyl | Me | N | C | 2,6-dibromo-4-(heptafluoro-n-propylthio)phenyl |
| 1510 | 2-chloro-6-fluorophenyl | Me | N | C | 2,6-dibromo-4-(heptafluoro-n-propylthio)phenyl |
| 1511 | 4-chloro-2-fluorophenyl | Me | N | C | 2,6-dibromo-4-(heptafluoro-n-propylthio)phenyl |
| 1512 | 4-chloro-2-nitrophenyl | Me | N | C | 2,6-dibromo-4-(heptafluoro-n-propylthio)phenyl |
| 1513 | 2,3,6-trifluorophenyl | Me | N | C | 2,6-dibromo-4-(heptafluoro-n-propylthio)phenyl |
| 1514 | pyridin-2-yl | Me | N | C | 2,6-dibromo-4-(heptafluoro-n-propylthio)phenyl |
| 1515 | pyridin-3-yl | Me | N | C | 2,6-dibromo-4-(heptafluoro-n-propylthio)phenyl |
| 1516 | 2-fluoropyridin-3-yl | Me | N | C | 2,6-dibromo-4-(heptafluoro-n-propylthio)phenyl |
| 1517 | 2-chloropyridin-3-yl | Me | N | C | 2,6-dibromo-4-(heptafluoro-n-propylthio)phenyl |
| 1518 | 2-chloropyridin-5-yl | Me | N | C | 2,6-dibromo-4-(heptafluoro-n-propylthio)phenyl |
| 1519 | 2-methylthiopyridin-3-yl | Me | N | C | 2,6-dibromo-4-(heptafluoro-n-propylthio)phenyl |
| 1520 | pyrazin-2-yl | Me | N | C | 2,6-dibromo-4-(heptafluoro-n-propylthio)phenyl |
| 1521 | furan-2-yl | Me | N | C | 2,6-dibromo-4-(heptafluoro-n-propylthio)phenyl |
| 1522 | thiophen-2-yl | Me | N | C | 2,6-dibromo-4-(heptafluoro-n-propylthio)phenyl |
| 1523 | phenyl | H | C | N | 2,6-dimethyl-4-heptafluoroisopropylphenyl |
| 1524 | phenyl | H | C | N-oxide | 2,6-dimethyl-4-heptafluoroisopropylphenyl |
| 1525 | phenyl | H | N-oxide | C | 2,6-dimethyl-4-heptafluoroisopropylphenyl |
| 1526 | 2-fluorophenyl | H | N-oxide | C | 2,6-dimethyl-4-heptafluoroisopropylphenyl |
| 1527 | phenyl | H | N-oxide | C | 2,6-dibromo-4-(heptafluoro-n-propylthio)phenyl |
| 1528 | 2-fluorophenyl | H | N-oxide | C | 2,6-dibromo-4-(heptafluoro-n-propylthio)phenyl |
| 1529 | phenyl | Me | N-oxide | C | 2,6-dimethyl-4-heptafluoroisopropylphenyl |
| 1530 | 2-fluorophenyl | Me | N-oxide | C | 2,6-dimethyl-4-heptafluoroisopropylphenyl |
| 1531 | phenyl | Me | N-oxide | C | 2,6-dibromo-4-(heptafluoro-n-propylthio)phenyl |
| 1532 | 2-fluorophenyl | Me | N-oxide | C | 2,6-dibromo-4-(heptafluoro-n-propylthio)phenyl |

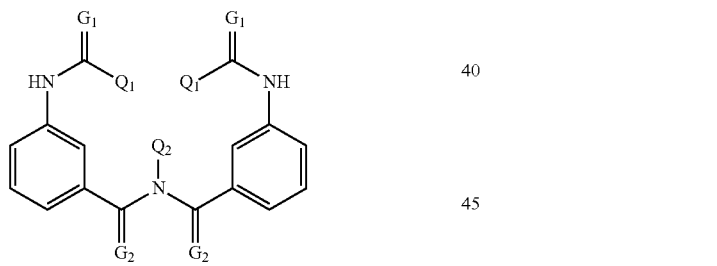

TABLE 6

| Compound No. | Q$_1$ | G$_1$ | G$_1$ | Q$_2$ |
|---|---|---|---|---|
| 1533 | phenyl | O | S | 2,6-dimethyl-4-heptafluoroisopropyphenyl |
| 1534 | phenyl | S | O | 2,6-dimethyl-4-heptafluoroisopropyphenyl |
| 1535 | phenyl | S | S | 2,6-dimethyl-4-heptafluoroisopropyphenyl |
| 1536 | phenyl | O | S | 2,6-dibromo-4-(heptafluoro-n-propylthio)phenyl |
| 1537 | phenyl | S | O | 2,6-dibromo-4-(heptafluoro-n-propylthio)phenyl |
| 1538 | phenyl | S | S | 2,6-dibromo-4-(heptafluoro-n-propylthio)phenyl |
| 1539 | phenyl | O | S | 2,6-dimethyl-4-(nonafluoro-2-butyl)phenyl |
| 1540 | phenyl | S | O | 2,6-dimethyl-4-(nonafluoro-2-butyl)phenyl |
| 1541 | phenyl | S | S | 2,6-dimethyl-4-(nonafluoro-2-butyl)phenyl |
| 1542 | phenyl | O | S | 2-bromo-4-(heptafluoroisopropyl)-6-(methylsulfonyl)phenyl |
| 1543 | phenyl | S | O | 2-bromo-4-(heptafluoroisopropyl)-6-(methylsulfonyl)phenyl |
| 1544 | phenyl | S | S | 2-bromo-4-(heptafluoroisopropyl)-6-(methylsulfonyl)phenyl |

TABLE 6-continued

| Compound No. | $Q_1$ | $G_1$ | $G_1$ | $Q_2$ |
|---|---|---|---|---|
| 1545 | phenyl | O | S | 2-n-propyl-6-iodo-4-(heptafluoroisopropyl)phenyl |
| 1546 | phenyl | S | O | 2-n-propyl-6-iodo-4-(heptafluoroisopropyl)phenyl |
| 1547 | phenyl | S | S | 2-n-propyl-6-iodo-4-(heptafluoroisopropyl)phenyl |
| 1548 | phenyl | O | S | 2,6-dibromo-4-(heptafluoro-n-propylsulfinyl)phenyl |
| 1549 | phenyl | S | O | 2,6-dibromo-4-(heptafluoro-n-propylsulfinyl)phenyl |
| 1550 | phenyl | S | S | 2,6-dibromo-4-(heptafluoro-n-propylsulfinyl)phenyl |
| 1551 | phenyl | O | S | 2,6-dichloro-4-(heptafluoro-n-propylthio)phenyl |
| 1552 | phenyl | S | O | 2,6-dichloro-4-(heptafluoro-n-propylthio)phenyl |
| 1553 | phenyl | S | S | 2,6-dichloro-4-(heptafluoro-n-propylthio)phenyl |

The insecticide including as an active ingredient the imide compound represented by Formula (1) according to the invention is suitable for controlling pests such as various agricultural pests, horticultural pests, or stored grain pests damaging useful crops including paddy-field rice, fruit trees, vegetables, other crops, or ornamental flowers; insanitary pests; or nematodes.

The insecticide exhibits a strong insecticidal effect against pests such as lepidopteran pests such as *Diaphania indica, Homona magnanima, Hellula undalis, Adoxophyes orana faciata, Adoxophyes* sp., *Archips fuscocupreanus, Carposina niponensis, Grapholita inopinata, Grapholita molesta, Leguminivora glycinivorella, Olethreutes mori, Phyllocnistis citrella, Stathmopoda masinissa, Caloptilia theivora, Caloptilia zachrysa, Phyllonotycter ringoniella, Spulerrina astaurota, Papilio xuthus, Pieris rapae crucivora, Helicoverpa armigera, Lapsey resia pomonella, Plutella xylostella, Argyresthia conjugella, Carposina niponensis, Chilo suppressalis, Cnaphalocrocis medinalis, Ephestia elutella, Glyphodes pyloalis, Scirpophaga incertulas, Parnara guttata, Pseudaletiaseparata, Sesamia inferens, Mamestra brassicae, Spodoptera litura, Spodoptera exigua, Agrotis ipsilon, Agrotis segetum, Autographa nigrisigna,* or *Trichoplusia ni*; Hemipteran pests such as *Macrosteles fascifrons, Nephotettix cincticeps, Nilaparvata lugens, Laodelphax striatellus, Sogatella furcifera, Diaphorina citri, Aleurolobus taonabae, Bermisia argentifolii, Bemisia tabaci, Trialeurodes vaporariorum, Lipaphis erysimi, Aphis gossypii, Aphis Citricola, Myzus persicae, Ceroplastes ceriferus, Pseudococcus Comstocki, Planococcus kraunhiae, Pulvinaria aurantii, Pseudaonidia duplex, Comstockaspis perniciosa, Unaspis yanonensis, Plautia stali,* or *Halyomorpha mista*; Coleopteran pests such as *Anomala rufocuprea, Popillia japonica, Lasioderma serricorne, Lyctus brunneus, Epilachna vigintioctopunctata, Callosobruchus chinensis, Listroderes costirostris, Sitophilus zeamais, Anthonomusgradis gradis, Lissorhoptrus oryzophilus, Aulacophora femoralis, Oulema oryzae, Phyllotreta striolata, Tomicus piniperda, Leptinotarsa decemlineata, Epilachna varivestis, Diabrotica* sp., *Psacothea hilaris,* or *Anoplophora malasiaca*; Dipteran pests such as *Dacus (Bactrocera) dorsalis, Agromyza oryzae, Delia antiqua, Delia platura, Asphondylia* sp., *Musca domestica, Chromatomyia horticola, Liriomyza trifolii, Liriomyza bryoniae,* or *Culex pipienspipiens*; Tylenchidan pests such as *Pratylenchus coffeae, Pratylenchus* sp., *Globodera rostochiensis, Meloidogyne* sp., *Tylemchulus semipenetrans, Aphelenchus avenae,* or *Aphelenchoides ritzemabosi*; Thysanopteran pests such as *Thrips palmi, Frankliniella occidentalis, Scirtothrips dorsalis, Thrips flavus,* or *Thrips tabaci*; or Orthoptcran pests such as *Blattella germanica, Periplaneta americana,* or *Oxya yezoensis*.

The insecticide including as an active ingredient the imide compound represented by Formula (1) according to the invention exhibits a significant insecticidal effect against the above-described pests that damages useful crops such as wet-field crops, dry-field crops, fruit trees, vegetables, and other crops and ornamental flowers, and therefore, the effect as an insecticide according to the invention can be obtained by treating the paddy field water, plant stems and leaves, or soil of the crops of 1 wet-field, dry-field, fruit trees, vegetables, other crops, ornamental flowers, or the like during the seasons in which the appearance of such pests is expected, or before or at the point when the pest appearance is observed.

The insecticide according to the invention is generally used as a preparation convenient for application, which is prepared according to the conventional method for agricultural/horticultural preparations. That is, the imide compound represented by Formula (1) can be put to use as a preparation in any form such as a suspension concentrate, an emulsifiable concentrate, a water-soluble powder, a wettable powder, a granular formulation, a powder formulation, or a tablet, by mixing with a suitable inert carrier, and if needed further adding an adjuvant, through the step of dissolution, separation, suspension, mixing, impregnation, adsorption and/or adhesion.

The inactive carrier that can be used in the invention may be a solid or liquid carrier. Examples of materials that can be used as the solid carrier include soybean powder, grain powder, wood flour, bark powder, sawdust, tobacco stalk powder, walnut shell flour, wheat bran, cellulose powder, extraction residue of plants, synthetic polymers such as pulverized synthetic resins, clays (such as kaolin, bentonite, or acid clay), talcs (such as talc or pyrophyllite), silicas (such as diatomite, silica sand, mica, or white carbon, i.e., synthetic high-dispersion silicic acid which is also referred to as fine hydrous silica powder or hydrous silicic acid, of which some commercial products contain calcium silicate as a major component), active carbon, sulfur powder, pumice, calcined diatomite, pulverized brick, fly ash, sand, calcium carbonate, powders of inorganic minerals such as calcium phosphate, chemical fertilizers such as ammonium sulfate, ammonium phosphate, ammonium nitrate, urea, or ammonium chloride, and manure. These materials may be used singly, or as a mixture of two or more kinds thereof.

The material that can be used as the liquid inert carrier is selected from materials which can serve as a solvent themselves and materials which cannot serve as a solvent themselves but can disperse active ingredient compounds with the help of an adjuvant. Typical examples of the liquid carrier include water, alcohols (such as methanol, ethanol, isopropanol, butanol, or ethylene glycol), ketones (such as acetone, methyl ethyl ketone, methyl isobutyl ketone, diisobutyl ketone, or cyclohexanone), ethers (such as diethyl ether, dioxane, cellosolve, diisopropyl ether, or tetrahydrofuran), aliphatic hydrocarbons (such as kerosene or mineral oil), aromatic hydrocarbons (such as benzene, toluene, xylene, solvent naphtha, or alkyl naphthalene), halogenated hydrocarbons (such as dichloromethane, chloroform, carbon tetrachloride, or chlorinated benzene), esters (such as ethyl acetate, butyl acetate, ethyl propionate, diisobutyl phthalate, dibutyl phthalate, or dioctyl phthalate), amides (such as dimethylformamide, diethylformamide, or dimethylacetamide), and nitrites (such as acetonitrile). These materials may be used singly, or as a mixture of two or more kinds thereof.

Examples of the adjuvant include typical adjuvants listed below. These adjuvants may be used depending on the purpose. The adjuvants may be used singly, or in combination of two or more kinds thereof. In some cases, it is possible that no adjuvants are used.

A surfactant is used for emulsification, dispersion, solubilization and/or wetting of an active ingredient compound. Examples thereof include a polyoxyethylene alkyl ether, a polyoxyethylene alkyl aryl ether, a polyoxyethylene higher fatty acid ester, a polyoxyethylene resin acid ester, a polyoxyethylene sorbitan monolaurate, a polyoxyethylene sorbitan monooleate, an alkylaryl sulfonate, a naphthalene sulfonate, a lignosulfonate, and a higher alcohol sulfate.

The adjuvant such as casein, gelatin, starch, methyl cellulose, carboxymethyl cellulose, gum arabic, polyvinyl alcohol, wood turpentine oil, rice-bran oil, bentonite, xanthan gum, or a lignosulfonate may be used for dispersion-stabilization of an active ingredient compound and for adhesion and/or binding.

The adjuvant such as a wax, a stearate, or an alkyl phosphate may be used for improving the flowability of solid products. The adjuvant such as a naphthalene sulfonate condensate or a condensed phosphate may be used as a deflocculant for suspension products. The adjuvant such as silicone oil may be used as defoamant.

The imide compound represented by Formula (1) according to the invention is stable against light, heat, and oxidation. If needed, an appropriate amount of antioxidant or ultraviolet absorber, for example, a phenol derivative such as BHT (2,6-di-t-butyl-4-methylphenol) or BHA (butylhydroxyanisole); a bisphenol derivative; an arylamine such as phenyl-β-naphtylamine, phenetidine or a condensate of acetone and phenyl-α-naphtylamine; or a benzophenone compound, is added as a stabilizer to obtain a compound exhibiting more stable effects.

The amount of the active ingredient of the imide compound represented by Formula (1) according to the invention is usually from 0.5% by weight to 20% by weight for powders, from 5% by weight to 50% by weight for emulsifiable concentrates, from 10% by weight to 90% by weight for wettable powders, from 0.1% by weight to 20% by weight for granules, or from 10% by weight to 90% by weight for flowable preparation. The amount of the carrier in each form is usually from 60% by weight to 99% by weight for powders, from 40% by weight to 95% by weight for emulsifiable concentrates, from 10% by weight to 90% by weight for wettable powders, from 80% by weight to 99% by weight for granules, or from 10% by weight to 90% by weight for flowable preparations. The amount of the adjuvant is usually from 0.1% by weight to 20% by weight for powders, from 1% by weight to 20% by weight for emulsifiable concentrates, from 0.1% by weight to 20% by weight for wettable powders, from 0.1% by weight to 20% by weight for granules, or from 0.1% by weight to 20% by weight for flowable preparations.

In order to control various pests, the compound may be applied to the crops on which appearance of the pest is expected or to places where such occurrence is not preferable as it is or as an adequate dilution with water or the like, or as a suspension, in an amount effective for disease protection.

The amount of use depends on various factors such as the purpose, the pest to be controlled, the state of plant growth, trends in pest appearance, climate, environmental conditions, formulation, method of use, place of use, and timing of use, and it is preferable to use such that the concentration of the active ingredient is from 0.0001 ppm to 5000 ppm, and preferably from 0.01 ppm to 1000 ppm. The dose per 10 a is generally from 1 g to 300 g of the active ingredient.

The insecticide that includes as an active ingredient the imide compound represented by Formula (1) according to the invention may be used singly for controlling pests various agricultural pests, horticultural pests, or stored grain pests damaging paddy-field rice, fruit trees, vegetables, other crops, or ornamental flowers; insanitary pests; or nematodes. In order to obtain more significant control effect of controlling a wide variety of diseases and pests that appear simultaneously, the imide compound represented by Formula (1) also may be used in combination with at least one selected from insecticides and fungicides other than the imide compound.

Examples of other insecticides that can be used in combination with the imide compound represented by Formula (1) include synthetic pyrethroid insecticides such as allethrin, tetramethrin, resmethrin, phenothrin, flumethrin, permethrin, cypermethrin, deltamethrin, cyhalothrin, cyfluthrin, fenpropathrin, tralomethrin, cycloprothrin, flucythrinate, fluvalinate, acrinathrin, tefluthrin, bifenthrin, empenthrin, beta-cyfluthrin, beta-cypermethrin, or fenvalerate, and carious isomers thereof; organophosphorus insecticides such as a pyrethrum extract, DDVP, cyanophos, fenthion, fenitrothion, tetrachlorvinphos, dimethylvinphos, propaphos, methylparathion, temephos, phoxim, acephate, isofenphos, salithion, DEP, EPN, ethion, mecarbam, pyridaphenthion, diazinon, pirimiphos-methyl, etrimfos, isoxathion, quinalphos, chlorpyrifos-methyl, chlorpyrifos, phosalone, phosmet, methidathion, oxydeprofos, vamidothion, malathion, phenthoate, dimethoate, formothion, thiometon, ethyl thiometon, phorate, terbufos, profenofos, prothiofos, sulprofos, pyraclofos, monocrotophos, naled, fosthiazate, or cadusafos; carbamate insecticides such as NAG, MTMC, HIPC, BPMC, XMC, PFIC, MPMC, ethiofencarb, bendiocarb, pirimicarb, carbosulfan, benfuracarb, methomyl, oxamyl, or aldicarb; aryl propyl ether insecticides such as ethofenprox or halfenprox; silyl ethers such as silafluofen; pest-control natural products such as nicotine sulfate, polynactin, abamectin, milbemectin, or BT; insecticides such as cartap, thiocyclam, bensultap, diflubenzuron, chlorfluazuron, teflubenzuron, triflumuron, flufenoxuron, flucycloxuron, hexaflumuron, fluazuron, imidacloprid, nitenpyram, acetamiprid, dinotefuran, pymetrozine, fipronil, buprofezin, fenoxycarb, pyriproxyfen, methoprene, hydroprene, kinoprene, endosulfan, diafenthiuron, triazuron, tebufenozide, or benzoepin; miticides such as dicofol, chlorobenzilate, phenisobromolate, tetradifon, CPCBS, BPPS, quinomethionate, amitraz, benzomate, hexythiazox, fenbutatin oxide, cyhexatin, dienochlor, clofentezine, pyridaben, fenpyroximate, fenazaquin, or tebufenpyrad; and novaluron, noviflumuron, emamectin benzoate, clothianidin, thiacloprid, thiamethoxam, flupyrazofos, acequinocyl, bifenazate, chromafenozide, etoxazole, fluacrypyrim, flufenzine, halofenozide, indoxacarb, methoxyfenozide, spirodiclofen, tolfenpyrad, gamma-cyhalothrin, ethiprole, amidoflumet, bistrifluron, flonicamid, flubrocythrinate, flufenerim, pyridalyl, pyrimidifen, spinosad, and spiromesifen.

Examples of the fungicide that can be used in combination with imide compound represented by Formula (1) include azole fungicides such as triadimefon, hexaconazole, propiconazole, ipconazole, prochloraz, or triflumizole; pyrimidine fungicides such as pyrifenox or fenarimol; anilinopyrimidine fungicides such as mepanipyrim or cyprodinil; acylalanine fungicides such as metalaxyl, oxadixyl, or benalaxyl; benzoimidazole fungicides such as thiophanate-methyl or benomyl; dithiocarbamate fungicides such as manzeb, propineb, zineb, or metiram; organic chlorinated fungicides such as tetrachloroisophthalonitrile; carboxamide fungicides such as carpropamid or ethaboxam; morpholin fungicides such as dimethomorph; strobilurin fungicides such as azoxystrobin, kresoxim-methyl, metominostrobin, orysastrobin, fluoxastrobin, trifloxystrobin, dimoxystrobin, pyraclostrobin, or picoxystrobin; dicarboximide fungicides such as iprodione or procymidone; soil fungicides such as flusulfamide, dazomet, methyl isothiocyanate, or chloropicrin; copper fungicides such as basic copper chloride, basic copper sulfate, copper nonylphenol sulfonate, copper-oxinate, or DBEDC; inorganic fungicides such as sulfur or zinc sulfate; organic phosphorus fungicides such as edifenphos, tolciofos-methyl, or fosetyl; melanin biosynthesis inhibiting fungicides such as fthalide, tricyclazole, pyroquilone, or diclocymet; antibiotic fungicides such as kasugamycin, validamycin, or polyoxin; natural-product fungicides such as rapeseed oil; and fungicides such as benthiavalicarb-isopropyl, iprovalicarb, cyflufenamid, fenhexamid, quinoxyfen, spiroxamine, diflumetorim, metrafenone, picobenzamid, proquinazid, silthiofam, oxpoconazole, famoxadone, cyazofamid, fenamidone, furametpyr, zoxamide, boscalid, tiadinil, simeconazol, chlorothalonil, cymoxanil, captan, dithianon, fluazinam, folpet, dichlofluanid, (RS)—N-[2-(1,3-dimethylbutyl)thiophen-3-yl]-1-methyl-3-trifluoromethyl-1H-pyrazole-4-carboxamide (generic name: penthiopyrad, pending), oxycarboxin, mepronil, flutolanil, triforine, oxolinic acid, probenazole, acibenzolar-S-methyl, isoprothiolane, ferimzone, diclomezine, pencycuron, fluoroimide, chinomethionat, iminoctadine-triacetate, or iminoctadine-albesilate.

In a case in which the imide compound represented by Formula (1) is used in combination with at least one selected from other insecticides and fungicides, the imide compound represented by Formula (1) may be used as a mixed composition together with at least one selected from other insecticides and fungicides; or the imide compound represented by Formula (1) and at least one selected from other insecticides and fungicides may be mixed when the insecticide is applied.

Other than the other insecticides and fungicides described above, imide compound represented by Formula (1) may be mixed with a plant protecting agent and/or a material, such as a herbicide, a fertilizer, an amendment, or a plant growth regulators, whereby a multipurpose composition with a significant effect can be obtained and a composition with an additive effect or a synergetic effect can be expected.

EXAMPLES

Representative Examples of the invention are described with reference to the following Examples, but the invention is not limited thereto. The $^1$H-NMR chemical shift values are shown in ppm downfield from tetramethylsilane reference. In addition, "s" means singlet, "d" means doublet, "t" means triplet, "m" means multiplet, and "brs" means broad singlet. Unless otherwise specified, "%" and "part(s)" are based on mass.

Example 1-1

Synthesis of N-[2-fluoro-3-[benzoyl(methyl)amino]benzoyl]-3-[benzoyl(methyl)amino]-N-[2-bromo-4-heptafluoroisopropyl-6-(trifluoromethyl)phenyl]-2-fluorobenzamide (Compound No. 1342)

1.00 g of 2-bromo-4-heptafluoroisopropyl-6-(trifluoromethyl)aniline, 0.89 g of triethylamine, 0.03 g of N,N-dimethyl-4-aminopyridine, and 1.57 g of 2-fluoro-3-(N-methylbenzamide)benzoyl chloride were added to 4.00 g of 1,3-dimethylimidazolidin-2-one, and the mixture was stirred for 1 hour at room temperature. The resultant was extracted with ethyl acetate and washed with saturated saline, and then the organic layer was dried over anhydrous magnesium sulfate. The magnesium sulfate was filtered off, and the filtrate was concentrated. The resultant was purified on silica gel column chromatography to obtain 2.20 g of the desired imide compound (yield: 97%) as a white solid.

$^1$H-NMR (DMSO-d$_6$, 70° C.) δppm: 8.44 (s, 1H), 7.99 (s, 1H) 7.60-7.57 (m, 2H), 7.51 (brs, 2H), 7.30-7.18 (m, 12H), 3.12 (s, 6H)

MS (M+H)$^+$=918, 920

Example 1-2

Synthesis of N-[2-fluoro-3-[benzoyl(methyl)amino]benzoyl]-3-[benzoyl(methyl)amino]-N-[2-bromo-4-heptafluoroisopropyl-6-(trifluoromethyl)phenyl]-2-fluorobenzamide (Compound No. 1342)

1.00 g of 2-bromo-4-heptafluoroisopropyl-6-(trifluoromethyl)aniline, 0.89 g of triethylamine, 0.03 g of N,N-dimethyl-4-aminopyridine, 1.57 g of 2-fluoro-3-(N-methylbenzamide)benzoyl chloride, and 3.00 g of toluene were mixed, and the mixture was stirred for 4 hours at 90° C. The resultant was extracted with ethyl acetate and washed with saturated saline, and then the organic layer was dried over anhydrous magnesium sulfate. The magnesium sulfate was filtered off, and the filtrate was concentrated. The resultant was purified on silica gel column chromatography to obtain 2.16 g of the desired imide compound (yield: 95%) as a white solid.

Example 2

Synthesis of N-[2-fluoro-3-[benzoyl(methyl)amino]benzoyl]-3-[benzoyl(methyl)amino]-N-[4-heptafluoroisopropyl-2-iodo-6-(trifluoromethyl)phenyl]-2-fluorobenzamide (Compound No. 1343)

3.79 g of 4-heptafluoroisopropyl-2-iodo-6-(trifluoromethyl)aniline, 2.80 g of triethylamine, 0.06 g of N,N-dimethyl-4-aminopyridine, 5.3 g of 2-fluoro-3-(N-methylbenzamide)benzoyl chloride, and 7.6 g of toluene were mixed, and the mixture was stirred for 2 hours at 90° C. The reaction solution was cooled to room temperature. Then the resultant was mixed with water and the precipitated crystal was filtered, washed with toluene and washed with water to obtain 5.87 g of the desired imide compound (yield 73%) as a pale yellow solid.

$^1$H-NMR (DMSO-d$_6$, 70° C.) δppm: 8.53 (s, 1H), 7.97 (s, 1H), 7.54-7.51 (m, 4H), 7.30-7.13 (m, 12H), 3.14 (s, 6H)

MS (M+H)$^+$=966

Example 3

Synthesis of N-[2-fluoro-3-[4-fluorobenzoyl(methyl)amino]benzoyl]-3-[4-fluorobenzoyl(methyl)amino]-N-[2-bromo-4-heptafluoroisopropyl-6-(trifluoromethyl)phenyl]-2-fluorobenzamide (Compound No. 1344)

The title compound was synthesized in a manner similar to the above.

$^1$H-NMR (DMSO-d$_6$, 70° C.) δppm: 8.44 (s, 1H), 7.97 (s, 1H), 7.64-7.62 (m, 2H), 7.50 (brs, 2H), 7.28-7.24 (m, 6H), 7.00-6.96 (m, 4H), 3.15 (s, 6H)
MS (M+H)$^+$=954, 956

Example 4

Synthesis of N-[2-fluoro-3-[4-fluorobenzoyl(methyl) amino]benzoyl]-3-[4-fluorobenzoyl(methyl)amino]-N-[4-heptafluoroisopropyl-2-iodo-6-(trifluoromethyl)phenyl]-2-fluorobenzamide (Compound No. 1345)

The title compound was synthesized in a manner similar to the above.
$^1$H-NMR (DMSO-d$_6$, 70° C.) δppm: 8.53 (s, 1H), 7.95 (s, 1H), 7.59-7.57 (m, 2H), 7.48 (brs, 2H), 7.28-7.22 (m, 6H), 7.01-6.97 (m, 4H), 3.16 (s, 6H)
MS (M+H)$^+$=1002

Example 5

Synthesis of N-[2-fluoro-3-[2,6-difluorobenzoyl(methyl)amino]benzoyl]-3-[2,6-difluorobenzoyl(methyl)amino]-N-[2-bromo-4-heptafluoroisopropyl-6-(trifluoromethyl)phenyl]-2-fluorobenzamide (Compound No. 1346)

The title compound was synthesized in a manner similar to the above.
$^1$H-NMR (DMSO-d$_6$, 70° C.) δppm: 8.46 (s, 1H), 8.01 (s, 1H), 7.33-7.30 (m, 4H), 7.25-7.11 (m, 5H), 6.86 (brs, 3H), 3.17 (s, 6H)
MS (M+H)$^+$=990, 992

Example 6

Synthesis of N-[2-fluoro-3-[4-nitrobenzoyl(methyl) amino]benzoyl]-3-[4-nitrobenzoyl(methyl)amino]-N-[2-bromo-4-heptafluoroisopropyl-6-(trifluoromethyl)phenyl]-2-fluorobenzamide (Compound No. 1357)

The title compound was synthesized in a manner similar to the above.
$^1$H-NMR (DMSO-d$_6$, 70° C.) δppm: 8.41 (s, 1H), 8.03-8.01 (m, 4H), 7.92 (s, 1H), 7.72-7.70 (m, 6H), 7.30-7.24 (m, 2H), 3.20 (s, 6H)
MS (M+Na)$^+$=1030, 1032

Example 7

Synthesis of N-[2-fluoro-3-[4-nitrobenzoyl(methyl) amino]benzoyl]-3-[4-nitrobenzoyl(methyl)amino]-N-[4-heptafluoroisopropyl-2-iodo-6-(trifluoromethyl)phenyl]-2-fluorobenzamide (Compound No. 1358)

The title compound was synthesized in a manner similar to the above.
$^1$H-NMR (DMSO-d$_6$, 70° C.) δppm: 8.49 (s, 1H), 8.03-8.02 (m, 4H), 7.92 (s, 1H), 7.70-7.67 (m, 2H), 7.49-7.48 (m, 4H), 7.25-7.24 (m, 2H), 3.21 (s, 6H)
MS (M+Na)$^+$=1078

Example 8

Synthesis of N-[2-fluoro-3-[benzoyl(methyl)amino] benzoyl]-3-[benzoyl(methyl)amino]-N-[2,4-bis(heptafluoroisopropyl)-6-(trifluoromethyl)phenyl]-2-fluorobenzamide (Compound No. 1359)

The title compound was synthesized in a manner similar to the above.
$^1$H-NMR (DMSO-d$_6$, 70° C.) δppm: 8.48 (s, 1H), 8.07 (s, 1H), 7.57-7.54 (m, 2H), 7.34 (brs, 2H), 7.28-7.18 (m, 14H), 3.07 (s, 6H)
MS (M+H)$^+$=1008

Example 9

Synthesis of N-[2-fluoro-3-[benzoyl(methyl)amino] benzoyl]-3-[benzoyl(methyl)amino]-N-[4-bromo-2-heptafluoroisopropyl)-6-(trifluoromethyl)phenyl]-2-fluorobenzamide (Compound No. 1360)

The title compound was synthesized in a manner similar to the above.
$^1$H-NMR (DMSO-d$_6$, 70° C.) δppm: 8.52 (s, 1H), 8.09 (s, 7.51-7.48 (m, 2H), 7.28-7.26 (m, 2H), 7.21-7.19 (m, 12H), 3.08 (s, 6H)
MS (M+H)$^+$=918, 920

Example 10

Synthesis of N-[2-fluoro-3-[benzoyl(methyl)amino] benzoyl]-3-[benzoyl(methyl)amino]-N-[2,6-dibromo-4-(nonafluoro-2-butyl)phenyl]-2-fluorobenzamide (Compound No. 1361)

The title compound was synthesized in a manner similar to the above.
$^1$H-NMR (DMSO-d$_6$, 70° C.) δppm: 7.95 (s, 2H), 7.61-7.58 (m, 2H), 7.50 (brs, 2H), 7.29-7.26 (m, 2H), 7.22-7.16 (m, 10H), 3.21 (s, 6H)
MS (M+Na)$^+$=1000, 1002

Hereinbelow, examples of preparations containing as an active ingredient the compound represented by Formula (1) according to the invention are shown, but the invention is not limited thereto. In the preparation examples, "part(s)" means "part(s) by mass".

Preparation Example 1

20 parts of the compound represented by Formula (1) according to the invention, 10 parts of SOLPOLE 355S (surfactant manufactured by TOHO Chemical Industry Co., Ltd.), and 70 parts of xylene were stirred and mixed uniformly, thereby obtaining an emulsifiable concentrate.

Preparation Example 2

10 parts of the compound represented by Formula (1) according to the invention, parts of sodium alkylnaphthalene sulfonate, 1 part of sodium lignin sulfonate, 5 parts of white carbon, and 82 parts of diatomite were stirred and mixed uniformly, thereby obtaining a wettable powder.

Preparation Example 3

0.3 parts of the compound represented by Formula (1) according to the invention and 0.3 parts of white carbon were mixed uniformly, and 99.2 parts of clay and 0.2 parts of DRILESS A (manufactured by Sankyo Agro Co., Ltd.) were added thereto, followed by pulverizing and mixing uniformly, thereby obtaining a powder formulation.

Preparation Example 4

2 parts of the compound represented by Formula (1) according to the invention, 2 parts of white carbon, 2 parts of sodium lignin sulfonate, and 94 parts of bentonite were pulverized and mixed uniformly, and water was added thereto, followed by kneading, granulating, and drying, thereby obtaining a granular formulation.

Preparation Example 5

20 parts of the compound represented by Formula (1) according to the invention and 5 parts of a 20% aqueous solution of polyvinyl alcohol were sufficiently stirred and mixed, and then 75 parts of an 0.8% aqueous solution of xanthan gum was added thereto, followed by stirring and mixing again, thereby obtaining a flowable formulation.

Hereinbelow, in order to demonstrate the significant pest controlling effect of the imide compound represented by Formula (1) according to the invention, the following Test Examples are shown, but the invention is not limited thereto.

Test Example 1

Insecticidal Test against *Spodoptera litura*

A piece of a cabbage leaf was immersed for 30 seconds in a chemical solution in which a test compound had been prepared at a predetermined concentration, and air-dried, and then put into a 7 cm polyethylene cup. To the cup, 2-stage larvae of *Spodoptera litura* were released. They were left to stand in a thermostatic chamber at 25° C., and the numbers of the living pests and the dead pests were examined after 3 days. The test was carried out with five larvae per group in two replicates.

As a result, the compounds of Compound Nos. 1342, 1343, 1344, 1345, 1357, 1358, and 1361 showed a insecticidal death rate of 70% or more at a concentration of 100 ppm.

Test Example 2

Insecticidal Test against *Plutella xylostella*

A piece of a cabbage leaf was immersed for 30 seconds in a chemical solution in which a test compound had been prepared at a predetermined concentration, and air-dried, and then put into a 7 cm polyethylene cup. To the cup, 2-stage larvae of *Plutella xylostella* were released. They were left to stand in a thermostatic chamber at 25° C., and the numbers of the living pests and the dead pests were examined after 3 days. The test was carried out with five larvae per group in two replicates.

As a result, the compounds of Compound Nos. 1342, 1343, 1344, 1357, 1358, and 1361 showed a insecticidal death rate of 70% or more at a concentration of 100 ppm.

All publications, patent applications, and technical standards mentioned in this specification are herein incorporated by reference to the same extent as if each individual publication, patent application, or technical standard was specifically and individually indicated to be incorporated by reference.

The invention claimed is:

1. An imide compound represented by the following Formula (1):

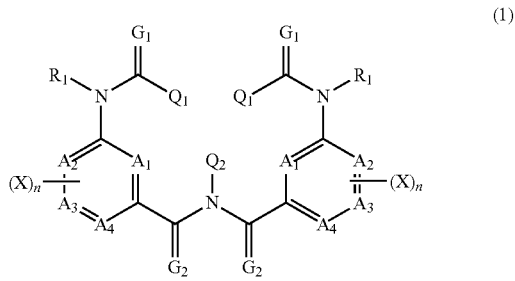

wherein, in Formula (1), each of $A_1$, $A_2$, $A_3$, and $A_4$ independently represents a carbon atom, a nitrogen atom, or an oxidized nitrogen atom; each $R_1$ independently represents a hydrogen atom, a C1-C4 alkyl group which may be substituted, or a C2-C4 alkylcarbonyl group which may be substituted; each of $G_1$ and $G_2$ independently represents an oxygen atom or a sulfur atom; each X independently represents a hydrogen atom, a halogen atom, a C1-C3 alkyl group, or a trifluoromethyl group; when there are two or more X's, each X may be the same as or different from one another; and n represents an integer from 0 to 4; and wherein each $Q_1$ independently represents a phenyl group which may be substituted, a naphthyl group which may be substituted, or a heterocyclic group which may be substituted; and $Q_2$ represents a phenyl group or a heterocyclic group, each of which has one or more substituents, wherein at least one of the one or more substituents represents a C1-C4 haloalkoxy group, a C2-C6 perfluoroalkyl group, a C1-C6 perfluoroalkylthio group, a C1-C6 perfluoroalkylsulfinyl group, or a C1-C6 perfluoroalkylsulfonyl group.

2. The imide compound according to claim 1, wherein, in Formula (1), each $R_1$ independently represents a hydrogen atom or a C1-C4 alkyl group;

each X independently represents a hydrogen atom, a halogen atom, or a trifluoromethyl group;

each $Q_1$ independently represents:
a phenyl group that may have one or more substituents, which may be the same as or different from one another, selected from the substituent group consisting of a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a mono-(C1-C4) alkylamino group, a di-(C1-C4) alkylamino group, a cyano group, a nitro group, a hydroxy group, a formyl group, a C2-C4 alkylcarbonyl group, a C2-C4 alkylcarbonyloxy group, a C2-C4 alkoxycarbonyl group, an acetylamino group and a phenyl group; or
a heterocyclic group selected from the group consisting of a pyridyl group, a pyridine-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrole group, a pyrazolyl group and a tetrazolyl group, wherein the heterocyclic group may have one or more substituents, which may be the same as or different from one another, selected from the substituent group consisting of a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a mono-(C1-C4) alkylamino group, a di-(C1-C4) alkylamino group, a cyano group, a nitro group, a hydroxy group, a formyl group, a C2-C4 alkylcarbonyl group, a C2-C4 alkylcarbonyloxy group, a C2-C4 alkoxycarbonyl group, an acetylamino group and a phenyl group; and $Q_2$ represents:

a phenyl group having a substituent represented by the following Formula (2):

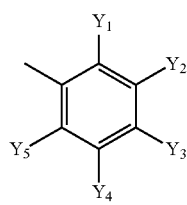

(2)

wherein, in Formula (2), each of $Y_1$ and $Y_5$ independently represents a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, or a cyano group; $Y_3$ represents a C2-C6 perfluoroalkyl group, a C1-C6 perfluoroalkylthio group, a C1-C6 perfluoroalkylsulfinyl group, or a C1-C6 perfluoroalkylsulfonyl group; and each of $Y_2$ and $Y_4$ independently represents a hydrogen atom, a halogen atom, or a C1-C4 alkyl group; or a pyridyl group having a substituent represented by the following Formula (3):

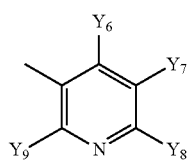

(3)

wherein, in Formula (3), each of $Y_6$ and $Y_9$ independently represents a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, or a cyano group; $Y_8$ represents a C1-C4 haloalkoxy group, a C2-C6 perfluoroalkyl group, a C1-C6 perfluoroalkylthio group, a C1-C6 perfluoroalkylsulfinyl group, or a C1-C6 perfluoroalkylsulfonyl group; and $Y_7$ represents a hydrogen atom, a halogen atom, or a C1-C4 alkyl group.

3. The imide compound according to claim 2, represented by the following Formula (1a):

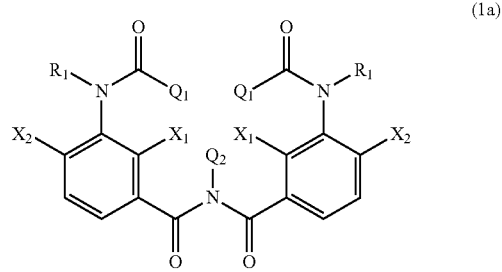

(1a)

wherein, in Formula (1a), $Q_2$ represents a phenyl group having a substituent represented by the following Formula (2):

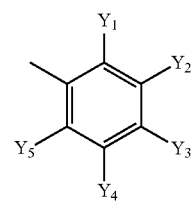

(2)

wherein, in Formula (2), each of $Y_1$ and $Y_5$ independently represents a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, or a cyano group; $Y_3$ represents a C2-C6 perfluoroalkyl group; and each of $Y_2$ and $Y_4$ independently represents a hydrogen atom or a C1-C4 alkyl group, each of $X_1$ and $X_2$ independently represents a hydrogen atom or a fluorine atom; $R_1$ represents a hydrogen atom or a C1-C4 alkyl group; and $Q_1$ represents:

a phenyl group that may have one or more substituents, which may be the same as or different from one another, selected from the substituent group consisting of a halogen atom, a C1-C4 alkyl group, a C1-C4 haloalkyl group, a cyano group and a nitro group, or a pyridyl group that may have one or more substituents, which may be the same as or different from one another, selected from the substituent group consisting of a halogen atom, a C1-C4 alkyl group, a C1-C4 haloalkyl group, a cyano group and a nitro group.

4. A method of manufacturing the imide compound represented by Formula (1) according to claim 1, the method comprising:

reacting a compound represented by the following Formula (4) with a compound represented by the following Formula (5):

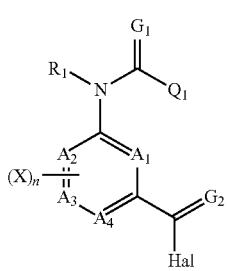

(4)

wherein, in Formula (4), each of $A_1$, $A_2$, $A_3$, and $A_4$ independently represents a carbon atom, a nitrogen atom, or an oxidized nitrogen atom; $R_1$ represents a hydrogen atom, a C1-C4 alkyl group, or a C1-C4 alkylcarbonyl group; each of $G_1$ and $G_2$ independently represents an oxygen atom or a sulfur atom; each X independently represents a hydrogen atom, a halogen atom, a C1-C3 alkyl group, or a trifluoromethyl group; when there are two or more X's, each X may be the same as or different from one another; and n represents an integer from 0 to 4;

$Q_1$ represents a phenyl group which may be substituted, a naphthyl group which may be substituted, or a heterocyclic group which may be substituted; and Hal represents a chlorine atom or a bromine atom,

(5)

wherein, in Formula (5), $Q_2$ represents a phenyl group or a heterocyclic group, each of which has one or more substituents, in which at least one of the one or more substituents represents a C1-C4 haloalkoxy group, a C2-C6 perfluoroalkyl group, a C1-C6 perfluoroalkylthio group, a C1-C6 perfluoroalkylsulfinyl group, or a C1-C6 perfluoroalkylsulfonyl group.

5. The method of manufacturing the imide compound according to claim 4, wherein $Q_1$ in Formula (4) represents:

a phenyl group that may have one or more substituents, which may be the same as or different from one another, selected from the substituent group consisting of a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a mono-(C1-C4) alkylamino group, a di-(C1-C4) alkylamino group, a cyano group, a nitro group, a hydroxy group, a formyl group, a C2-C4 alkylcarbonyl group, a C2-C4 alkylcarbonyloxy group, a C2-C4 alkoxycarbonyl group, an acetylamino group and a phenyl group; or a heterocyclic group selected from the group consisting of a pyridyl group, a pyridine-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrole group, a pyrazolyl group and a tetrazolyl group, wherein the heterocyclic group may have one or more substituents, which may be the same as or different from one another, selected from the substituent group consisting of a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a mono-(C1-C4) alkylamino group, a di-(C1-C4) alkylamino group, a cyano group, a nitro group, a hydroxy group, a formyl group, a C2-C4 alkylcarbonyl group, a C2-C4 alkylcarbonyloxy group, a C2-C4 alkoxycarbonyl group, an acetylamino group and a phenyl group.

6. An insecticide comprising, as an active ingredient, the imide compound according to claim 1.

7. An agricultural/horticultural insecticide comprising, as an active ingredient, the imide compound according to claim 1.

8. A method of using of an imide compound for protecting useful crops from pests, comprising treating a target useful crop or soil with an effective amount of the imide compound according to claim 1.

9. A composition comprising the imide compound according to claim 1 and at least one of an inert carrier or an adjuvant.

10. A mixed preparation comprising the imide compound according to claim 1 and at least one selected from an insecticide or a fungicide, other than the imide compound.

* * * * *